(12) United States Patent
Petterson et al.

(10) Patent No.: US 10,898,732 B2
(45) Date of Patent: Jan. 26, 2021

(54) MULTI-COLOR CHARGED PARTICLE DETECTOR APPARATUS AND METHOD OF USE THEREOF

(71) Applicants: Maureen Petterson, Somerville, MA (US); W. Davis Lee, Rockport, ME (US)

(72) Inventors: Maureen Petterson, Somerville, MA (US); W. Davis Lee, Rockport, ME (US)

( * ) Notice: Subject to any disclaimer, the term of this patent is extended or adjusted under 35 U.S.C. 154(b) by 0 days.

(21) Appl. No.: 16/538,648

(22) Filed: Aug. 12, 2019

(65) Prior Publication Data
US 2019/0366125 A1 Dec. 5, 2019

Related U.S. Application Data

(63) Continuation-in-part of application No. 15/901,770, filed on Feb. 21, 2018, now Pat. No. 10,532,228, (Continued)

(51) Int. Cl.
*A61N 5/10* (2006.01)
*A61B 6/03* (2006.01)
(Continued)

(52) U.S. Cl.
CPC ............. *A61N 5/1077* (2013.01); *A61B 6/03* (2013.01); *A61N 5/1044* (2013.01);
(Continued)

(58) Field of Classification Search
CPC ..... A61B 6/032; A61B 6/4258; A61B 6/4266; A61B 6/482; A61B 6/00; A61N 2005/1054; A61N 2005/1087; A61N 5/1067; A61N 5/107; A61N 2005/1076; A61N 5/1064; A61N 5/1065; G21K 5/04; G21K 1/087;
(Continued)

(56) References Cited

U.S. PATENT DOCUMENTS 6,392,236 B1 * 5/2002 Maekawa ............. G01T 1/2008
250/369
9,194,963 B2 * 11/2015 Myung .................... G01T 1/20
(Continued)

*Primary Examiner* — David A Vanore
(74) *Attorney, Agent, or Firm* — Hazen Patent Group, LLC; Kevin H. Hazen

(57) ABSTRACT

The invention comprises a method and apparatus for using a multi-layer multi-color scintillation based detector element to image a tumor of a patient using a process of determining residual energies of positively charged particles after passing through the patient, the process comprising the steps of: (1) transmitting the positively charged particles at known energies through the patient and into a multi-layer detector element; (2) detecting first and second secondary photons, resultant from passage of the positively charged particles, respectively from a first layer of a first scintillation material and a second layer of a second scintillation material at two respective layer depths, where the first wavelength range differs from the second wavelength range; (4) determining residual energies of the positively charged particles, using output from the step of detecting; and (5) relating the residual energies to body densities to generate an image.

2 Claims, 41 Drawing Sheets

Related U.S. Application Data which is a continuation-in-part of application No. 15/892,240, filed on Feb. 8, 2018, which is a continuation-in-part of application No. 15/838,072, filed on Dec. 11, 2017, now abandoned, which is a continuation-in-part of application No. 15/823,148, filed on Nov. 27, 2017, which is a continuation-in-part of application No. 15/467,840, filed on Mar. 23, 2017, which is a continuation-in-part of application No. 15/402,739, filed on Jan. 10, 2017, now Pat. No. 10,188,877, which is a continuation-in-part of application No. 15/348,625, filed on Nov. 10, 2016, now Pat. No. 9,855,444, which is a continuation-in-part of application No. 15/167,617, filed on May 27, 2016, now Pat. No. 9,737,733, said application No. 15/892,240 is a continuation-in-part of application No. 15/868,897, filed on Jan. 11, 2018, which is a continuation of application No. 15/152,479, filed on May 11, 2016, now Pat. No. 10,213,626, which is a continuation-in-part of application No. 14/216,788, filed on Mar. 17, 2014, now Pat. No. 9,682,254, which is a continuation-in-part of application No. 13/087,096, filed on Apr. 14, 2011, now Pat. No. 9,044,600.

(60) Provisional application No. 61/324,776, filed on Apr. 16, 2010.

(51) Int. Cl.
*G21K 1/093* (2006.01)
*G21K 5/04* (2006.01)
*G21K 1/087* (2006.01)
*H01J 35/14* (2006.01)

(52) U.S. Cl.
CPC ......... *A61N 5/1067* (2013.01); *A61N 5/1082* (2013.01); *G21K 1/087* (2013.01); *G21K 1/093* (2013.01); *G21K 5/04* (2013.01); *A61N 5/107* (2013.01); *A61N 2005/1074* (2013.01); *A61N 2005/1087* (2013.01); *A61N 2005/1097* (2013.01); *H01J 35/14* (2013.01)

(58) Field of Classification Search
CPC .... G21K 1/10; G01T 3/06; G01T 1/20; G01T 1/2008; G01T 1/06; G01T 1/2006; G01T 1/2018; G01N 2223/107; G01N 23/046; H01J 2237/2444; H01J 35/14; H01J 49/025

USPC .... 250/281, 282, 368, 370.11, 486.1, 487.1; 378/62

See application file for complete search history.

(56) References Cited

U.S. PATENT DOCUMENTS

| | | | | |
|---|---|---|---|---|
| 9,354,328 | B2* | 5/2016 | Vogtmeier | G01T 1/2008 |
| 10,209,372 | B2* | 2/2019 | Arodzero | G01T 1/2006 |
| 10,532,228 | B2* | 1/2020 | Petterson | A61B 6/032 |
| 2003/0010942 | A1* | 1/2003 | Kuwabara | G01T 1/2928 |
| | | | | 250/580 |
| 2005/0208290 | A1* | 9/2005 | Patel | C09K 11/06 |
| | | | | 428/323 |
| 2011/0095177 | A1* | 4/2011 | Giannakopulos | H01J 49/025 |
| | | | | 250/282 |
| 2013/0287170 | A1* | 10/2013 | Ebstein | G01N 23/04 |
| | | | | 378/62 |
| 2014/0306117 | A1* | 10/2014 | Vacheret | G01T 3/06 |
| | | | | 250/366 |
| 2015/0071408 | A1* | 3/2015 | Ebstein | A61N 5/1075 |
| | | | | 378/65 |
| 2015/0241579 | A1* | 8/2015 | Menge | G01V 5/0091 |
| | | | | 250/368 |
| 2016/0313452 | A1* | 10/2016 | Hartmann | G01T 1/16 |
| 2016/0354045 | A1* | 12/2016 | Lee | A61N 5/1067 |
| 2016/0354048 | A1* | 12/2016 | Lee | A61N 5/1082 |
| 2016/0354616 | A1* | 12/2016 | Lee | A61B 6/032 |
| 2016/0367207 | A1* | 12/2016 | Michaud | A61B 6/0457 |
| 2016/0375269 | A1* | 12/2016 | Michaud | A61B 6/0457 |
| | | | | 600/1 |
| 2017/0014646 | A1* | 1/2017 | Lee | A61N 5/1044 |
| 2017/0014647 | A1* | 1/2017 | Michaud | A61N 5/1082 |
| 2017/0036041 | A1* | 2/2017 | Reichert | A61B 6/032 |
| 2017/0043187 | A1* | 2/2017 | Lee | A61N 5/1077 |
| 2017/0056688 | A1* | 3/2017 | Penfold | A61N 5/1082 |
| 2017/0106213 | A1* | 4/2017 | Lee | A61N 5/1082 |
| 2017/0128029 | A1* | 5/2017 | Penfold | A61B 6/4417 |
| 2017/0128747 | A1* | 5/2017 | Bennett | A61N 5/1049 |
| 2017/0150933 | A1* | 6/2017 | Bennett | A61B 6/4258 |
| 2017/0150934 | A1* | 6/2017 | Bennett | A61B 6/4417 |
| 2018/0172852 | A1* | 6/2018 | Newman | G01T 3/06 |
| 2018/0172853 | A1* | 6/2018 | Newman | G01T 3/06 |

* cited by examiner

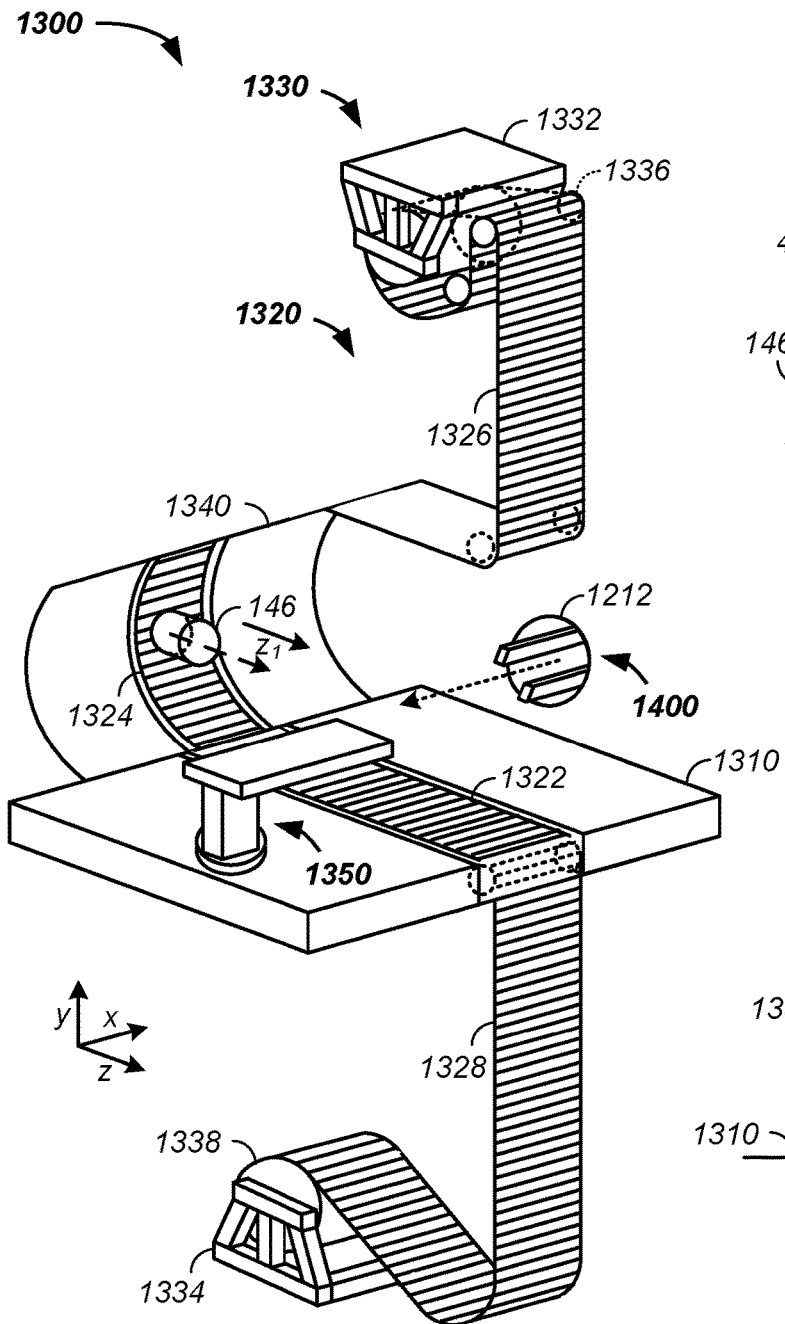
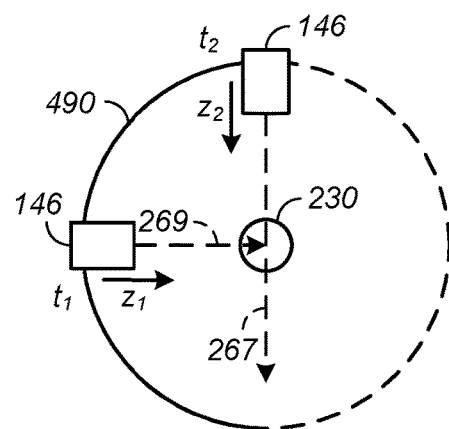
FIG. 13B
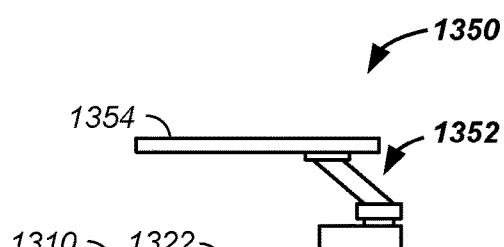
FIG. 13C
FIG. 13A

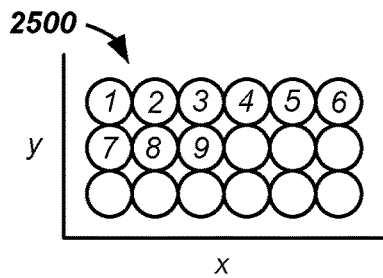
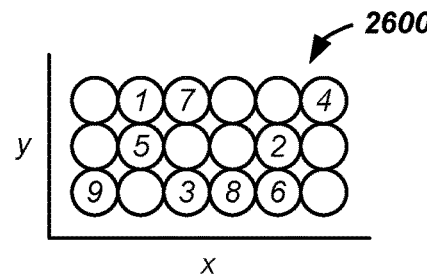
FIG. 25    FIG. 26
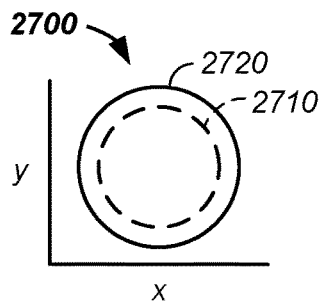
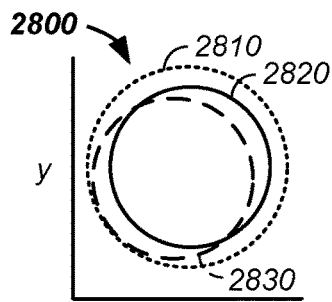
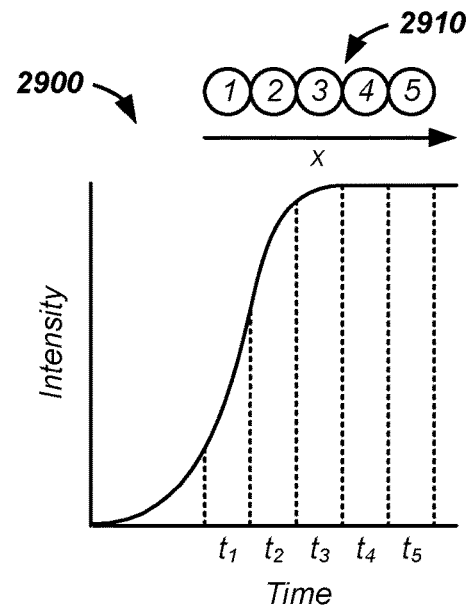
FIG. 27    FIG. 28    FIG. 29
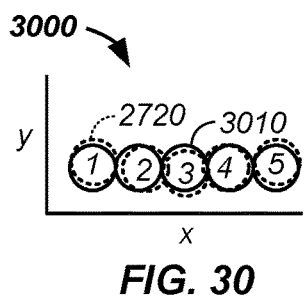
FIG. 30
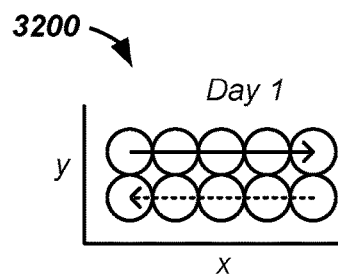
FIG. 31
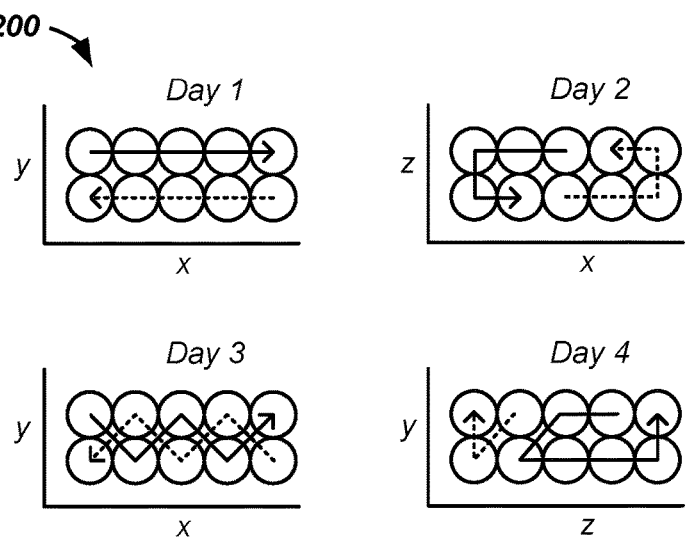
FIG. 32

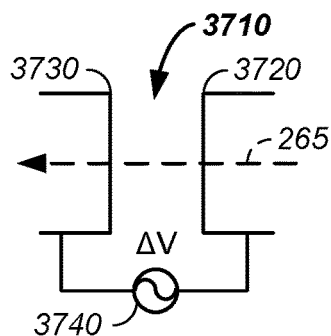 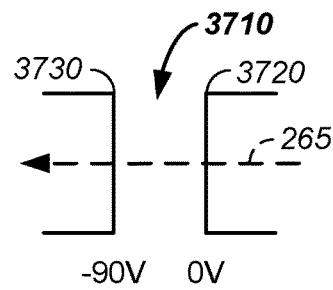 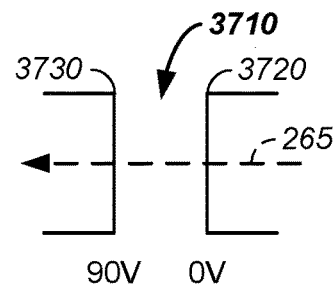
FIG. 37A  FIG. 37B  FIG. 37C
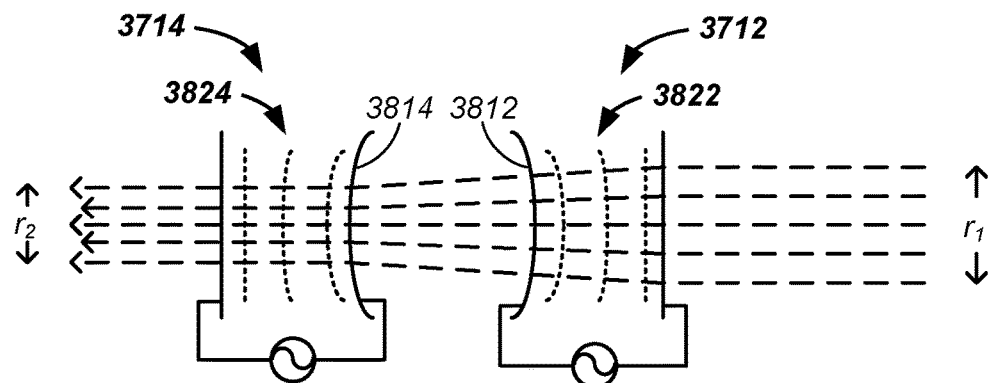
FIG. 38

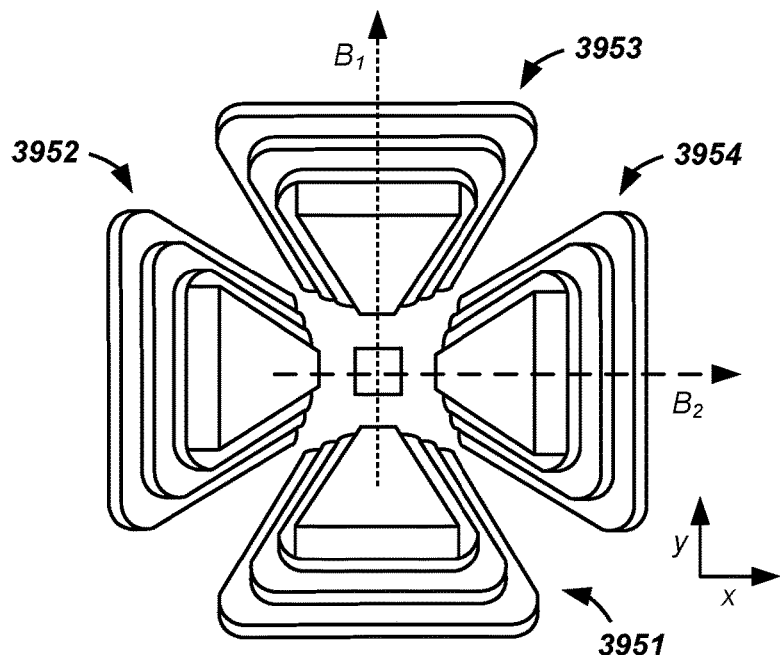
FIG. 39F
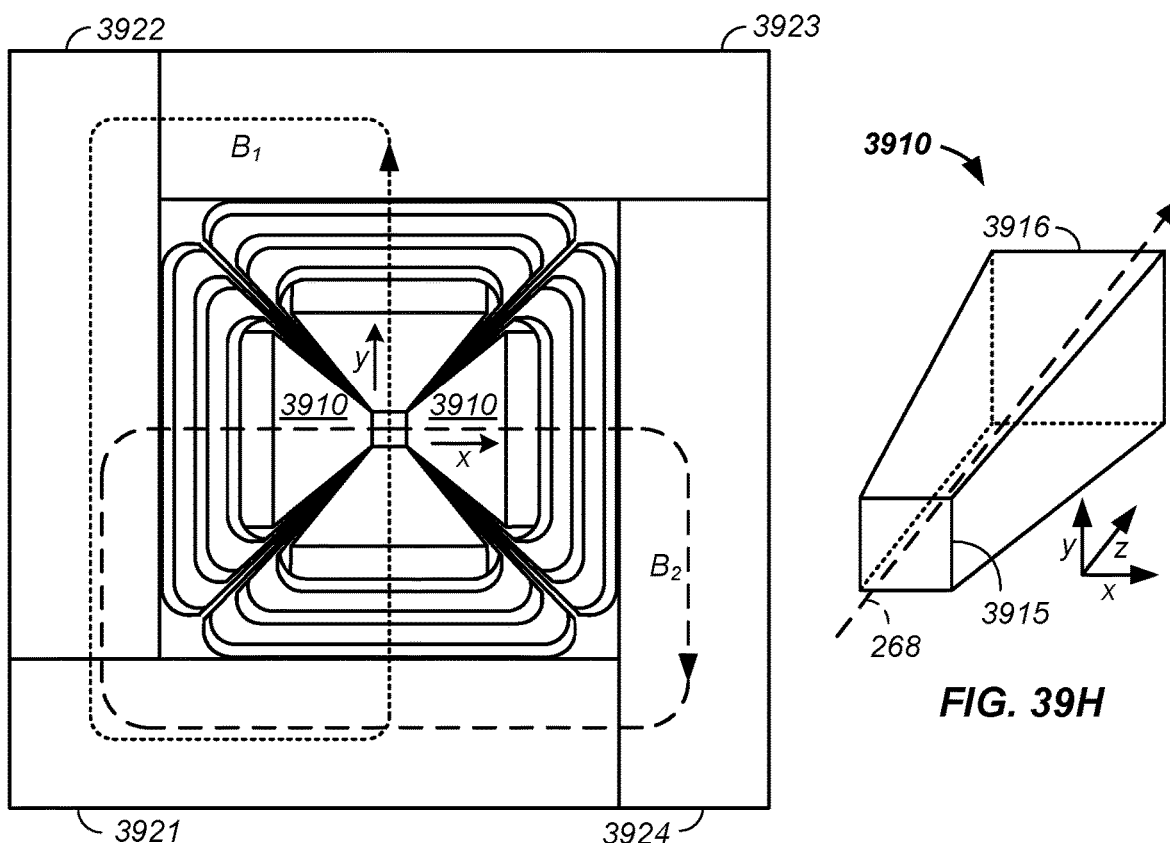
FIG. 39G
FIG. 39H

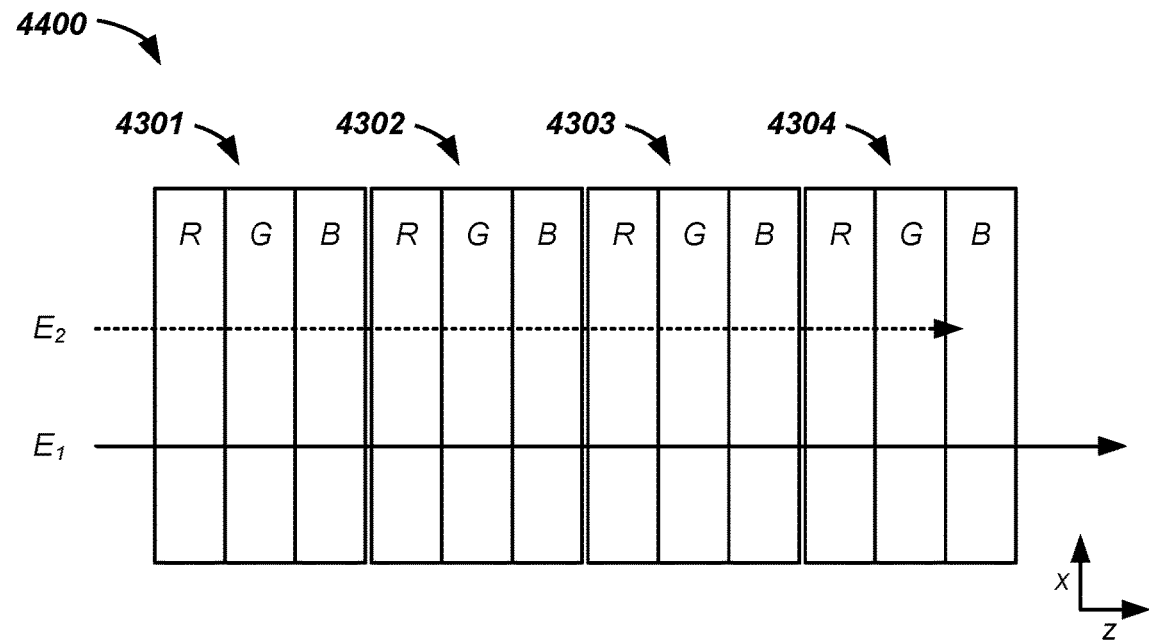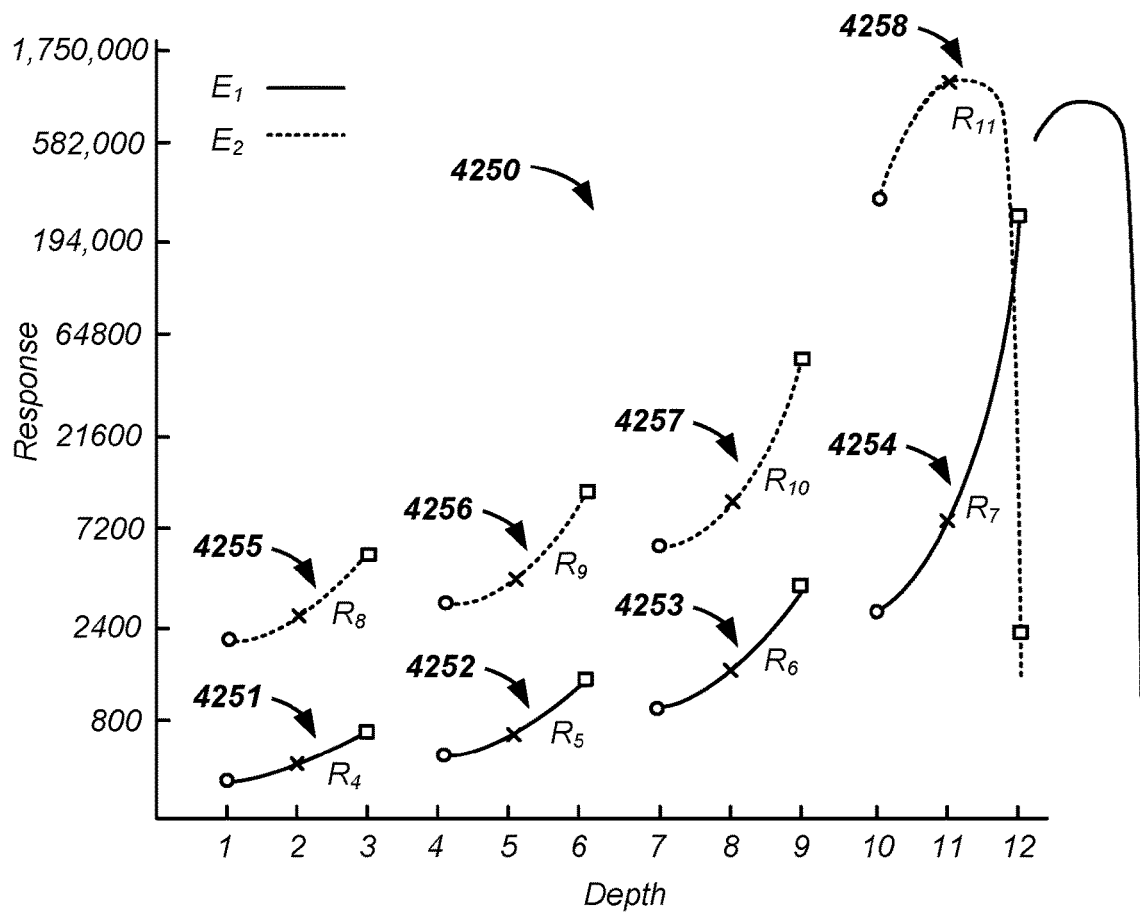
FIG. 44

US 10,898,732 B2

MULTI-COLOR CHARGED PARTICLE DETECTOR APPARATUS AND METHOD OF USE THEREOF

CROSS-REFERENCES TO RELATED APPLICATIONS

This application is a continuation-in-part of U.S. patent application Ser. No. 15/901,770 filed Feb. 21, 2018, which is a continuation-in-part of U.S. patent application Ser. No. 15/892,240 filed Feb. 8, 2018, which is:

a continuation-in-part of U.S. patent application Ser. No. 15/838,072 filed Dec. 11, 2017, which is a continuation-in-part of U.S. patent application Ser. No. 15/823,148 filed Nov. 27, 2017, which is a continuation-in-part of U.S. patent application Ser. No. 15/467,840 filed Mar. 23, 2017, which is a continuation-in-part of U.S. patent application Ser. No. 15/402,739 filed Jan. 10, 2017, which is a continuation-in-part of U.S. patent application Ser. No. 15/348,625 filed Nov. 10, 2016, which is a continuation-in-part of U.S. patent application Ser. No. 15/167,617 filed May 27, 2016; and a continuation-in-part of U.S. patent application Ser. No. 15/868,897 filed Jan. 11, 2018, which is a continuation of U.S. patent application Ser. No. 15/152,479 filed May 11, 2016, which is a continuation-in-part of U.S. patent application Ser. No. 14/216,788 filed Mar. 17, 2014, which is a continuation-in-part of U.S. patent application Ser. No. 13/087,096 filed Apr. 14, 2011, which claims benefit of U.S. provisional patent application No. 61/324,776 filed Apr. 16, 2010, all of which are incorporated herein in their entirety by this reference thereto.

BACKGROUND OF THE INVENTION

Field of the Invention

The invention relates generally to a cancer therapy treatment scanning apparatus and method of use thereof, such as for imaging and/or treating a tumor.

Discussion of the Prior Art

Cancer Treatment

Proton therapy works by aiming energetic ionizing particles, such as protons accelerated with a particle accelerator, onto a target tumor. These particles damage the DNA of cells, ultimately causing their death. Cancerous cells, because of their high rate of division and their reduced ability to repair damaged DNA, are particularly vulnerable to attack on their DNA.

Patents related to the current invention are summarized here.

Proton Beam Therapy System

F. Cole, et. al. of Loma Linda University Medical Center "Multi-Station Proton Beam Therapy System", U.S. Pat. No. 4,870,287 (Sep. 26, 1989) describe a proton beam therapy system for selectively generating and transporting proton beams from a single proton source and accelerator to a selected treatment room of a plurality of patient treatment rooms.

Problem

There exists in the art of charged particle cancer therapy a need for safe, accurate, precise, and rapid imaging of a patient and/or treatment of a tumor using charged particles.

SUMMARY OF THE INVENTION

The invention relates generally to a charged particle beam energy detector system of a charged particle cancer therapy system.

DESCRIPTION OF THE FIGURES

A more complete understanding of the present invention is derived by referring to the detailed description and claims when considered in connection with the Figures, wherein like reference numbers refer to similar items throughout the Figures.

FIG. 25 illustrates a linear row beam scan progression;

FIG. 26 illustrates a random beam scan progression;

FIG. 27 illustrates change in beam diameter;

FIG. 28 illustrated beam drift;

FIG. 29 illustrates a systematic treatment error;

FIG. 30 illustrates beam dithering;

FIG. 31 illustrates non-edge start progression scanning;

FIG. 32 illustrates day-to-day beam scan pattern variation;

FIGS. 37(A-C) illustrate voltage differences across a circulation beam gap;

FIG. 38 illustrates a particle bunch distribution tightening system;

FIG. 39F and FIG. 39G illustrate an orthogonal double dipole scanning system; FIG. 39H illustrates a truncated pyramid chamber through which charged particles traverse.

FIG. 44 illustrates a multi-element multi-color scintillator with associated response curves.

Figure 1A:
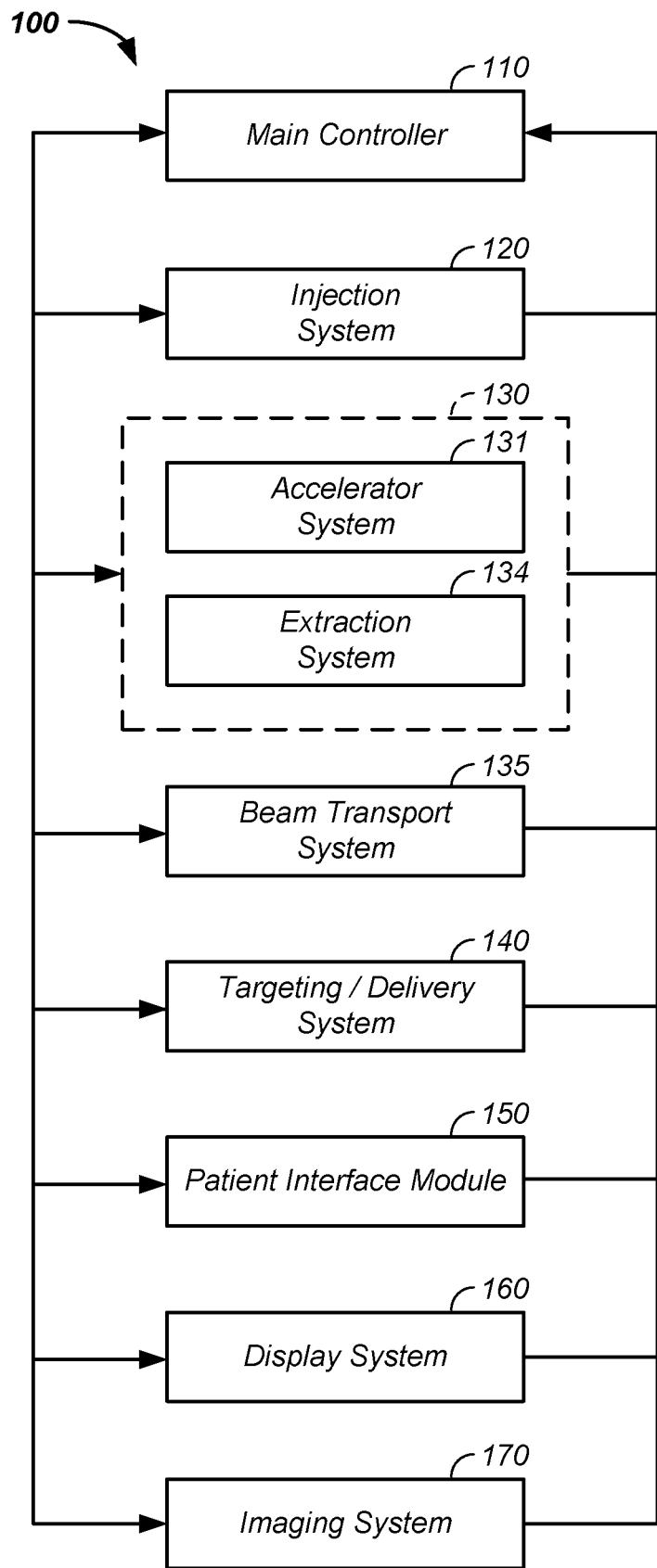
FIG. 1A illustrates component connections of a charged particle beam therapy system.

Elements and steps in the figures are illustrated for simplicity and clarity and have not necessarily been rendered according to any particular sequence. For example, steps that are performed concurrently or in different order are illustrated in the figures to help improve understanding of embodiments of the present invention.

DETAILED DESCRIPTION OF THE INVENTION

The invention comprises a method and apparatus for using a multi-layer multi-color scintillation based detector element to image a tumor of a patient using a process of determining residual energies of positively charged particles after passing through the patient, the process comprising the steps of: (1) transmitting the positively charged particles at known energies through the patient and into a multi-layer detector element; (2) detecting first and second secondary photons, resultant from passage of the positively charged particles, respectively from a first layer of a first scintillation material and a second layer of a second scintillation material at two respective layer depths, where the first wavelength range differs from the second wavelength range; (4) determining residual energies of the positively charged particles, using output from the step of detecting; and (5) relating the residual energies to the body to generate an image.

The above described embodiment is optionally used in combination with a proton therapy cancer treatment system and/or a proton tomography imaging system.

The above described embodiment is optionally used in combination with a set of fiducial marker detectors configured to detect photons emitted from and/or reflected off of a set of fiducial markers positioned on one or more objects in a treatment room and resultant determined distances and/or calculated angles are used to determine relative positions of multiple objects or elements in the treatment room. Generally, in an iterative process, at a first time objects, such as a treatment beamline output nozzle, a specific potion of a patient relative to a tumor, a scintillation detection material, an X-ray system element, and/or a detection element, are mapped and relative positions and/or angles therebetween are determined. At a second time, the position of the mapped objects is used in: (1) imaging, such as X-ray, positron emission tomography, and/or proton beam imaging and/or (2) beam targeting and treatment, such as positively charged particle based cancer treatment. As relative positions of objects in the treatment room are dynamically determined using the fiducial marking system, engineering and/or mathematical constraints of a treatment beamline isocenter is removed.

In combination, a method and apparatus is described for determining a position of a tumor in a patient for treatment of the tumor using positively charged particles in a treatment room. More particularly, the method and apparatus use a set of fiducial markers and fiducial detectors to mark/determine relative position of static and/or movable objects in a treatment room using photons passing from the markers to the detectors. Further, position and orientation of at least one of the objects is calibrated to a reference line, such as a zero-offset beam treatment line passing through an exit nozzle, which yields a relative position of each fiducially marked object in the treatment room. Treatment calculations are subsequently determined using the reference line and/or points thereon. The inventor notes that the treatment calculations are optionally and preferably performed without use of an isocenter point, such as a central point about which a treatment room gantry rotates, which eliminates mechanical errors associated with the isocenter point being an isocenter volume in practice.

In combination, a method and apparatus for imaging a tumor of a patient using positively charged particles and X-rays, comprises the steps of: (1) transporting the positively charged particles from an accelerator to a patient position using a beam transport line, where the beam transport line comprises a positively charged particle beam path and an X-ray beam path; (2) detecting scintillation induced by the positively charged particles using a scintillation detector system; (3) detecting X-rays using an X-ray detector system; (4) positioning a mounting rail through linear extension/retraction to: at a first time and at a first extension position of the mounting rail, position the scintillation detector system opposite the patient position from the exit nozzle and at a second time and at a second extension position of the mounting rail, position the X-ray detector system opposite the patient position from the exit nozzle; (5) generating an image of the tumor using output of the scintillation detector system and the X-ray detector system; and (6) alternating between the step of detecting scintillation and treating the tumor via irradiation of the tumor using the positively charged particles.

In combination, a tomography system is optionally used in combination with a charged particle cancer therapy system. The tomography system uses tomography or tomographic imaging, which refers to imaging by sections or sectioning through the use of a penetrating wave, such as a positively charge particle from an injector and/or accelerator. Optionally and preferably, a common injector, accelerator, and beam transport system is used for both charged particle based tomographic imaging and charged particle cancer therapy. In one case, an output nozzle of the beam transport system is positioned with a gantry system while the gantry system and/or a patient support maintains a scintillation plate of the tomography system on the opposite side of the patient from the output nozzle.

In another example, a charged particle state determination system, of a cancer therapy system or tomographic imaging system, uses one or more coated layers in conjunction with a scintillation material, scintillation detector and/or a tomographic imaging system at time of tumor and surrounding tissue sample mapping and/or at time of tumor treatment, such as to determine an input vector of the charged particle beam into a patient and/or an output vector of the charged particle beam from the patient.

In another example, the charged particle tomography apparatus is used in combination with a charged particle cancer therapy system. For example, tomographic imaging of a cancerous tumor is performed using charged particles generated with an injector, accelerated with an accelerator, and guided with a delivery system. The cancer therapy system uses the same injector, accelerator, and guided delivery system in delivering charged particles to the cancerous tumor. For example, the tomography apparatus and cancer therapy system use a common raster beam method and apparatus for treatment of solid cancers. More particularly, the invention comprises a multi-axis and/or multi-field raster beam charged particle accelerator used in: (1) tomography and (2) cancer therapy. Optionally, the system independently controls patient translation position, patient rotation position, two-dimensional beam trajectory, delivered radiation beam energy, delivered radiation beam intensity, beam velocity, timing of charged particle delivery, and/or distribution of radiation striking healthy tissue. The system operates in conjunction with a negative ion beam source, synchrotron, patient positioning, imaging, and/or targeting method and apparatus to deliver an effective and uniform dose of radiation to a tumor while distributing radiation striking healthy tissue.

For clarity of presentation and without loss of generality, throughout this document, treatment systems and imaging systems are described relative to a tumor of a patient. However, more generally any sample is imaged with any of the imaging systems described herein and/or any element of the sample is treated with the positively charged particle beam(s) described herein.

Charged Particle Beam Therapy

Throughout this document, a charged particle beam therapy system, such as a proton beam, hydrogen ion beam, or carbon ion beam, is described. Herein, the charged particle beam therapy system is described using a proton beam. However, the aspects taught and described in terms of a proton beam are not intended to be limiting to that of a proton beam and are illustrative of a charged particle beam system, a positively charged beam system, and/or a multiply charged particle beam system, such as $C^{4+}$ or $C^{6+}$. Any of the techniques described herein are equally applicable to any charged particle beam system.

Referring now to FIG. 1A, a charged particle beam system 100 is illustrated. The charged particle beam preferably comprises a number of subsystems including any of: a main controller 110; an injection system 120; a synchrotron 130 that typically includes: (1) an accelerator system 131 and (2) an internal or connected extraction system 134; a radio-frequency cavity system 180; a beam transport system 135; a scanning/targeting/delivery system 140; a nozzle system 146; a patient interface module 150; a display system 160; and/or an imaging system 170.

An exemplary method of use of the charged particle beam system 100 is provided. The main controller 110 controls one or more of the subsystems to accurately and precisely deliver protons to a tumor of a patient. For example, the main controller 110 obtains an image, such as a portion of a body and/or of a tumor, from the imaging system 170. The main controller 110 also obtains position and/or timing information from the patient interface module 150. The main controller 110 optionally controls the injection system 120 to inject a proton into a synchrotron 130. The synchrotron typically contains at least an accelerator system 131 and an extraction system 134. The main controller 110 preferably controls the proton beam within the accelerator system, such as by controlling speed, trajectory, and timing of the proton beam. The main controller then controls extraction of a proton beam from the accelerator through the extraction system 134. For example, the controller controls timing, energy, and/or intensity of the extracted beam. The controller 110 also preferably controls targeting of the proton beam through the scanning/targeting/delivery system 140 to the patient interface module 150 or a patient with a patient positioning system. One or more components of the patient interface module 150, such as translational and rotational position of the patient, are preferably controlled by the main controller 110. Further, display elements of the display system 160 are preferably controlled via the main controller 110. Displays, such as display screens, are typically provided to one or more operators and/or to one or more patients. In one embodiment, the main controller 110 times the delivery of the proton beam from all systems, such that protons are delivered in an optimal therapeutic manner to the tumor of the patient.

Herein, the main controller 110 refers to a single system controlling the charged particle beam system 100, to a single controller controlling a plurality of subsystems controlling the charged particle beam system 100, or to a plurality of individual controllers controlling one or more sub-systems of the charged particle beam system 100.

Example I

Charged Particle Cancer Therapy System Control

Figure 1B:
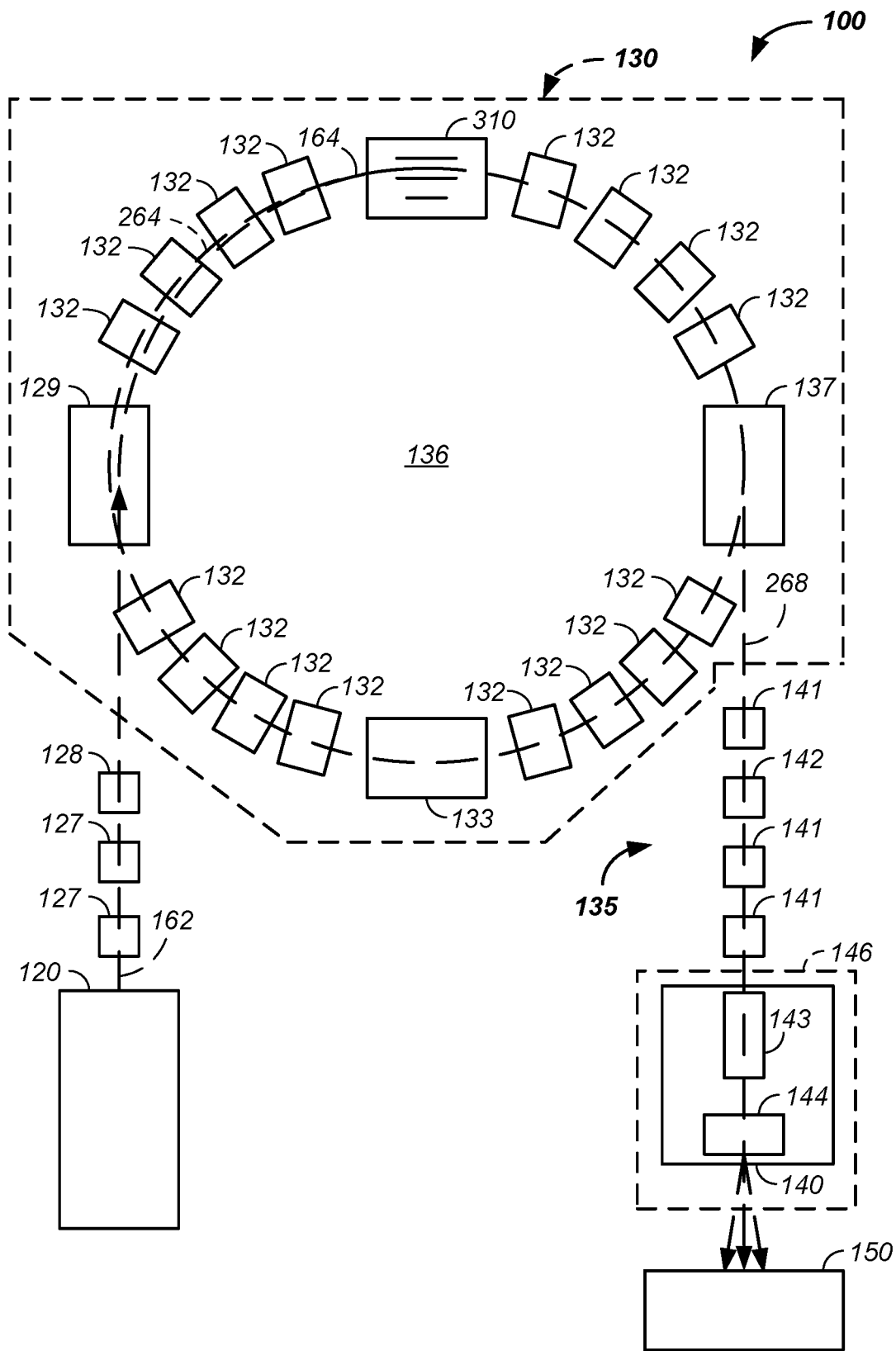
FIG. 1B illustrates a charged particle therapy system.

Referring now to FIG. 1B, an illustrative exemplary embodiment of one version of the charged particle beam system 100 is provided. The number, position, and described type of components is illustrative and non-limiting in nature. In the illustrated embodiment, the injection system 120 or ion source or charged particle beam source generates protons. The injection system 120 optionally includes one or more of: a negative ion beam source, a positive ion beam source, an ion beam focusing lens, and a tandem accelerator. The protons are delivered into a vacuum tube that runs into, through, and out of the synchrotron. The generated protons are delivered along an initial path 262. Optionally, focusing magnets 127, such as quadrupole magnets or injection quadrupole magnets, are used to focus the proton beam path. A quadrupole magnet is a focusing magnet. An injector bending magnet 128 bends the proton beam toward a plane of the synchrotron 130. The focused protons having an initial energy are introduced into an injector magnet 129, which is preferably an injection Lambertson magnet. Typically, the initial beam path 262 is along an axis off of, such as above, a circulating plane of the synchrotron 130. The injector bending magnet 128 and injector magnet 129 combine to move the protons into the synchrotron 130. Main bending magnets, dipole magnets, turning magnets, or circulating magnets 132 are used to turn the protons along a circulating beam path 164. A dipole magnet is a bending magnet. The main bending magnets 132 bend the initial beam path 262 into a circulating beam path 164. In this example, the main bending magnets 132 or circulating magnets are represented as four sets of four magnets to maintain the circulating beam path 164 into a stable circulating beam path. However, any number of magnets or sets of magnets are optionally used to move the protons around a single orbit in the circulation process. The protons pass through an accelerator 133. The accelerator accelerates the protons in the circulating beam path 164. As the protons are accelerated, the fields applied by the magnets are increased. Particularly, the speed of the protons achieved by the accelerator 133 are synchronized with magnetic fields of the main bending magnets 132 or circulating magnets to maintain stable circulation of the protons about a central point or region 136 of the synchrotron. At separate points in time the accelerator 133/main bending magnet 132 combination is used to accelerate and/or decelerate the circulating protons while maintaining the protons in the circulating path or orbit. An extraction element of an inflector/deflector system is used in combination with a Lambertson extraction magnet 137 to remove protons from their circulating beam path 164 within the synchrotron 130. One example of a deflector component is a Lambertson magnet. Typically the deflector moves the protons from the circulating plane to an axis off of the circulating plane, such as above the circulating plane. Extracted protons are preferably directed and/or focused using an extraction bending magnet 142 and optional extraction focusing magnets 141, such as quadrupole magnets, and optional bending magnets along a positively charged particle beam transport path 268 in a beam transport system 135, such as a beam path or proton beam path, into the scanning/targeting/delivery system 140. Two components of a scanning system 140 or targeting system typically include a first axis controller 143, such as a vertical control, and a second axis controller 144, such as a horizontal control. In one embodiment, the first axis controller 143 allows for about 100 mm of vertical or y-axis scanning of the proton beam 268 and the second axis controller 144 allows for about 700 mm of horizontal or x-axis scanning of the proton beam 268. A nozzle system 146 is used for directing the proton beam, for imaging the proton beam, for defining shape of the proton beam, and/or as a vacuum barrier between the low pressure beam path of the synchrotron and the atmosphere. Protons are delivered with control to the patient interface module 150 and to a tumor of a patient. All of the above listed elements are optional and may be used in various permutations and combinations.

Ion Extraction from Ion Source

For clarity of presentation and without loss of generality, examples focus on protons from the ion source. However, more generally cations of any charge are optionally extracted from a corresponding ion source with the techniques described herein. For instance, $C^{4+}$ or $C^{6+}$ are optionally extracted using the ion extraction methods and apparatus described herein. Further, by reversing polarity of the system, anions are optionally extracted from an anion source, where the anion is of any charge.

Herein, for clarity of presentation and without loss of generality, ion extraction is coupled with tumor treatment and/or tumor imaging. However, the ion extraction is optional used in any method or apparatus using a stream or time discrete bunches of ions.

Ion Extraction from Accelerator

Figure 1C:
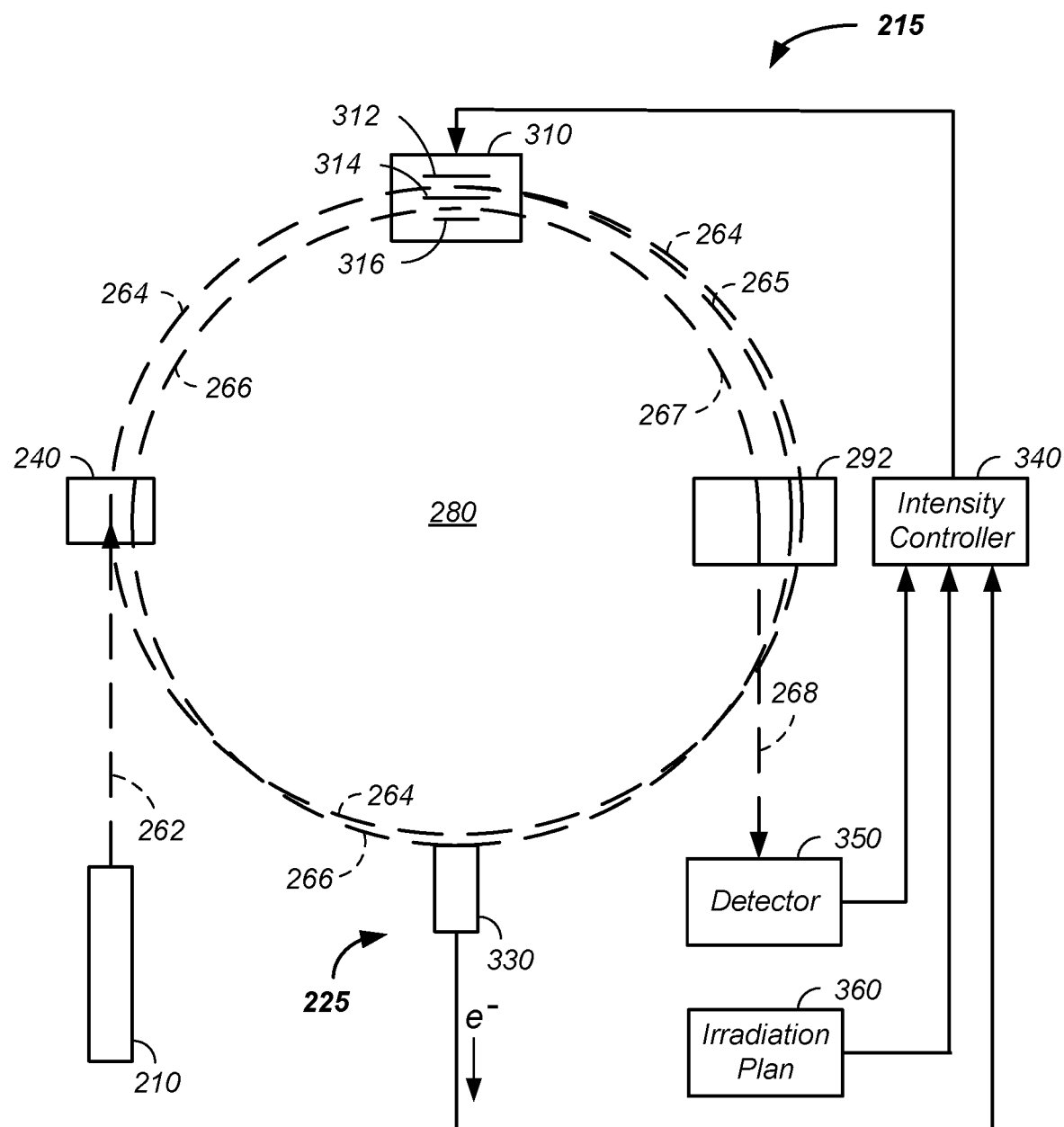
FIG. 1C illustrates an extraction system.

Referring now to FIG. 1C, both: (1) an exemplary proton beam extraction system 215 from the synchrotron 130 and (2) a charged particle beam intensity control system 225 are illustrated. For clarity, FIG. 1C removes elements represented in FIG. 1B, such as the turning magnets, which allows for greater clarity of presentation of the proton beam path as a function of time. Generally, protons are extracted from the synchrotron 130 by slowing the protons. As described, supra, the protons were initially accelerated in a circulating path, which is maintained with a plurality of main bending magnets 132. The circulating path is referred to herein as an original central beamline 264. The protons repeatedly cycle around a central point in the synchrotron 136. The proton path traverses through a radio frequency (RF) cavity system 310. To initiate extraction, an RF field is applied across a first blade 312 and a second blade 314, in the RF cavity system 310. The first blade 312 and second blade 314 are referred to herein as a first pair of blades.

In the proton extraction process, an RF voltage is applied across the first pair of blades, where the first blade 312 of the first pair of blades is on one side of the circulating proton beam path 264 and the second blade 314 of the first pair of blades is on an opposite side of the circulating proton beam path 264. The applied RF field applies energy to the circulating charged-particle beam. The applied RF field alters the orbiting or circulating beam path slightly of the protons from the original central beamline 264 to an altered circulating beam path 265. Upon a second pass of the protons through the RF cavity system, the RF field further moves the protons off of the original proton beamline 264. For example, if the original beamline is considered as a circular path, then the altered beamline is slightly elliptical. The frequency of the applied RF field is timed to apply outward or inward movement to a given band of protons circulating in the synchrotron accelerator. Orbits of the protons are slightly more off axis compared to the original circulating beam path 264. Successive passes of the protons through the RF cavity system are forced further and further from the original central beamline 264 by altering the direction and/or intensity of the RF field with each successive pass of the proton beam through the RF field. Timing of application of the RF field and/or frequency of the RF field is related to the circulating charged particles circulation pathlength in the synchrotron 130 and the velocity of the charged particles so that the applied RF field has a period, with a peak-to-peak time period, equal to a period of time of beam circulation in the synchrotron 130 about the center 136 or an integer multiple of the time period of beam circulation about the center 136 of the synchrotron 130. Alternatively, the time period of beam circulation about the center 136 of the synchrotron 130 is an integer multiple of the RF period time. The RF period is optionally used to calculated the velocity of the charged particles, which relates directly to the energy of the circulating charged particles.

The RF voltage is frequency modulated at a frequency about equal to the period of one proton cycling around the synchrotron for one revolution or at a frequency than is an integral multiplier of the period of one proton cycling about the synchrotron. The applied RF frequency modulated voltage excites a betatron oscillation. For example, the oscillation is a sine wave motion of the protons. The process of timing the RF field to a given proton beam within the RF cavity system is repeated thousands of times with each successive pass of the protons being moved approximately one micrometer further off of the original central beamline 264. For clarity, the approximately 1000 changing beam paths with each successive path of a given band of protons through the RF field are illustrated as the altered beam path 265. The RF time period is process is known, thus energy of the charged particles at time of hitting the extraction material 330, described infra, is known.

With a sufficient sine wave betatron amplitude, the altered circulating beam path 265 touches and/or traverses a extraction material 330, such as a foil or a sheet of foil. The foil is preferably a lightweight material, such as beryllium, a lithium hydride, a carbon sheet, or a material having low nuclear charge components.

Herein, a material of low nuclear charge is a material composed of atoms consisting essentially of atoms having six or fewer protons. The foil is preferably about 10 to 150 microns thick, is more preferably about 30 to 100 microns thick, and is still more preferably about 40 to 60 microns thick. In one example, the foil is beryllium with a thickness of about 50 microns. When the protons traverse through the foil, energy of the protons is lost and the speed of the protons is reduced. Typically, a current is also generated, described infra. Protons moving at the slower speed travel in the synchrotron with a reduced radius of curvature 266 compared to either the original central beamline 264 or the altered circulating path 265. The reduced radius of curvature 266 path is also referred to herein as a path having a smaller diameter of trajectory or a path having protons with reduced energy. The reduced radius of curvature 266 is typically about two millimeters less than a radius of curvature of the last pass of the protons along the altered proton beam path 265.

The thickness of the extraction material 330 is optionally adjusted to create a change in the radius of curvature, such as about ½, 1, 2, 3, or 4 mm less than the last pass of the protons 265 or original radius of curvature 264. The reduction in velocity of the charged particles transmitting through the extraction material 330 is calculable, such as by using the pathlength of the betatron oscillating charged particle beam through the extraction material 330 and/or using the density of the extraction material 330. Protons moving with the smaller radius of curvature travel between a second pair of blades. In one case, the second pair of blades is physically distinct and/or is separated from the first pair of blades. In a second case, one of the first pair of blades is also a member of the second pair of blades. For example, the second pair of blades is the second blade 314 and a third blade 316 in the RF cavity system 310. A high voltage DC signal, such as about 1 to 5 kV, is then applied across the second pair of blades, which directs the protons out of the synchrotron through an extraction magnet 137, such as a Lambertson extraction magnet, into a transport path 268.

Control of acceleration of the charged particle beam path in the synchrotron with the accelerator and/or applied fields of the turning magnets in combination with the above described extraction system allows for control of the intensity of the extracted proton beam, where intensity is a proton flux per unit time or the number of protons extracted as a function of time. For example, when a current is measured beyond a threshold, the RF field modulation in the RF cavity system is terminated or reinitiated to establish a subsequent cycle of proton beam extraction. This process is repeated to yield many cycles of proton beam extraction from the synchrotron accelerator.

In another embodiment, instead of moving the charged particles to the extraction material 330, the extraction material 330 is mechanically moved to the circulating charged particles. Particularly, the extraction material 330 is mechanically or electromechanically translated into the path of the circulating charged particles to induce the extraction process, described supra. In this case, the velocity or energy of the circulating charged particle beam is calculable using the pathlength of the beam path about the center 136 of the synchrotron 130 and from the force applied by the bending magnets 132.

In either case, because the extraction system does not depend on any change in magnetic field properties, it allows the synchrotron to continue to operate in acceleration or deceleration mode during the extraction process. Stated differently, the extraction process does not interfere with synchrotron acceleration. In stark contrast, traditional extraction systems introduce a new magnetic field, such as via a hexapole, during the extraction process. More particularly, traditional synchrotrons have a magnet, such as a hexapole magnet, that is off during an acceleration stage. During the extraction phase, the hexapole magnetic field is introduced to the circulating path of the synchrotron. The introduction of the magnetic field necessitates two distinct modes, an acceleration mode and an extraction mode, which are mutually exclusive in time. The herein described system allows for acceleration and/or deceleration of the proton during the extraction step and tumor treatment without the use of a newly introduced magnetic field, such as by a hexapole magnet.

Charged Particle Beam Intensity Control

Control of applied field, such as a radio-frequency (RF) field, frequency and magnitude in the RF cavity system 310 allows for intensity control of the extracted proton beam, where intensity is extracted proton flux per unit time or the number of protons extracted as a function of time.

Figure 3:
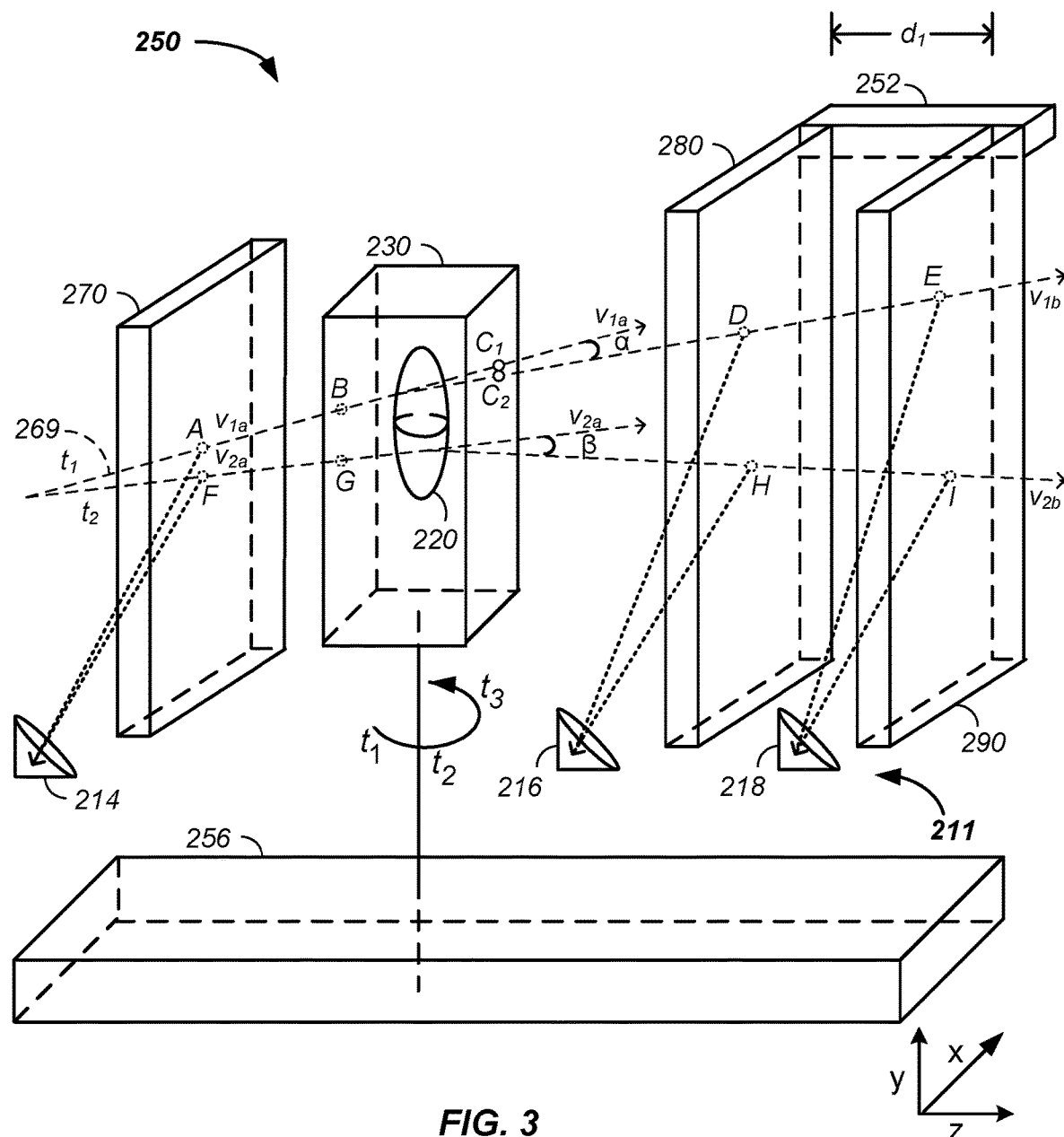
FIG. 3 illustrates a beam path identification system.

Still referring FIG. 3, the intensity control system 225 is further described. In this example, an intensity control feedback loop is added to the extraction system, described supra. When protons in the proton beam hit the extraction material 330 electrons are given off from the extraction material 330 resulting in a current. The resulting current is converted to a voltage and is used as part of an ion beam intensity monitoring system or as part of an ion beam feedback loop for controlling beam intensity. The voltage is optionally measured and sent to the main controller 110 or to an intensity controller subsystem 340, which is preferably in communication or under the direction of the main controller 110. More particularly, when protons in the charged particle beam path pass through the extraction material 330, some of the protons lose a small fraction of their energy, such as about one-tenth of a percent, which results in a secondary electron. That is, protons in the charged particle beam push some electrons when passing through extraction material 330 giving the electrons enough energy to cause secondary emission. The resulting electron flow results in a current or signal that is proportional to the number of protons going through the target or extraction material 330. The resulting current is preferably converted to voltage and amplified. The resulting signal is referred to as a measured intensity signal.

The amplified signal or measured intensity signal resulting from the protons passing through the extraction material 330 is optionally used in monitoring the intensity of the extracted protons and is preferably used in controlling the intensity of the extracted protons. For example, the measured intensity signal is compared to a goal signal, which is predetermined in an irradiation of the tumor plan. The difference between the measured intensity signal and the planned for goal signal is calculated. The difference is used as a control to the RF generator. Hence, the measured flow of current resulting from the protons passing through the extraction material 330 is used as a control in the RF generator to increase or decrease the number of protons undergoing betatron oscillation and striking the extraction material 330. Hence, the voltage determined off of the extraction material 330 is used as a measure of the orbital path and is used as a feedback control to control the RF cavity system.

In one example, the intensity controller subsystem 340 preferably additionally receives input from: (1) a detector 350, which provides a reading of the actual intensity of the proton beam and/or (2) an irradiation plan 360. The irradiation plan provides the desired intensity of the proton beam for each x, y, energy, and/or rotational position of the patient/tumor as a function of time. Thus, the intensity controller 340 receives the desired intensity from the irradiation plan 350, the actual intensity from the detector 350 and/or a measure of intensity from the extraction material 330, and adjusts the amplitude and/or the duration of application of the applied radio-frequency field in the RF cavity system 310 to yield an intensity of the proton beam that matches the desired intensity from the irradiation plan 360.

As described, supra, the protons striking the extraction material 330 is a step in the extraction of the protons from the synchrotron 130. Hence, the measured intensity signal is used to change the number of protons per unit time being extracted, which is referred to as intensity of the proton beam. The intensity of the proton beam is thus under algorithm control. Further, the intensity of the proton beam is controlled separately from the velocity of the protons in the synchrotron 130. Hence, intensity of the protons extracted and the energy of the protons extracted are independently variable. Still further, the intensity of the extracted protons is controllably variable while scanning the charged particles beam in the tumor from one voxel to an adjacent voxel as a separate hexapole and separated time period from acceleration and/or treatment is not required, as described supra.

For example, protons initially move at an equilibrium trajectory in the synchrotron 130. An RF field is used to excite or move the protons into a betatron oscillation. In one case, the frequency of the protons orbit is about 10 MHz. In one example, in about one millisecond or after about 10,000 orbits, the first protons hit an outer edge of the target material 130. The specific frequency is dependent upon the period of the orbit. Upon hitting the material 130, the protons push electrons through the foil to produce a current. The current is converted to voltage and amplified to yield a measured intensity signal. The measured intensity signal is used as a feedback input to control the applied RF magnitude or RF field. An energy beam sensor, described infra, is optionally used as a feedback control to the RF field frequency or RF field of the RF field extraction system 310 to dynamically control, modify, and/or alter the delivered charge particle beam energy, such as in a continuous pencil beam scanning system operating to treat tumor voxels without alternating between an extraction phase and a treatment phase. Preferably, the measured intensity signal is compared to a target signal and a measure of the difference between the measured intensity signal and target signal is used to adjust the applied RF field in the RF cavity system 310 in the extraction system to control the intensity of the protons in the extraction step. Stated again, the signal resulting from the protons striking and/or passing through the material 130 is used as an input in RF field modulation. An increase in the magnitude of the RF modulation results in protons hitting the foil or material 130 sooner. By increasing the RF, more protons are pushed into the foil, which results in an increased intensity, or more protons per unit time, of protons extracted from the synchrotron 130.

In another example, a detector 350 external to the synchrotron 130 is used to determine the flux of protons extracted from the synchrotron and a signal from the external detector is used to alter the RF field, RF intensity, RF amplitude, and/or RF modulation in the RF cavity system 310. Here the external detector generates an external signal, which is used in a manner similar to the measured intensity signal, described in the preceding paragraphs. Preferably, an algorithm or irradiation plan 360 is used as an input to the intensity controller 340, which controls the RF field modulation by directing the RF signal in the betatron oscillation generation in the RF cavity system 310. The irradiation plan 360 preferably includes the desired intensity of the charged particle beam as a function of time and/or energy of the charged particle beam as a function of time, for each patient rotation position, and/or for each x-, y-position of the charged particle beam.

In yet another example, when a current from extraction material 330 resulting from protons passing through or hitting material is measured beyond a threshold, the RF field modulation in the RF cavity system is terminated or reinitiated to establish a subsequent cycle of proton beam extraction. This process is repeated to yield many cycles of proton beam extraction from the synchrotron accelerator.

In still yet another embodiment, intensity modulation of the extracted proton beam is controlled by the main controller 110. The main controller 110 optionally and/or additionally controls timing of extraction of the charged particle beam and energy of the extracted proton beam.

The benefits of the system include a multi-dimensional scanning system. Particularly, the system allows independence in: (1) energy of the protons extracted and (2) intensity of the protons extracted. That is, energy of the protons extracted is controlled by an energy control system and an intensity control system controls the intensity of the extracted protons. The energy control system and intensity control system are optionally independently controlled. Preferably, the main controller 110 controls the energy control system and the main controller 110 simultaneously controls the intensity control system to yield an extracted proton beam with controlled energy and controlled intensity where the controlled energy and controlled intensity are independently variable and/or continually available as a separate extraction phase and acceleration phase are not required, as described supra. Thus the irradiation spot hitting the tumor is under independent control of:

time;
    energy;
    intensity;
    x-axis position, where the x-axis represents horizontal movement of the proton beam relative to the patient, and
    y-axis position, where the y-axis represents vertical movement of the proton beam relative to the patient.

In addition, the patient is optionally independently translated and/or rotated relative to a translational axis of the proton beam at the same time.

Beam Transport

The beam transport system 135 is used to move the charged particles from the accelerator to the patient, such as via a nozzle in a gantry, described infra.

Nozzle

After extraction from the synchrotron 130 and transport of the charged particle beam along the proton beam path 268 in the beam transport system 135, the charged particle beam exits through the nozzle system 146. In one example, the nozzle system includes a nozzle foil covering an end of the nozzle system 146 or a cross-sectional area within the nozzle system forming a vacuum seal. The nozzle system includes a nozzle that expands in x/y-cross-sectional area along the z-axis of the proton beam path 268 to allow the proton beam 268 to be scanned along the x-axis and y-axis by the vertical control element and horizontal control element, respectively. The nozzle foil is preferably mechanically supported by the outer edges of an exit port of the nozzle or nozzle system 146. An example of a nozzle foil is a sheet of about 0.1 inch thick aluminum foil. Generally, the nozzle foil separates atmosphere pressures on the patient side of the nozzle foil from the low pressure region, such as about $10^{-5}$ to $10^{-7}$ torr region, on the synchrotron 130 side of the nozzle foil. The low pressure region is maintained to reduce scattering of the circulating charged particle beam in the synchrotron. Herein, the exit foil of the nozzle is optionally the first tracking plane 760. tracking sheet, or sheet of the charged particle beam state determination system 250, described infra.

Tomography/Beam State

In one embodiment, the charged particle tomography apparatus is used to image a tumor in a patient. As current beam position determination/verification is used in both tomography and cancer therapy treatment, for clarity of presentation and without limitation beam state determination is also addressed in this section. However, beam state determination is optionally used separately and without tomography.

In another example, the charged particle tomography apparatus is used in combination with a charged particle cancer therapy system using common elements. For example, tomographic imaging of a cancerous tumor is performed using charged particles generated with an injector, accelerator, and guided with a delivery system that are part of the cancer therapy system, described supra.

In various examples, the tomography imaging system is optionally simultaneously operational with a charged particle cancer therapy system using common elements, allows tomographic imaging with rotation of the patient, is operational on a patient in an upright, semi-upright, and/or horizontal position, is simultaneously operational with X-ray imaging, and/or allows use of adaptive charged particle cancer therapy. Further, the common tomography and cancer therapy apparatus elements are optionally operational in a multi-axis and/or multi-field raster beam mode.

In conventional medical X-ray tomography, a sectional image through a body is made by moving one or both of an X-ray source and the X-ray film in relative to the patient during the exposure. By modifying the direction and extent of the movement, operators can select different focal planes, which contain the structures of interest. More modern variations of tomography involve gathering projection data from multiple directions by moving the X-ray source and feeding the data into a tomographic reconstruction software algorithm processed by a computer. Herein, in stark contrast to known methods, the radiation source is a charged particle, such as a proton ion beam or a carbon ion beam. A proton beam is used herein to describe the tomography system, but the description applies to a heavier ion beam, such as a carbon ion beam. Further, in stark contrast to known techniques, herein the radiation source is optionally stationary while the patient is rotated.

Figure 2:
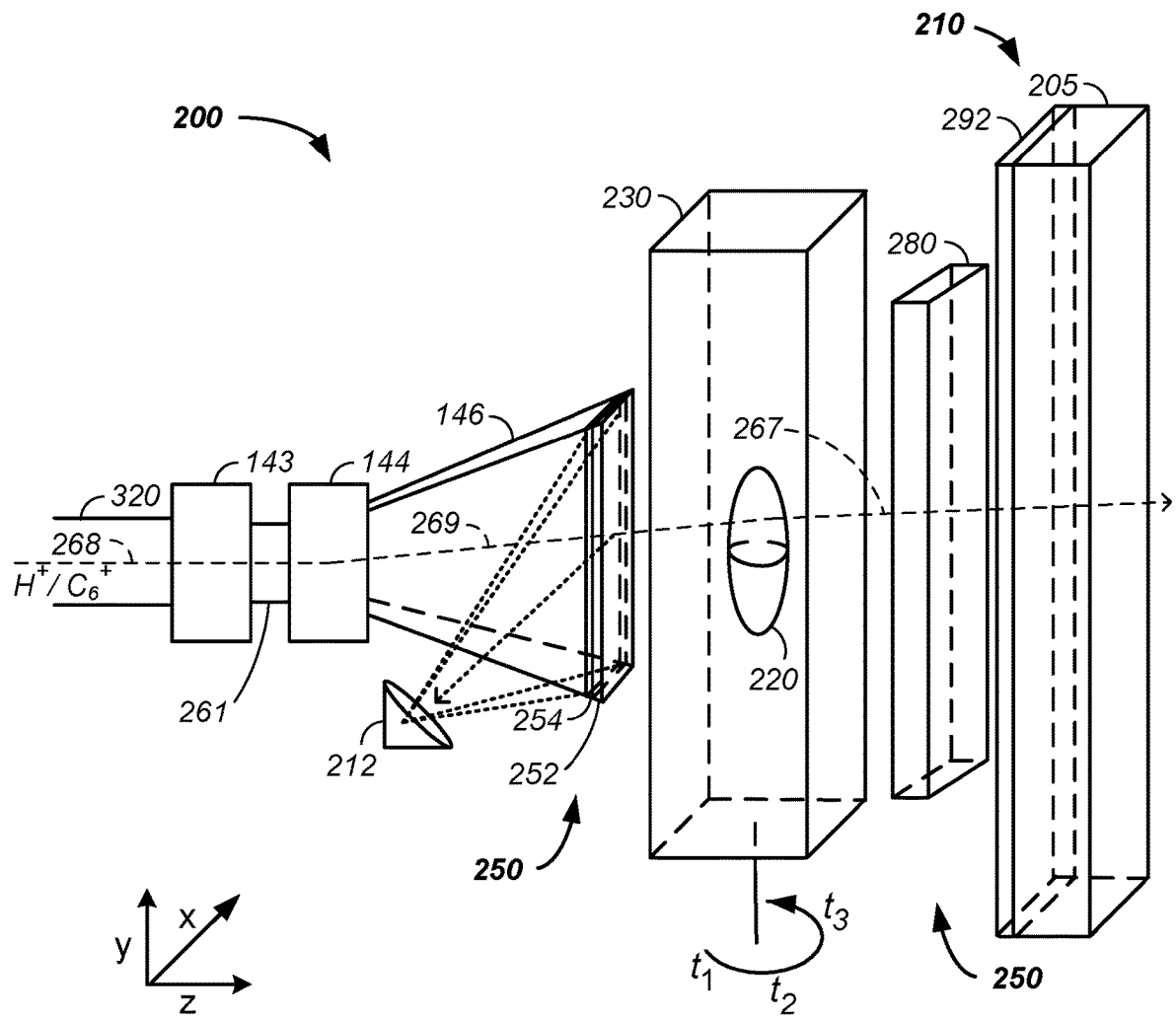
FIG. 2 illustrates a tomography system.

Referring now to FIG. 2, an example of a tomography apparatus is described and an example of a beam state determination is described. In this example, the tomography system 200 uses elements in common with the charged particle beam system 100, including elements of one or more of the injection system 120, the accelerator 130, a positively charged particle beam transport path 268 within a beam transport housing 261 in the beam transport system 135, the targeting/delivery system 140, the patient interface module 150, the display system 160, and/or the imaging system 170, such as the X-ray imaging system. The scintillation material is optionally one or more scintillation plates, such as a scintillating plastic, used to measure energy, intensity, and/or position of the charged particle beam. For instance, a scintillation material of scintillation detector element 205 of a scintillation detector system 210 or scintillation plate is positioned behind the patient 230 relative to the targeting/delivery system 140 elements, which is optionally used to measure intensity and/or position of the charged particle beam after transmitting through the patient. Optionally, a second scintillation plate or a charged particle induced photon emitting sheet, described infra, is positioned prior to the patient 230 relative to the targeting/delivery system 140 elements, which is optionally used to measure incident intensity and/or position of the charged particle beam prior to transmitting through the patient. The charged particle beam system 100 as described has proven operation at up to and including 330 MeV, which is sufficient to send protons through the body and into contact with the scintillation material. Particularly, 250 MeV to 330 MeV are used to pass the beam through a standard sized patient with a standard sized pathlength, such as through the chest. The intensity or count of protons hitting the plate as a function of position is used to create an image. The velocity or energy of the proton hitting the scintillation plate is also used in creation of an image of the tumor 220 and/or an image of the patient 230. The patient 230 is rotated about the y-axis and a new image is collected. Preferably, a new image is collected with about every one degree of rotation of the patient resulting in about 360 images that are combined into a tomogram using tomographic reconstruction software. The tomographic reconstruction software uses overlapping rotationally varied images in the reconstruction. Optionally, a new image is collected at about every 2, 3, 4, 5, 10, 15, 30, or 45 degrees of rotation of the patient.

Herein, the scintillation material or scintillator, of the scintillation detection system, is any material that emits a photon when struck by a positively charged particle or when a positively charged particle transfers energy to the scintillation material sufficient to cause emission of light. Optionally, the scintillation material emits the photon after a delay, such as in fluorescence or phosphorescence. However, preferably, the scintillator has a fast fifty percent quench time, such as less than 0.0001, 0.001, 0.01, 0.1, 1, 10, 100, or 1,000 milliseconds, so that the light emission goes dark, falls off, or terminates quickly. Preferred scintillation materials include sodium iodide, potassium iodide, cesium iodide, an iodide salt, and/or a doped iodide salt. Additional examples of the scintillation materials include, but are not limited to: an organic crystal, a plastic, a glass, an organic liquid, a luminophor, and/or an inorganic material or inorganic crystal, such as barium fluoride, $BaF_2$; calcium fluoride, $CaF_2$, doped calcium fluoride, sodium iodide, NaI; doped sodium iodide, sodium iodide doped with thallium, NaI(Tl); cadmium tungstate, $CdWO_4$; bismuth germanate; cadmium tungstate, $CdWO_4$; calcium tungstate, $CaWO_4$; cesium iodide, CsI; doped cesium iodide; cesium iodide doped with thallium, CsI(Tl); cesium iodide doped with sodium CsI (Na); potassium iodide, KI; doped potassium iodide, gadolinium oxysulfide, $Gd_2O_2S$; lanthanum bromide doped with cerium, $LaBr_3(Ce)$; lanthanum chloride, $LaCl_3$; cesium doped lanthanum chloride, $LaCl_3(Ce)$; lead tungstate, $PbWO_4$; LSO or lutetium oxyorthosilicate $(Lu_2SiO_5)$; LYSO, $Lu_{1.8}Y_{0.2}SiO_5(Ce)$; yttrium aluminum garnet, YAG (Ce); zinc sulfide, ZnS(Ag); and zinc tungstate, $ZnWO_4$.

In one embodiment, a tomogram or an individual tomogram section image is collected at about the same time as cancer therapy occurs using the charged particle beam system 100. For example, a tomogram is collected and cancer therapy is subsequently performed: without the patient moving from the positioning systems, such as in a semi-vertical partial immobilization system, a sitting partial immobilization system, or the a laying position. In a second example, an individual tomogram slice is collected using a first cycle of the accelerator 130 and using a following cycle of the accelerator 130, the tumor 220 is irradiated, such as within about 1, 2, 5, 10, 15 or 30 seconds. In a third case, about 2, 3, 4, or 5 tomogram slices are collected using 1, 2, 3, 4, or more rotation positions of the patient 230 within about 5, 10, 15, 30, or 60 seconds of subsequent tumor irradiation therapy.

In another embodiment, the independent control of the tomographic imaging process and X-ray collection process allows simultaneous single and/or multi-field collection of X-ray images and tomographic images easing interpretation of multiple images. Indeed, the X-ray and tomographic images are optionally overlaid and/or integrated to from a hybrid X-ray/proton beam tomographic image as the patient 230 is optionally in the same position for each image.

In still another embodiment, the tomogram is collected with the patient 230 in the about the same position as when the patient's tumor is treated using subsequent irradiation therapy. For some tumors, the patient being positioned in the same upright or semi-upright position allows the tumor 220 to be separated from surrounding organs or tissue of the patient 230 better than in a laying position. Positioning of the scintillation material, in the scintillation detector system 210, behind the patient 230 allows the tomographic imaging to occur while the patient is in the same upright or semi-upright position.

The use of common elements in the tomographic imaging and in the charged particle cancer therapy allows benefits of the cancer therapy, described supra, to optionally be used with the tomographic imaging, such as proton beam x-axis control, proton beam y-axis control, control of proton beam energy, control of proton beam intensity, timing control of beam delivery to the patient, rotation control of the patient, and control of patient translation all in a raster beam mode of proton energy delivery. The use of a single proton or cation beamline for both imaging and treatment eases patient setup, reduces alignment uncertainties, reduces beam state uncertainties, and eases quality assurance.

In yet still another embodiment, initially a three-dimensional tomographic X-ray and/or proton based reference image is collected, such as with hundreds of individual rotation images of the tumor 220 and patient 230. Subsequently, just prior to proton treatment of the cancer, just a few 2-dimensional control tomographic images of the patient are collected, such as with a stationary patient or at just a few rotation positions, such as an image straight on to the patient, with the patient rotated about 45 degrees each way, and/or the X-ray source and/or patient rotated about 90 degrees each way about the y-axis. The individual control images are compared with the 3-dimensional reference image. An adaptive proton therapy is optionally subsequently performed where: (1) the proton cancer therapy is not used for a given position based on the differences between the 3-dimensional reference image and one or more of the 2-dimensional control images and/or (2) the proton cancer therapy is modified in real time based on the differences between the 3-dimensional reference image and one or more of the 2-dimensional control images.

Charged Particle State Determination/Verification/Photonic Monitoring

Still referring to FIG. 2, the tomography system 200 is optionally used with a charged particle beam state determination system 250, optionally used as a charged particle verification system. The charged particle state determination system 250 optionally measures, determines, and/or verifies one of more of: (1) position of the charged particle beam, such as a treatment beam 269, (2) direction of the treatment beam 269, (3) intensity of the treatment beam 269, (4) energy of the treatment beam 269, (5) position, direction, intensity, and/or energy of the charged particle beam, such as a residual charged particle beam 267 after passing through a sample or the patient 230, and/or (6) a history of the charged particle beam.

Figure 4A:
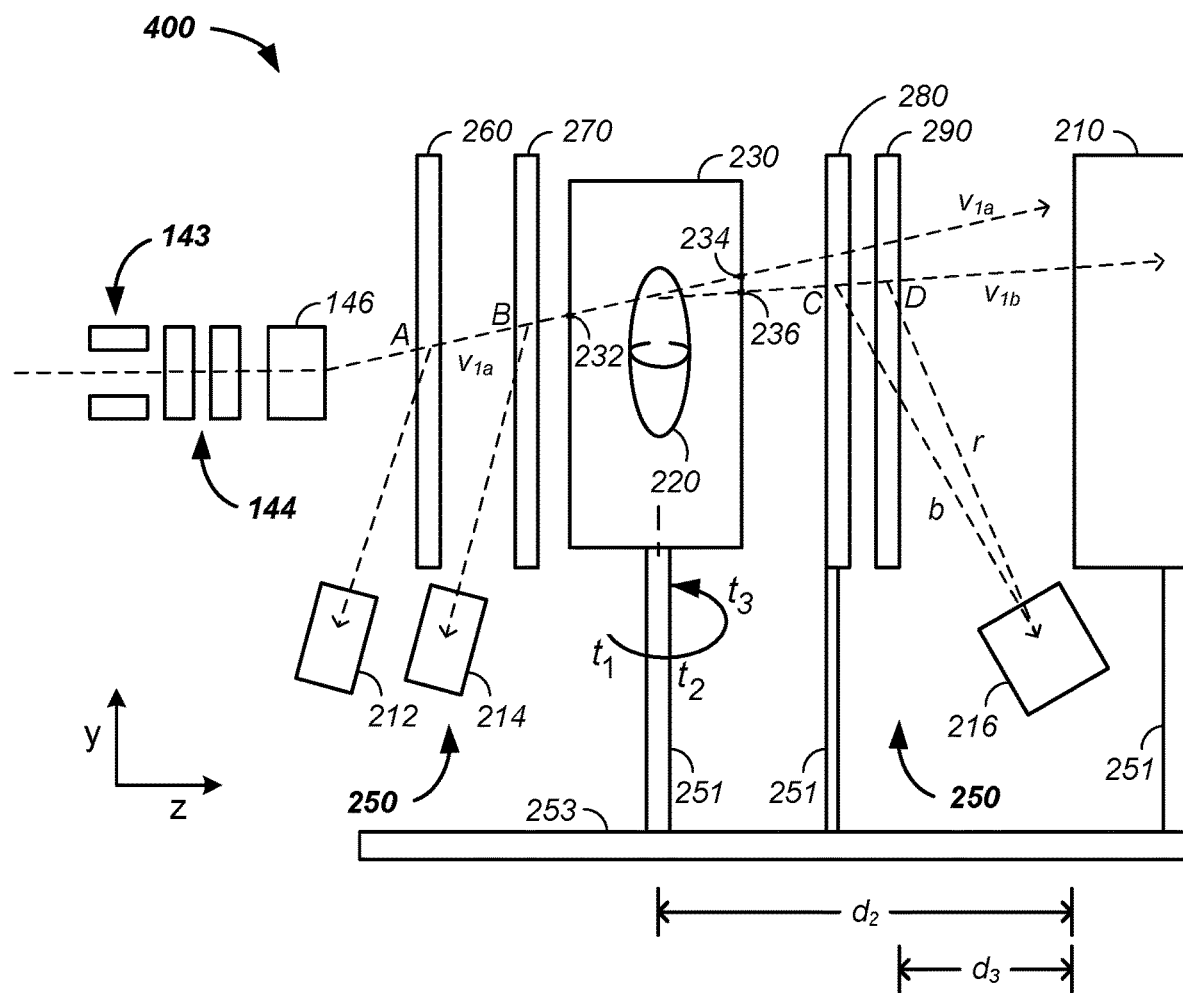
FIG. 4A illustrates a beam path identification system coupled to a beam transport system and a tomography scintillation detector.
Figure 4B:
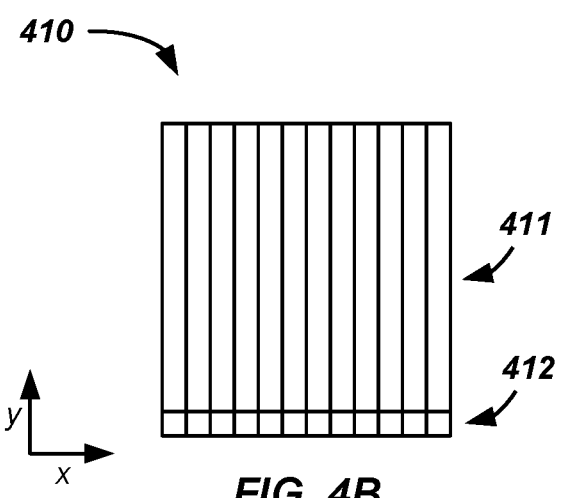
FIG. 4B illustrates an x-axis ionization strip detector.
Figure 4C:
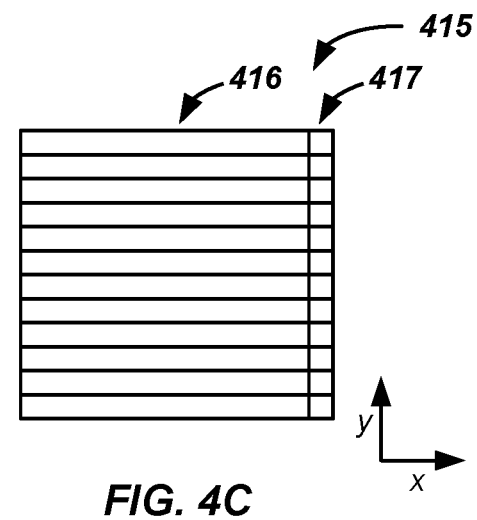
FIG. 4C illustrates a y-axis ionization strip detector.

For clarity of presentation and without loss of generality, a description of the charged particle beam state determination system 250 is described and illustrated separately in FIG. 3 and FIG. 4A; however, as described herein elements of the charged particle beam state determination system 250 are optionally and preferably integrated into the nozzle system 146 and/or the tomography system 200 of the charged particle treatment system 100. More particularly, any element of the charged particle beam state determination system 250 is integrated into the nozzle system 146, a dynamic gantry nozzle, and/or tomography system 200. The tomography system detects secondary electrons, resultant from the positively charged particles, and/or uses a scintillation material of a scintillation detector element 205, scintillation plate, or scintillation detector system 210. The nozzle system 146 or the dynamic gantry nozzle provides an outlet of the charged particle beam from the vacuum tube initiating at the injection system 120 and passing through the synchrotron 130 and beam transport system 135. Any plate, tracking plane, sheet, fluorophore, or detector of the charged particle beam state determination system is optionally integrated into the nozzle system 146. For example, an exit foil of the nozzle is optionally a first sheet 252 of the charged particle beam state determination system 250 and a first coating 254 is optionally coated onto the exit foil, as illustrated in FIG. 2. Similarly, optionally a surface of the scintillation material is a support surface for a fourth coating 292, as illustrated in FIG. 2. The charged particle beam state determination system 250 is further described, infra.

Referring now to FIG. 2, FIG. 3, and FIG. 4A, four tracking planes and/or four sheets, such as a first tracking plane 260 or a first sheet 252, a second tracking plane 270 or second sheet, a third tracking plane 280 or third sheet, and a fourth tracking plane 290 or fourth sheet are used to illustrate detection sheets and/or photon emitting sheets upon transmittance of a charged particle beam. Each sheet is optionally coated with a photon emitter, such as a fluorophore, such as the first sheet 252 is optionally coated with a first coating 254. Without loss of generality and for clarity of presentation, the four tracking planes are each illustrated as units, where the light emitting layer is not illustrated. Thus, for example, the second tracking plane 270 optionally refers to a support sheet, a light emitting sheet, and/or a support sheet coated by a light emitting element. The four tracking planes are representative of n tracking planes, where n is a positive integer.

Referring now to FIG. 2 and FIG. 3, the charged particle beam state verification system 250 is a system that allows for monitoring of the actual charged particle beam position in real-time without destruction of the charged particle beam. The charged particle beam state verification system 250 preferably includes a first position element or first beam verification layer, which is also referred to herein as a coating, luminescent, fluorescent, phosphorescent, radiance, or viewing layer. The first position element optionally and preferably includes a coating or thin layer substantially in contact with a sheet, such as an inside surface of the nozzle foil, where the inside surface is on the synchrotron side of the nozzle foil. Less preferably, the verification layer or coating layer is substantially in contact with an outer surface of the nozzle foil, where the outer surface is on the patient treatment side of the nozzle foil. Preferably, the nozzle foil provides a substrate surface for coating by the coating layer. Optionally, a binding layer is located between the coating layer and the nozzle foil, substrate, or support sheet. Optionally, the position element is placed anywhere in the charged particle beam path. Optionally, more than one position element on more than one sheet, respectively, is used in the charged particle beam path and is used to determine a state property of the charged particle beam, as described infra.

Still referring to FIG. 2 and FIG. 3, the coating, referred to as a fluorophore, yields a measurable spectroscopic response, spatially viewable by a detector or camera, as a result of transmission by the proton beam. The coating is preferably a phosphor, but is optionally any material that is viewable or imaged by a detector where the material changes, as viewed spectroscopically, as a result of the charged particle beam hitting or transmitting through the coating or coating layer. A detector or camera views secondary photons emitted from the coating layer and determines a position of a treatment beam 269, which is also referred to as a current position of the charged particle beam or final treatment vector of the charged particle beam, by the spectroscopic differences resulting from protons and/or charged particle beam passing through the coating layer. For example, the camera views a surface of the coating surface as the proton beam or positively charged cation beam is being scanned by the first axis controller 143, vertical control, and the second axis controller 144, horizontal control, beam position control elements during treatment of the tumor 220. The camera views the current position of the charged particle beam or treatment beam 269 as measured by spectroscopic response. The coating layer is preferably a phosphor or luminescent material that glows and/or emits photons for a short period of time, such as less than 5 seconds for a 50% intensity, as a result of excitation by the charged particle beam. The detector observes the temperature change and/or observe photons emitted from the charged particle beam traversed spot. Optionally, a plurality of cameras or detectors are used, where each detector views all or a portion of the coating layer. For example, two detectors are used where a first detector views a first half of the coating layer and the second detector views a second half of the coating layer. Preferably, at least a portion of the detector is mounted into the nozzle system to view the proton beam position after passing through the first axis and second axis controllers 143, 144. Preferably, the coating layer is positioned in the proton beam path 268 in a position prior to the protons striking the patient 230.

Figure 5:
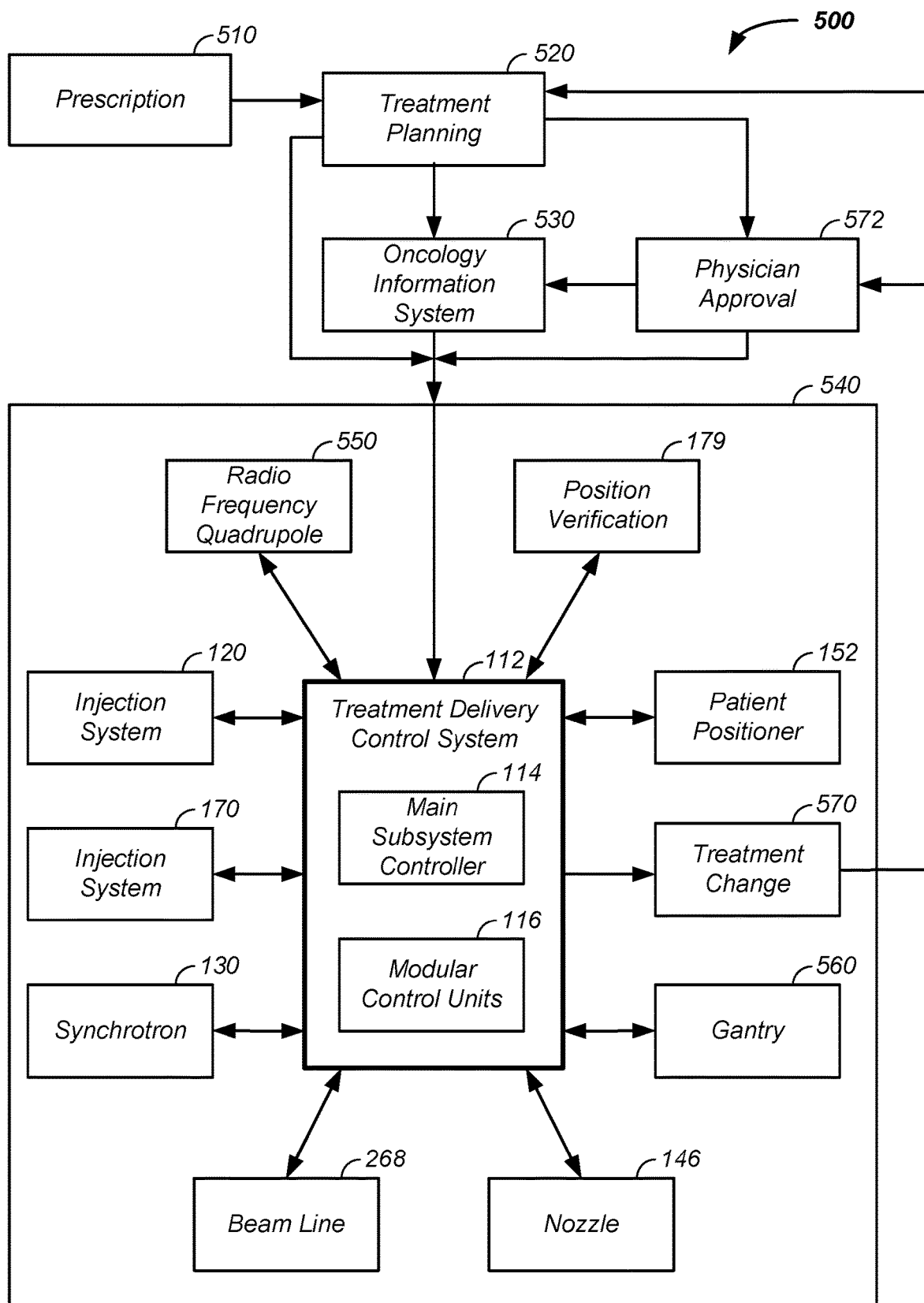
FIG. 5 illustrates a treatment delivery control system.

Referring now to FIG. 1 and FIG. 2, the main controller 110, connected to the camera or detector output, optionally and preferably compares the final proton beam position or position of the treatment beam 269 with the planned proton beam position and/or a calibration reference, such as a calibrated beamline, to determine if the actual proton beam position or position of the treatment beam 269 is within tolerance. The charged particle beam state determination system 250 preferably is used in one or more phases, such as a calibration phase, a mapping phase, a beam position verification phase, a treatment phase, and a treatment plan modification phase. The calibration phase is used to correlate, as a function of x-, y-position of the first axis controller 143 and the second axis controller 144 response the actual x-, y-position of the proton beam at the patient interface. During the treatment phase, the charged particle beam position is monitored and compared to the calibration and/or treatment plan to verify accurate proton delivery to the tumor 220 and/or as a charged particle beam shutoff safety indicator. Referring now to FIG. 5, a position verification system 179 and/or a treatment delivery control system 112, upon determination of a tumor shift, an unpredicted tumor distortion upon treatment, and/or a treatment anomaly optionally generates and or provides a recommended treatment change 1070. The treatment change 1070 is optionally sent out while the patient 230 is still in the treatment position, such as to a proximate physician, through a communication system to a remote physician located outside of the treatment room and not in a direct line of sight of the patient in the treatment position, such as no line of sight through a window between a control room and the patient in the treatment room, and/or over the internet to a remote physician, for physician approval 1072, receipt of which allows continuation of the now modified and approved treatment plan.

Example I

Referring now to FIG. 2, a first example of the charged particle beam state determination system 250 is illustrated using two cation induced signal generation surfaces, referred to herein as the first sheet 252 and a third tracking plane 780. Each sheet is described below.

Still referring to FIG. 2, in the first example, the optional first sheet 252, located in the charged particle beam path prior to the patient 230, is coated with a first fluorophore coating 254, wherein a cation, such as in the charged particle beam, transmitting through the first sheet 252 excites localized fluorophores of the first fluorophore coating 254 with resultant emission of one or more photons. In this example, a first detector 212 images the first fluorophore coating 254 and the main controller 110 determines a current position of the charged particle beam using the image of the fluorophore coating 254 and the detected photon(s). The intensity of the detected photons emitted from the first fluorophore coating 254 is optionally used to determine the intensity of the charged particle beam used in treatment of the tumor 220 or detected by the tomography system 200 in generation of a tomogram and/or tomographic image of the tumor 220 of the patient 230. Thus, a first position and/or a first intensity of the charged particle beam is determined using the position and/or intensity of the emitted photons, respectively.

Still referring to FIG. 2, in the first example, the optional third tracking plane 280, positioned posterior to the patient 230, is optionally a cation induced photon emitting sheet as described in the previous paragraph. However, as illustrated, the third tracking plane 280 is a solid state beam detection surface, such as a detector array. For instance, the detector array is optionally a charge coupled device, a charge induced device, CMOS, or camera detector where elements of the detector array are read directly, as does a commercial camera, without the secondary emission of photons. Similar to the detection described for the first sheet, the third tracking plane 280 is used to determine a position of the charged particle beam and/or an intensity of the charged particle beam using signal position and/or signal intensity from the detector array, respectively.

Still referring to FIG. 2, in the first example, signals from the first sheet 252 and third tracking plane 280 yield a position before and after the patient 230 allowing a more accurate determination of the charged particle beam through the patient 230 therebetween. Optionally, knowledge of the charged particle beam path in the targeting/delivery system 140, such as determined via a first magnetic field strength across the first axis controller 143 or a second magnetic field strength across the second axis controller 144 is combined with signal derived from the first sheet 252 to yield a first vector of the charged particles prior to entering the patient 230 and/or an input point of the charged particle beam into the patient 230, which also aids in: (1) controlling, monitoring, and/or recording tumor treatment and/or (2) tomography development/interpretation. Optionally, signal derived from use of the third tracking plane 280, posterior to the patient 230, is combined with signal derived from tomography system 200, such as the scintillation detector system 210, to yield a second vector of the charged particles posterior to the patient 230 and/or an output point of the charged particle beam from the patient 230, which also aids in: (1) controlling, monitoring, deciphering, and/or (2) interpreting a tomogram or a tomographic image.

For clarity of presentation and without loss of generality, detection of photons emitted from tracking planes is used to further describe the charged particle beam state determination system 250. However, any of the cation induced photon emission detection planes described herein are alternatively detector arrays. Further, any number of cation induced photon emission tracking planes or sheets are used prior to the patient 230 and/or posterior to the patient 230, such a 1, 2, 3, 4, 6, 8, 10, or more. Still further, any of the cation induced photon emission sheets are place anywhere in the charged particle beam, such as in the synchrotron 130, in the beam transport system 135, in the targeting/delivery system 140, the nozzle system 146, in the treatment room, and/or in the tomography system 200. Any of the cation induced photon emission sheets are used in generation of a beam state signal as a function of time, which is optionally recorded, such as for an accurate history of treatment of the tumor 220 of the patient 230 and/or for aiding generation of a tomographic image. Further, and of the tracking planes or sheets optionally detect secondary electrons, resultant from passage of the charged particle beam, with or without emission of photons.

Example II

Referring now to FIG. 3, a second example of the charged particle beam state determination system 250 is illustrated using three cation induced signal generation surfaces, referred to herein as the second tracking plane 270, the third tracking plane 280, and the fourth sheet 290. Any of the second tracking plane 270, the third tracking plane 280, and the fourth tracking plane 290 contain any of the features of the sheets described supra.

Still referring to FIG. 3, in the second example, the second tracking plane 270, positioned prior to the patient 230, is optionally integrated into the nozzle and/or the nozzle system 146, but is illustrated as a separate sheet. Signal derived from the second tracking plane 270, such as at point A, is optionally combined with signal from the first sheet 252 and/or state of the targeting/delivery system 140 to yield a first line or vector, $v_{1a}$, from point A to point B of the charged particle beam prior to the sample or patient 230 at a first time, $t_1$, and a second line or vector, $v_{2a}$ from point F to point G of the charged particle beam prior to the sample at a second time, $t_2$.

Still referring to FIG. 3, in the second example, the third tracking plane 280 and the fourth tracking plane 290, positioned posterior to the patient 230, are optionally integrated into the tomography system 200, but are illustrated as a separate sheets. Signal derived from the third tracking plane 280, such as at point D, is optionally combined with signal from the fourth tracking plane 290 and/or signal from the tomography system 200 to yield a first line segment or vector, $v_{1b}$, from point $C_2$ to point D and/or from point D to point E of the charged particle beam posterior to the patient 230 at the first time, $t_1$, and a second line segment or vector, $v_{2b}$, such as from point H to point I of the charged particle beam posterior to the sample at a second time, $t_2$. Signal derived from the third tracking plane 280 and/or from the fourth tracking plane 290 and the corresponding first vector at the second time, $t_2$, is used to determine an output point, $C_2$, which may and often does differ from an extension of the first vector, $v_{1a}$, from point A to point B through the patient to a non-scattered beam path of point $C_1$. The difference between point $C_1$ and point $C_2$ and/or an angle, α, between the first vector at the first time, $v_{1a}$, and the first vector at the second time, $v_{1b}$, is used to determine/map/identify, such as via tomographic analysis, internal structure of the patient 230, sample, and/or the tumor 220, especially when combined with scanning the charged particle beam in the x/y-plane as a function of time, such as illustrated by the second vector at the first time, $v_{2a}$, and the second vector at the second time, $v_{2b}$, forming angle β and/or with rotation of the patient 230, such as about the y-axis, as a function of time.

Still referring to FIG. 3, multiple detectors/detector arrays are illustrated for detection of signals from multiple sheets, respectively. However, a single detector/detector array is optionally used to detect signals from multiple sheets, as further described infra. As illustrated, a set of detectors 211 is illustrated, including a second detector 214 imaging the second tracking plane 270, a third detector 216 imaging the third tracking plane 280, and a fourth detector 218 imaging the fourth tracking plane 290. Any of the detectors described herein are optionally detector arrays, are optionally coupled with any optical filter, and/or optionally use one or more intervening optics to image any of the four tracking planes 252, 270, 280, 290 or tracking sheets. Further, two or more detectors optionally image a single sheet, such as a region of the sheet, to aid optical coupling, such as F-number optical coupling.

Still referring to FIG. 3, a vector or line segment of the charged particle beam is determined. Particularly, in the illustrated example, the third detector 216, determines, via detection of secondary emitted photons, that the charged particle beam transmitted through point D and the fourth detector 218 determines that the charged particle beam transmitted through point E, where points D and E are used to determine the first vector or line segment at the second time, $v_{1b}$, as described supra. To increase accuracy and precision of a determined vector of the charged particle beam, a first determined beam position and a second determined beam position are optionally and preferably separated by a distance, $d_1$, such as greater than 0.1, 0.5, 1, 2, 3, 5, 10, or more centimeters. A support element 252 is illustrated that optionally connects any two or more elements of the charged particle beam state determination system 250 to each other and/or to any element of the charged particle beam system 100, such as a rotating platform 256 used to position and/or co-rotate the patient 230 and any element of the tomography system 200.

Example III

Still referring to FIG. 4A, a third example of the charged particle beam state determination system 250 is illustrated in an integrated tomography-cancer therapy system 400.

Referring to FIG. 4A, multiple tracking planes and/or sheets and multiple detectors are illustrated determining a charged particle beam state prior to the patient 230. As illustrated, a first camera 212 spatially images photons emitted from a first tracking plane 260 or first sheet at point A, resultant from energy transfer from the passing charged particle beam, to yield a first signal and a second camera 214 spatially images photons emitted from the second tracking plane 270 at point B, resultant from energy transfer from the passing charged particle beam, to yield a second signal. The first and second signals allow calculation of the first vector or line segment, $v_{1a}$, with a subsequent determination of an entry point 232 of the charged particle beam into the patient 230. Determination of the first vector, $v_{1a}$, is optionally supplemented with information derived from states of the magnetic fields about the first axis controller 143, the vertical control, and the second axis controller 144, the horizontal axis control, as described supra.

Still referring to FIG. 4A, the charged particle beam state determination system is illustrated with multiple resolvable wavelengths of light emitted as a result of the charged particle beam transmitting through more than one molecule type, light emission center, and/or fluorophore type. For clarity of presentation and without loss of generality a first fluorophore in the third tracking plane 280 is illustrated as emitting blue light, b, and a second fluorophore in the fourth tracking plane 290 is illustrated as emitting red light, r, that are both detected by the third detector 216. The third detector is optionally coupled with any wavelength separation device, such as an optical filter, grating, or Fourier transform device. For clarity of presentation, the system is described with the red light passing through a red transmission filter blocking blue light and the blue light passing through a blue transmission filter blocking red light. Wavelength separation, using any means, allows one detector to detect a position of the charged particle beam resultant in a first secondary emission at a first wavelength, such as at point C, and a second secondary emission at a second wavelength, such as at point D. By extension, with appropriate optics, one camera is optionally used to image multiple sheets and/or sheets both prior to and posterior to the sample. Spatial determination of origin of the red light and the blue light allow calculation of the first vector at the second time, $v_{1b}$, and an actual exit point 236 from the patient 230 as compared to a non-scattered exit point 234 from the patient 230 as determined from the first vector at the first time, $v_{1a}$.

Ion Beam State Determination/Energy Dissipation System

Referring now to FIG. 4B-4H an ion beam state determination/kinetic energy dissipation system is described. Generally, a dual use chamber is described functioning at a first time, when filled with gas, as an element in an ion beam state determination system and functioning at a second time, when filled with liquid, as an element of a kinetic energy dissipation system. The dual purpose/use chamber is further described herein.

Ionization Strip Detector

Referring now to FIGS. 4(A-C), an ion beam location determination system is described. In FIG. 4A, x/y-beam positions are determined using the first tracking plane 260 and the second tracking plane 270, such as where the sheets emit photons. In FIG. 4B, the first tracking plane 260 or first sheet comprises a first axis, or x-axis, ionization strip detector 410. In the first ionization strip detector 410, an x-axis position of the positive ion beam is determined using vertical strips, where interaction of the positive ion with one or more vertical strips of the x-axis interacting strips 411 results in electron emission, the current carried by the interacting strip and converted to an x-axis position signal, such as with an x-axis register 412, detector, integrator, and/or amplifier. Similarly, in the second ionization strip detector 415, a y-axis position of the positive ion beam is determined using horizontal strips, where interaction of the positive ion results with one or more horizontal strips of the y-axis ionization strips 416 results in another electron emission, the resulting current carried by the y-axis interacting strip and converted to a y-axis position signal, such as with a y-axis register 417, detector, integrator, and/or amplifier.

Dual Use Ion Chamber

Figure 4D:
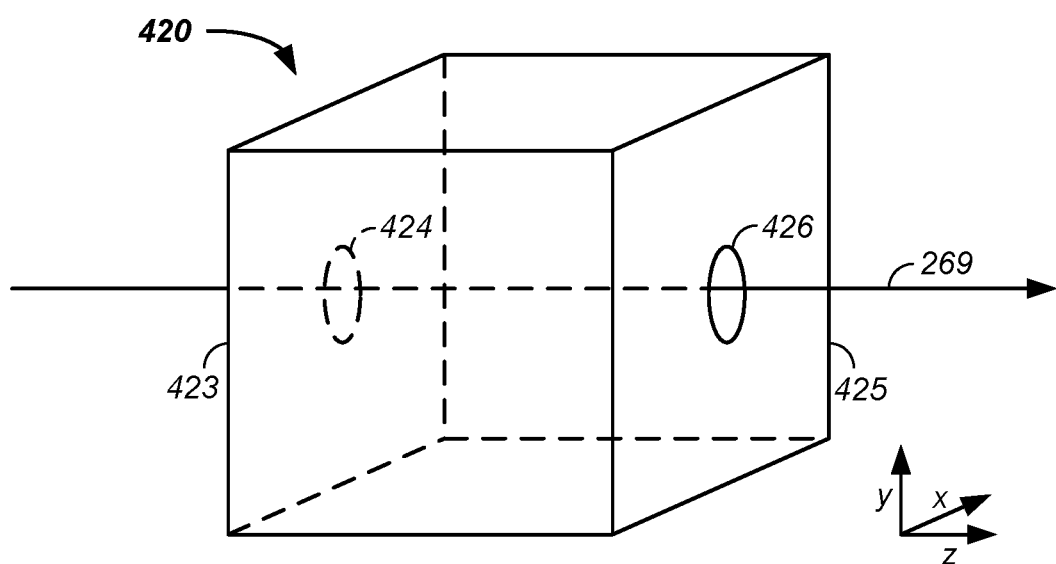
FIG. 4D illustrates a kinetic energy dissipation chamber.

Referring now to FIG. 4D a dual use ionization chamber 420 is illustrated. The dual use ionization chamber 420 is optionally positioned anywhere in an ion beam path, in a negatively charged particle beam path, and/or in a positively charged particle beam path, where the positively charged particle beam path is used herein for clarity of presentation. Herein, for clarity of presentation and without loss of generality, the dual use ionization chamber 420 is integrated into and/or is adjacent the nozzle system 146. The dual use ionization chamber 420 comprises any material, but is optionally and preferably a plastic, polymer, polycarbonate, and/or an acrylic. The dual use ionization chamber 420 comprises: a charged particle beam entrance side 423 and a charged particle beam exit side 425. The positively charged particle beam path optionally and preferably passes through an entrance aperture 424 in the beam entrance side of the dual use ionization chamber 420 and exits the dual use ionization chamber 420 through an exit aperture 426 in the charged particle beam exit side 425. The entrance aperture 424 and/or the exit aperture 426 are optionally covered with a liquid tight and/or gas tight optic or film, such as a window, glass, optical cell surface, film, membrane, a polyimide film, an aluminum coated film, and/or an aluminum coated polyimide film.

Example I

Figure 4E:
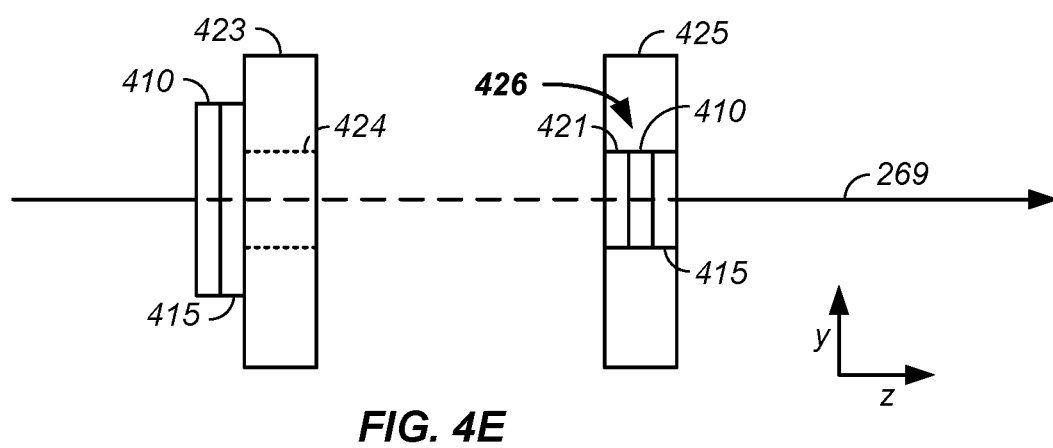
FIG. 4E illustrates ionization strips integrated with the kinetic energy dissipation chamber.

In a first example, referring now to FIG. 4D and FIG. 4E, the entrance aperture 424 and exit aperture 426 of the charged particle beam entrance side 423 and the charged particle beam exit side 425, respectively, of the dual use ionization chamber 420 are further described. More particularly, the first ionization strip detector 410 and the second ionization strip detector 415 are coupled with the dual use ionization chamber 420. As illustrated, the first ionization strip detector 410 and the second ionization strip detector 415 cover the entrance aperture 424 and optionally and preferably form a liquid and/or gas tight seal to the entrance side 423 of the dual use ionization chamber 420.

Example II

In a second example, referring still to FIG. 4D and FIG. 4E, the entrance aperture 424 and exit aperture 426 of the charged particle beam entrance side 423 and the charged particle beam exit side 425, respectively, of the dual use ionization chamber 420 are further described. More particularly, in this example, the first ionization strip detector 410 and the second ionization strip detector 415 are integrated into the exit aperture 426 of the use ionization chamber 420. As illustrated, an aluminum coated film 421 is also integrated into the exit aperture 426.

Example III

In a third example, referring still to FIG. 4D and FIG. 4E, the first ionization detector 410 and the second ionization detector 415 are optionally used to: (1) cover and/or function as an element of a seal of the entrance aperture 424 and/or the exit aperture 426 and/or (2) function to determine a position and/or state of the positively charged ion beam at and/or near one or both of the entrance aperture 424 and the exit aperture 426 of the dual use ionization chamber 420.

Figure 4F:
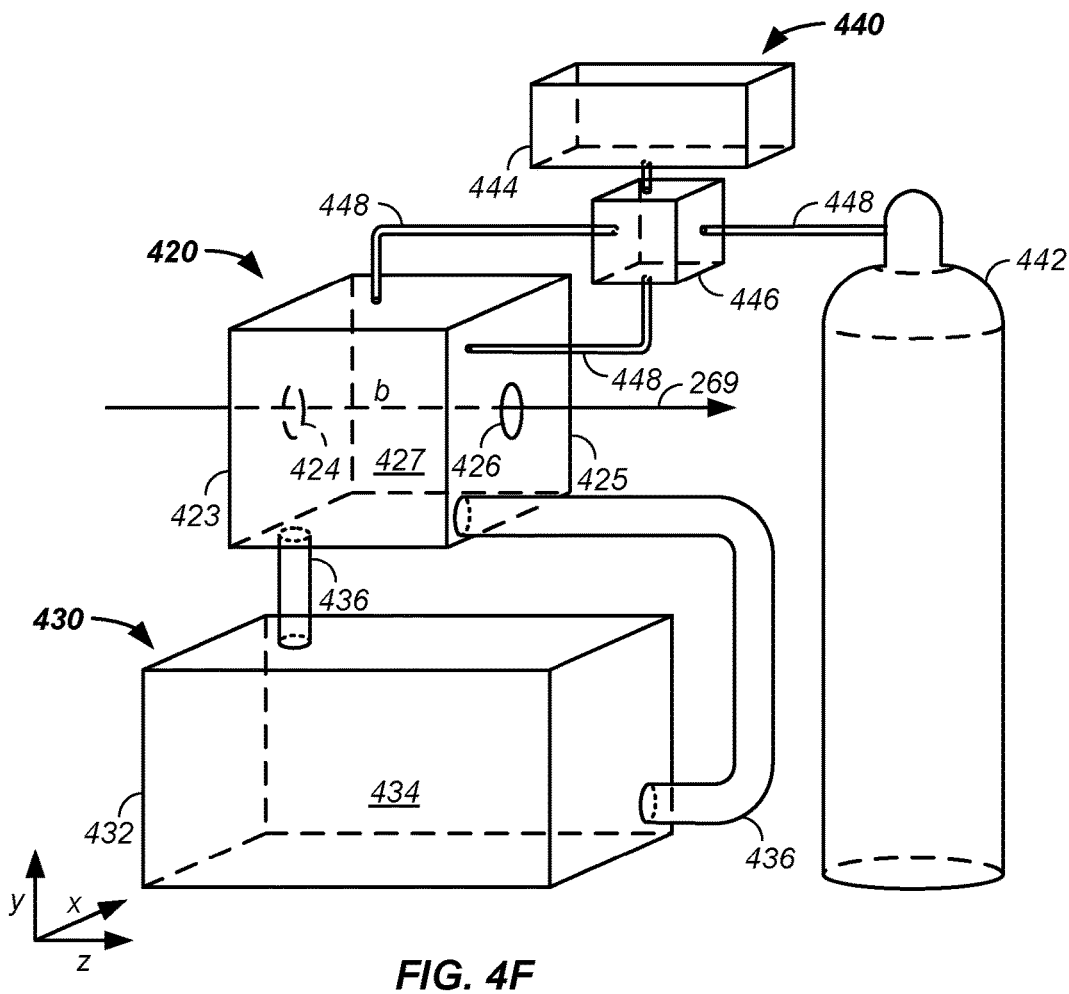
FIG. 4F illustrates an alternating kinetic energy dissipation chamber-targeting chamber.

Referring now to FIG. 4F, two uses of the dual use ionization chamber 420 are described. At a first time, the dual use ionization chamber 420 is filled, at least to above a path of the charged particle beam, with a liquid. The liquid is used to reduce and/or dissipate the kinetic energy of the positively charged particle beam. At a second time, the dual use ionization chamber 420 is filled, at least in a volume of the charged particle beam, with a gas. The gas, such as helium, functions to maintain the charged particle beam integrity, focus, state, and/or dimensions as the helium scatters the positively charged particle beam less than air, where the pathlength of the dual use ionization chamber 420 is necessary to separate elements of the nozzle system, such as the first axis controller 143, the second axis controller 144, the first tracking plane 260, the second tracking plane 270, the third tracking plane 280, the fourth tracking plane 290, and/or one or more instances of the first ionization detector 410 and the second ionization detector 415.

Kinetic Energy Dissipator

Referring still to FIG. 4F, the kinetic energy dissipation aspect of the dual use ionization chamber 420 is further described. At a first time, a liquid, such as water is moved, such as with a pump, into the dual use ionization chamber 420. The water interacts with the proton beam to slow and/or stop the proton beam. At a second time, the liquid is removed, such as with a pump and/or drain, from the dual use ionization chamber 420. Through use of more water than will fit into the dual use ionization chamber 420, the radiation level of the irradiated water per unit volume is decreased. The decreased radiation level allows more rapid access to the ionization chamber, which is very useful for maintenance and even routine use of a high power proton beam cancer therapy system. The inventor notes that immediate access to the chamber is allowed versus a standard and mandatory five hour delay to allow radiation dissipation using a traditional solid phase proton beam energy reducer.

Example I

Still referring to FIG. 4F, an example of use of a liquid movement/exchange system 430 is provided, where the liquid exchange system 430 is used to dissipate kinetic energy and/or to disperse radiation. Generally, the liquid exchange system moves water from the use purpose ionization chamber 420, having a first volume 427, using one or more water lines 436, to a liquid reservoir tank 432 having a second volume 434. Generally, any radiation build-up in the first volume 427 is diluted by circulating water through the water lines 436 to the second volume 434, where the second volume is at least 0.25, 0.5, 1, 2, 3, 5, or 10 times the size of the first volume. As illustrated, more than one drain line is attached to the dual use ionization chamber 420, which allows the dual use ionization chamber 420 to drain regardless of orientation of the nozzle system 146 as the dual use ionization chamber 420 optionally and preferably co-moves with the nozzle system 146 and/or is integrated into the nozzle system 146. Optionally, the liquid movement/exchange system 430 is used to remove radiation from the treatment room 922, to reduce radiation levels of discharged fluids to acceptable levels via dilution, and/or to move the temporarily radioactive fluid to another area or room for later reuse in the liquid movement/exchange system 430.

Example II

Still referring to FIG. 4F, an example of a gas movement/exchange system 440 is provided, where the gas exchange system 440 is used to fill/empty gas, such as helium, from the dual use ionization chamber 420. As illustrated, helium, from a pressurized helium tank 442 and/or a helium displacement chamber 444, is moved, such as via a regulator 446 or pump and/or via displacement by water, to/from the dual use ionization chamber 420 using one or more gas lines. For instance, as water is pumped into the dual use ionization chamber 420 from the liquid reservoir tank 432, the water displaces the helium forcing the helium back into the helium displacement chamber 444. Alternatingly, the helium is moved back into the dual use ionization chamber 420 by draining the water, as described supra, and/or by increasing the helium pressure, such as through use of the pressurized helium tank 442. A desiccator is optionally used in the system.

It should be appreciated that the gas/liquid reservoirs, movement lines, connections, and pumps are illustrative in nature of any liquid movement system and/or any gas movement system. Further, the water, used in the examples for clarity of presentation, is more generally any liquid, combination of liquids, hydrocarbon, mercury, and/or liquid bromide. Similarly, the helium, used in the examples for clarity of presentation, is more generally any gas, mixture of gases, neon, and/or nitrogen.

Generally, the liquid in the liquid exchange system 430, replaces graphite, copper, or metal used as a kinetic energy reducer in the cancer therapy system 100. Still more generally, the liquid exchange system 420 is optionally used with any positive particle beam type, any negative particle beam type, and/or with any accelerator type, such as a cyclotron or a synchrotron, to reduce kinetic energy of the ion beam while diluting and/or removing radiation from the system.

Beam Energy Reduction

Figure 4G:
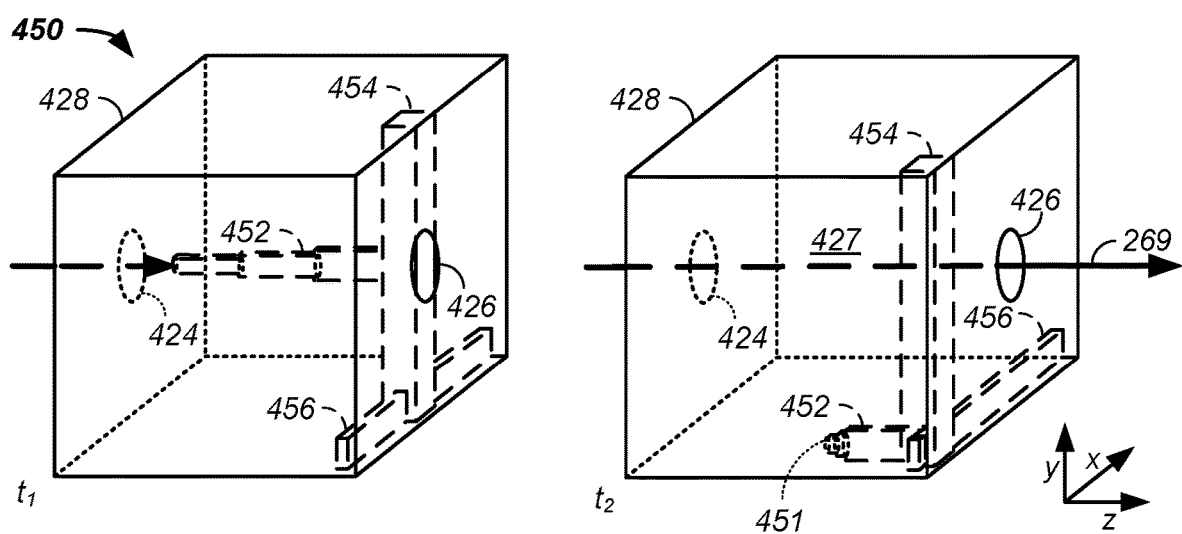
FIG. 4G illustrates a beam mapping chamber.
Figure 4H:
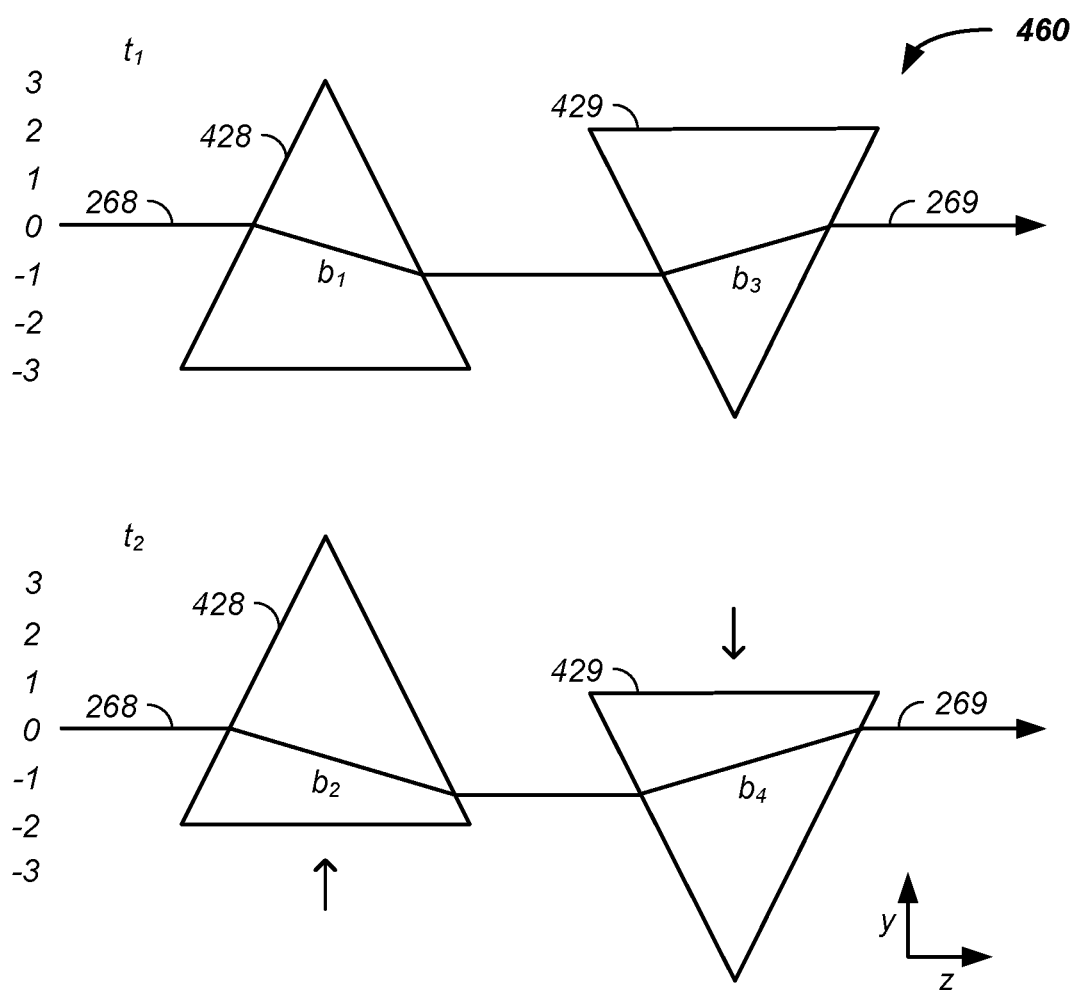
FIG. 4H illustrates beam direction compensating chambers.

Still referring to FIG. 4F and referring now to FIG. 4H, the kinetic energy dissipation aspect of the dual use ionization chamber 420 is further described. A pathlength, b, between the entrance aperture 424 and exit aperture 426, of 55 cm through water is sufficient to block a 330 MeV proton beam, where a 330 MeV proton beam is sufficient for proton transmission tomography through a patient. Thus, smaller pathlengths are optionally used to reduce the energy of the proton beam.

Still referring to FIG. 4F, in a first optional embodiment, a series of liquid cells of differing pathlengths are optionally moved into and out of the proton beam to reduce energy of the proton beam and thus control a depth of penetration into the patient 230. For example, any combination of liquid cells, such as the dual use ionization chamber 420, having pathlengths of 1, 2, 4, 8, 16, or 32 cm or any pathlength from 0.1 to 100 cm are optionally used. Once an energy degradation pathlength is set to establish a main distance into the patient 230, energy controllers of the proton beam are optionally used to scan varying depths into the tumor.

Still referring to FIG. 4F and referring again to FIG. 4H, in a second, preferred, optional embodiment, one or more pathlength adjustable liquid cells, such as the dual use ionization chamber 420, are positioned in the proton beam path to use the proton beam energy to a preferred energy to target a depth of penetration into the patient 230. Two examples are used to further describe the pathlength adjustable liquid cells yielding a continuous variation of proton beam energy.

Example I

A first example of a continuously variable proton beam energy controller 460 is illustrated in FIG. 4H. It should be appreciated that a first triangular cross-section is used to represent the dual use ionization chamber 420 for clarity of presentation and without loss of generality. More generally, any cross-section, continuous and/or discontinuous as a function of x/y-axis position, is optionally used. Here, a continuous function, pathlength variable with x- and/or y-axis movement first liquid cell 428 comprises a triangular cross-section. As illustrated, at a first time, $t_1$, the proton beam path 268 has a first pathlength, $b_1$, through the first liquid cell 428. At a second time, after translation of the first liquid cell 428 upward along the y-axis, the proton beam path has a second pathlength, $b_2$, through the first liquid cell 428. Thus, by moving the first liquid cell 428, having a non-uniform thickness, the proton beam path 268 passes through differing amounts of liquid, yielding a range of kinetic energy dissipation. Simply, a longer pathlength, such as the second pathlength, $b_2$, being longer than the first pathlength, $b_1$, results in a greater slowing of the charged particles in the proton beam path. Herein, an initial pathlength of unit length one is replaced with the second pathlength that is plus-or-minus at least 1, 2, 3, 4, 5, 10, 20, 30, 50, 100, or 200 percent of the first pathlength.

Example II

A second example of a continuously variable proton beam energy controller 460 is illustrated in FIG. 4H. As illustrated, by increasing or decreasing the first pathlength, $b_1$, the resultant proton beam path 268 is possibly offset downward or upward respectively. To correct the proton beam path 268 back to an original vector, such as the treatment beam path 269, a second liquid cell 429 is used. As illustrated: (1) a third pathlength, $b_3$, through the second liquid cell 429 is equal to the first pathlength, $b_1$, at the first time, $t_1$; (2) the sign of the entrance angle of the proton beam path 268 is reversed when entering the second liquid cell 429 compared to entering the first liquid cell 428; and (3) the sign of the exit angle of the proton beam 268 exiting the second liquid cell 429 is opposite the first liquid cell 428. Further, as the first liquid cell 428 is moved in a first direction, such as upward along the y-axis as illustrated, to maintain a fourth pathlength, $b_4$, in the second liquid cell 429 matching the second pathlength, $b_2$, through the first liquid cell 428 at a second time, $t_2$, the second liquid cell 429 is moved in an opposite direction, such as downward along the y-axis. More generally, the second liquid cell 429 optionally: (1) comprises a shape of the first liquid cell 428; (2) is rotated one-hundred eighty degrees relative to the first liquid cell 428; and (3) is translated in an opposite direction of translation of the first liquid cell 428 through the proton beam path 268 as a function of time. Generally, 1, 2, 3, 4, 5, or more liquid cells of any combination of shapes are used to slow the proton beam to a desired energy and direct the resultant proton beam, such as the treatment beam 269 along a chosen vector as a function of time.

Example III

Still referring to FIG. 4F and FIG. 4H, the proton beam, is optionally accelerated to an energy level/speed and, using the variable pathlength dual use ionization chamber 420, the first liquid cell 428, and/or the second liquid cell 429, the energy of the extracted beam is reduced to varying magnitudes, which is a form of scanning the tumor 220, as a function of time. This allows the synchrotron 130 to accelerate the protons to one energy and after extraction control the energy of the proton beam, which allows a more efficient use of the synchrotron 130 as increasing or decreasing the energy with the synchrotron 130 typically results in a beam dump and recharge and/or requires significant time and/or energy, which slows treatment of the cancer while increasing cost of the cancer.

Beam State Determination

Referring now to FIG. 4G, a beam state determination system 450 is described that uses one or more of the first liquid cell 428, the second liquid cell 429, and/or the dual use ionization chamber 420. For clarity of presentation and without loss of generality, as illustrated, the first liquid cell 428 comprises an orthotope shape. The beam state determination system 450 comprises at least a beam sensing element 451 responsive to the proton beam connected to the main controller 110. Optionally and preferably, the beam sensing element 451 is positioned into various x,y,z-positions inside the liquid containing orthotope as a function of time, which allows a mapping of properties of the proton beam, such as: intensity, depth of penetration, energy, radial distribution about an incident vector of the proton beam, and/or a resultant mean angle. As illustrated, the beam sensing element 451 is positioned in the proton beam path at a first time, $t_1$, using a three-dimensional probe positioner, comprising: a telescoping z-axis sensor positioner 452, a y-axis positioning rail 454, and an x-axis positioning rail 456 and is positioned out of the proton beam path at a second time, $t_2$ using the three-dimensional probe positioner. Generally, the probe positioner is any system capable of positioning the beam sensing element 451 as a function of time.

Time of Flight

Presently, many residual energy detectors are based on a scintillator material where the light output is proportional to the proton's energy. For this type of detector, the ion is stopped in the scintillator material, ideally not too close to the surface. In the system described herein, the ion is not necessarily stopped with the time of flight detectors.

Further, residual energy detectors based on a scintillation material requires that the ion have energy in a particular range to ensure that it stops in the scintillator. The energy stopping requirement leads to adjusting energy of the proton beam, which takes time leading to time induced errors, such as patient movement. In the system described herein, the time requiring energy adjustment step is optionally removed.

Referring now to FIGS. 4(I-K), time of flight of positively charged particles passing through the patient 230 is used to determine residual energy/velocity of the positively charged particles, such as for use in positively charged particle tomography. Herein, for clarity of presentation and without loss of generality protons and proton tomography are used to described the positively charged particles and positively charged particle tomography, respectively, where the positively charged particle comprises any atomic number and any positive charge, such as +1, +2, +3, +4, +5, or +6 or charge to mass ratio, such as 1:1 or 2:1.

Herein, time of flight (TOF) refers to the time that the protons need to travel through one or more mediums. Measurement of the time of flight is used to measure a velocity, energy, or pathlength through the one or mediums of the proton.

Herein, the proton is detected directly and/or indirectly, such as via light emission, secondary particle formation, and/or generation of a secondary electron from the interacting material. In the case of higher energy particles, detection of a breakdown particle of the higher energy particles is optionally used to determine path and/or velocity of the higher energy particle.

Figure 4I:
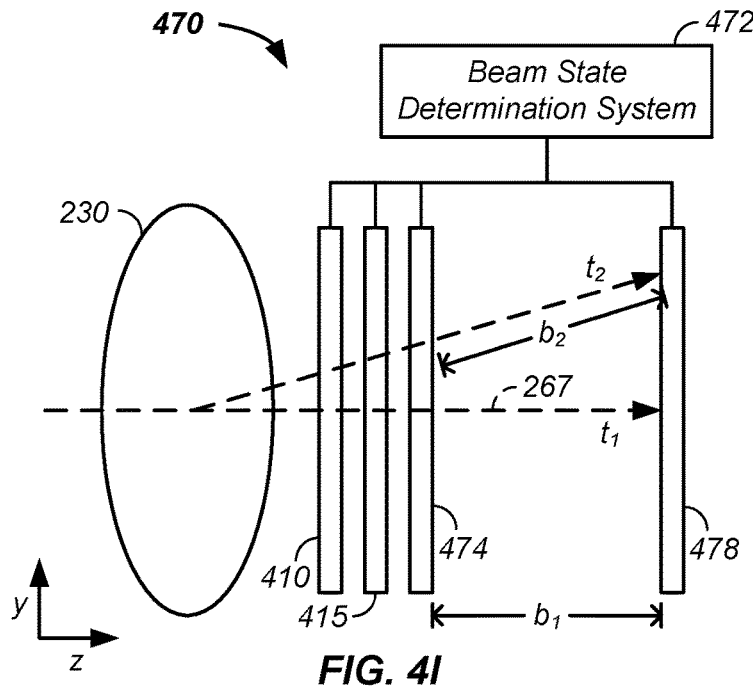
FIG. 4I, FIG. 4J, and FIG. 4K illustrate a beam state determination system.

Referring now to FIG. 4I, a time of flight system 470 is illustrated. In this example, the protons from the synchrotron 130, after passing through the patient 230, forms the residual charged particle beam 267. With or without x/y-position detectors, the velocity or energy of the residual charged particle beam 267 is determined using a first TOF detector 474 and a second TOF detector 478. A pathlength is the distance between a first point of a charged particle, of the charged particle beam 267, crossing the first TOF detector 474 and a second point of the charged particle crossing or stopped in the second TOF detector 478. As illustrated, at a first time, $t_1$, a residual charged particle of the residual charged particle beam 267 between the first TOF detector 474 and the second TOF detector 478 comprises a first pathlength, $b_1$. During use, an initial time of the charged particle crossing the first TOF detector is derived from the first TOF detector 474 and a final time of the charged particle crossing the second TOF detector 478 is derived from the second TOF detector 478. The elapsed time, the time difference between the initial time and the final time, is combined with pathlength to determine the velocity of the residual charged particle beam 267 and/or the energy of the residual charged particle beam 267 as energy is related to velocity for a mass of a given particle, such as through a mathematical relationship between velocity, time, and distance.

Still referring to FIG. 4I, the first TOF detector 474 and the second TOF detector 478 are optionally detector arrays. Thus, a first position of a charged particle of the residual charged particle beam 267 is optionally determined by determining which detector element of the first TOF detector 474 detects the charged particle and a second position of the charged particle is optionally determined by determining which detector element of the second TOF detector 478 detects the charged particle. As illustrated at the second time, $t_2$, the use of detector arrays allows determination of a second pathlength, $b_2$, at a non-orthogonal angle relative to front surface planes of the first and second TOF detectors 474, 478.

Still referring to FIG. 4I, the first TOF detector 474 and the second TOF detector 478 are optionally used in combination with x/y-position detectors of the charged particle, such as the first ionization strip detector 410 and the second ionization strip detector 415 or the third tracking plane 280 and the fourth tracking plane 290, described supra.

Still referring to FIG. 4I, generally a beam state determination system 472, optionally linked to the main controller 110, uses signals from the x/y-position detectors, the first TOF detector 474, and/or the second TOF detector 478 to determine one or more of: two or more x-positions of the charged particle, two or more y-positions of the charged particle, the initial time, the final time, the elapsed time, a velocity of the residual charged particle beam, an energy of the residual charged particle beam 267, an exit point of the charged particle from the patient 230, and input to/calculation of a charged particle tomography image, such as the tumor 220 of the patient 230.

Figure 4J:
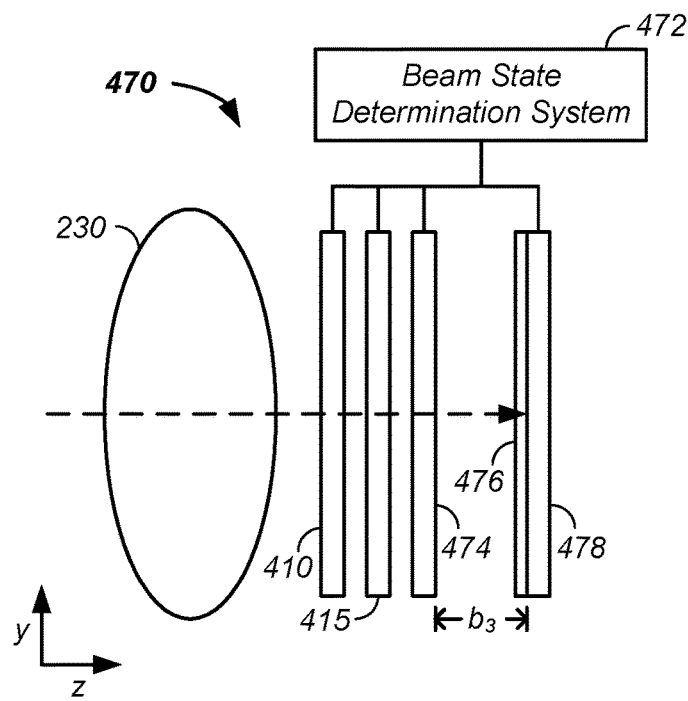

Referring now to FIG. 4J, the time of flight system 470 is illustrated with an optional time of flight degrader 476, also referred to as a time expander element, velocity reducer element, or an energy degrader element. Generally, the velocity of the residual charged particle beam 267 requires determination of sub-microsecond time intervals between the charged particle beam crossing the first TOF detector 474 and the second TOF detector 478, such as less than nanosecond or less than one picosecond. While nanosecond time intervals are readily determined, more advanced systems are required to determine time intervals on the order of 1 to 1,000,000 femtoseconds or 1 to 1000 picoseconds, which may be prohibitively expensive, position sensitive, and/or large. However, insertion of the time of flight degrader 476 into a path of the residual charged particle beam between the patient 230 and the second TOF detector 478 slows the charged particle to allow time intervals, between the first TOF detector 474 and the second time of flight detector 478, greater than 1, 10, 100, or 1,000 nanoseconds. The time of flight degrader optionally decreases velocity of a charged particle by greater than 10, 20, 30, 40, or 50 percent. The time of flight degrader 476 is optionally any material or set of materials and comprises any geometry. Preferably, the time of flight degrader 476 comprises a thin film of: metal or a material consisting essentially of fewer than 12, 10, 7, or 6 protons per atom. Optionally, the time of flight degrader 476 comprises a beryllium or carbon film or a material yielding a secondary emission, such as secondary photons or secondary electrons released from the time of flight degrader 476 upon the residual charged particle beam 267 striking or transmitting through the time of flight degrader 476. Optionally, the second TOF detector 478 detects the secondary emission. As the time of flight degrader 476 potentially redirects the residual charged particle beam 267 and as the absolute deviation increases with z-axis travel of the residual charged particle beam 267, to reduce x/y-position error the time of flight degrader 476 is optionally and preferably positioned proximate, adjacent, within less than 10, 5, 1, or 0.1 mm, and/or in contact with the second TOF detector 478, which results in an accurate determination of x/y-position of the residual charged particle beam 267 for use in determination of the time of flight pathlength and/or an emission point of the residual charged particle beam 267 from the patient 230. Use of the time of flight degrader 476 reduces the first pathlength, $b_1$, to a third pathlength, $b_3$, as illustrated.

Figure 4K:
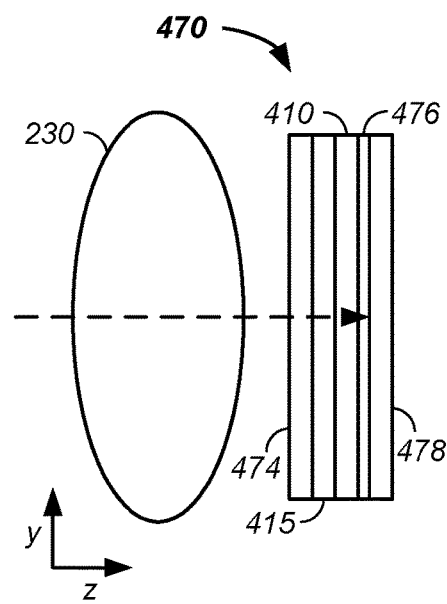

Referring now to FIG. 4K, the time of flight system 470 is illustrated as a solid-state device. In this example, the first TOF detector 474 is positioned closer to the patient 230 than at least one of the x/y-position detectors. The configuration of the first ionization strip detector 410 and the second ionization strip detector 415 positioned between the first TOF detector 474 and the second TOF detector 478 provides both a separation pathlength and particle slowing materials between the first and second TOF detectors 474, 478. Generally, any of the layers/sheets of the time of flight system 470 are layered and substantially contacting or are separated by a distance, such as greater than 1, 2, 5, or 10 mm.

The inventor notes that use of one or more z-axis energy detectors that are separate from the x/y-position detection sheets allows the associated electronics or data acquisition processes for each detector plane to be specifically tuned for its purpose. For example the x and y positional tracking planes could be optimized for slower response and higher spatial resolution, whereas the 'z'-plane or the time plane would be optimized for the highest temporal resolution, giving up much if not all x-y positional information.

Referring now to FIG. 2 and FIGS. 4(I-K), the first and second TOF detectors 474, 478 are optionally used with the scintillation material and/or scintillation detector system 210, such as through positioning the first and second TOF detectors 474, 478 between the patient 230 and the scintillation material.

Generally, the time of flight system 470 detects time of flight of the residual charged particle beam 267 and uses the time of flight in the process of imaging, such as via beam scanning, beam dispersal, rotation, and/or tomographic imaging of the tumor 220 of the patient 230 with or without conversion of the elapsed time between the first and second TOF detectors 474, 478 into a corresponding energy.

Beam State Determination

Figure 4L:
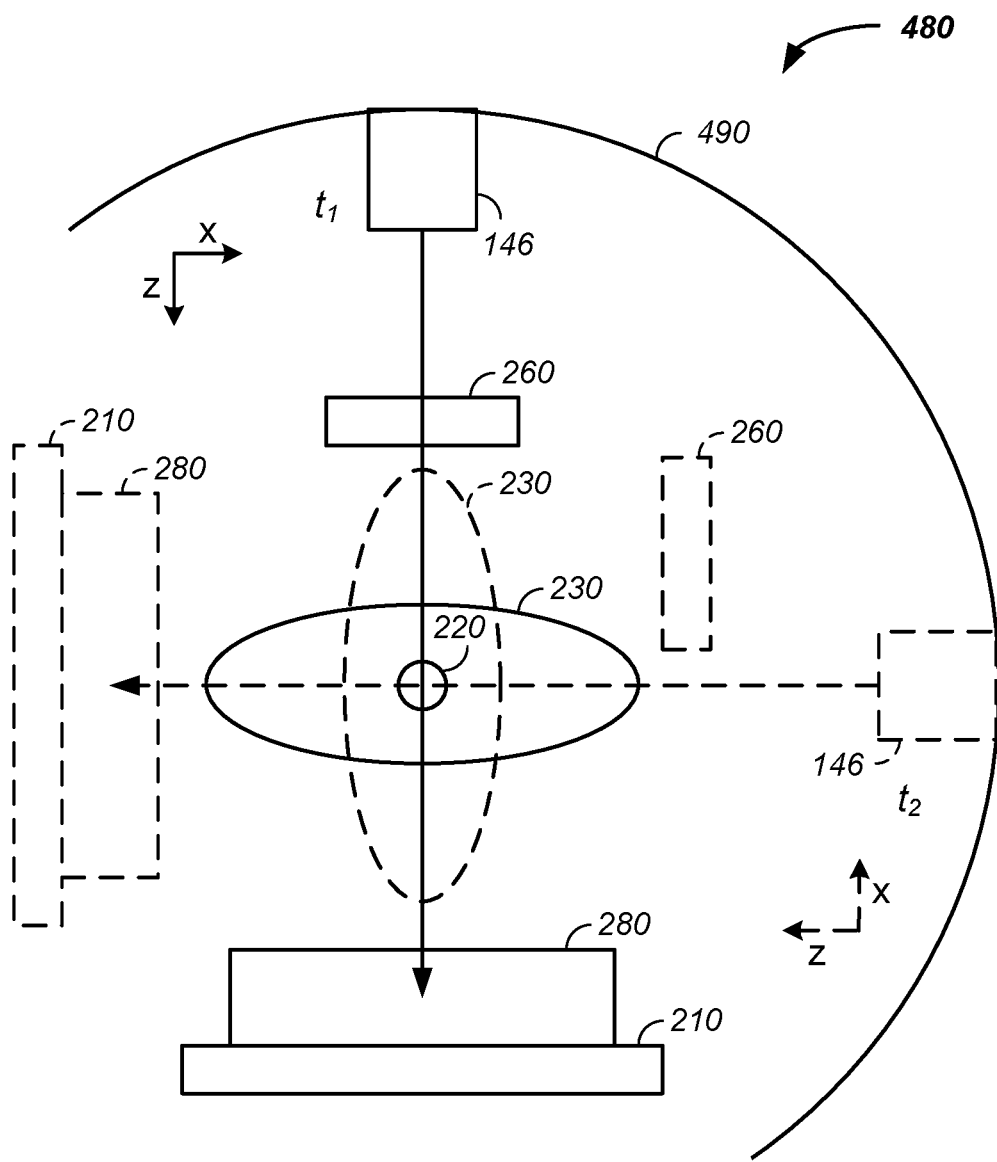
FIG. 4L illustrates the scintillation detector rotating with the patient and gantry nozzle.

Still again to FIG. 4A and referring now to FIG. 4L, the integrated tomography-cancer therapy system 400 is illustrated with an optional configuration of elements of the charged particle beam state determination system 250 being co-rotatable with the nozzle system 146 of the cancer therapy system 100. More particularly, in one case sheets of the charged particle beam state determination system 250 positioned prior to, posterior to, or on both sides of the patient 230 co-rotate with the scintillation material about any axis, such as illustrated with rotation about the y-axis. Further, any element of the charged particle beam state determination system 250, such as a detector, two-dimensional detector, multiple two-dimensional detectors, time-of-flight detector, and/or light coupling optic move as the gantry moves, such as along a common arc of movement of the nozzle system 146 and/or at a fixed distance to the common arc. For instance, as the gantry moves, a monitoring camera positioned on the opposite side of the tumor 220 or patient 230 from the nozzle system 146 maintains a position on the opposite side of the tumor 220 or patient 230. In various cases, co-rotation is achieved by co-rotation of the gantry of the charged particle beam system and a support of the patient, such as the rotatable platform 253, which is also referred to herein as a movable or dynamically positionable patient platform, patient chair, or patient couch. Mechanical elements, such as the support element 251 affix the various elements of the charged particle beam state determination system 250 relative to each other, relative to the nozzle system 146, and/or relative to the patient 230. For example, the support elements 251 maintain a second distance, $d_2$, between a position of the tumor 220 and the third tracking plane 280 and/or maintain a third distance, $d_3$, between a position of the third tracking plane 280 and the scintillation material and/or a scintillation detector element 205 of the scintillation detector system 210. More generally, support elements 251 optionally dynamically position any element about the patient 230 relative to one another or in x,y,z-space in a patient diagnostic/treatment room, such as via computer control.

Referring now to FIG. 4L, positioning the nozzle system 146 of a gantry 490 or gantry system on an opposite side of the patient 230 from a detection surface, such as the scintillation material of the scintillation detector system 210, in a gantry movement system 480 is described. Generally, in the gantry movement system 480, as the gantry 490 rotates about an axis the nozzle/nozzle system 146 and/or one or more magnets of the beam transport system 135 are repositioned. As illustrated, the nozzle system 146 is positioned by the gantry 490 in a first position at a first time, $t_1$, and in a second position at a second time, $t_2$, where n positions are optionally possible. An electromechanical system, such as a patient table, patient couch, patient couch, patient rotation device, and/or a scintillation plate holder maintains the patient 230 between the nozzle system 146 and the scintillation material of the tomography system 200. Similarly, not illustrated for clarity of presentation, the electromechanical system maintains a position of the third tracking plane 280 and/or a position of the fourth tracking plane 290 on a posterior or opposite side of the patient 230 from the nozzle system 146 as the gantry 490 rotates or moves the nozzle system 146. Similarly, the electromechanical system maintains a position of the first tracking plane 260 or first screen and/or a position of the second tracking plane 270 or second screen on a same or prior side of the patient 230 from the nozzle system 146 as the gantry 490 rotates or moves the nozzle system 146. As illustrated, the electromechanical system optionally positions the first tracking plane 260 in the positively charged particle path at the first time, $t_1$, and rotates, pivots, and/or slides the first tracking plane 260 out of the positively charged particle path at the second time, $t_2$. The electromechanical system is optionally and preferably connected to the main controller 110 and/or the treatment delivery control system 112. The electromechanical system optionally maintains a fixed distance between: (1) the patient and the nozzle system 146 or the nozzle end, (2) the patient 230 or tumor 220 and the scintillation material, and/or (3) the nozzle system 146 and the scintillation material at a first treatment time with the gantry 490 in a first position and at a second treatment time with the gantry 490 in a second position. Use of a common charged particle beam path for both imaging and cancer treatment and/or maintaining known or fixed distances between beam transport/guide elements and treatment and/or detection surface enhances precision and/or accuracy of a resultant image and/or tumor treatment, such as described supra.

System Integration

Any of the systems and/or elements described herein are optionally integrated together and/or are optionally integrated with known systems.

Treatment Delivery Control System

Referring now to FIG. 5, a centralized charged particle treatment system 500 is illustrated. Generally, once a charged particle therapy plan is devised, a central control system or treatment delivery control system 112 is used to control sub-systems while reducing and/or eliminating direct communication between major subsystems. Generally, the treatment delivery control system 112 is used to directly control multiple subsystems of the cancer therapy system without direct communication between selected subsystems, which enhances safety, simplifies quality assurance and quality control, and facilitates programming. For example, the treatment delivery control system 112 directly controls one or more of: an imaging system, a positioning system, an injection system, a radio-frequency quadrupole system, a linear accelerator, a ring accelerator or synchrotron, an extraction system, a beam line, an irradiation nozzle, a gantry, a display system, a targeting system, and a verification system. Generally, the control system integrates subsystems and/or integrates output of one or more of the above described cancer therapy system elements with inputs of one or more of the above described cancer therapy system elements.

Still referring to FIG. 5, an example of the centralized charged particle treatment system 1000 is provided. Initially, a doctor, such as an oncologist, prescribes 510 or recommends tumor therapy using charged particles. Subsequently, treatment planning 520 is initiated and output of the treatment planning step 520 is sent to an oncology information system 530 and/or is directly sent to the treatment delivery system 112, which is an example of the main controller 110.

Still referring to FIG. 5, the treatment planning step 520 is further described. Generally, radiation treatment planning is a process where a team of oncologist, radiation therapists, medical physicists, and/or medical dosimetrists plan appropriate charged particle treatment of a cancer in a patient. Typically, one or more imaging systems 170 are used to image the tumor and/or the patient, described infra. Planning is optionally: (1) forward planning and/or (2) inverse planning. Cancer therapy plans are optionally assessed with the aid of a dose-volume histogram, which allows the clinician to evaluate the uniformity of the dose to the tumor and surrounding healthy structures. Typically, treatment planning is almost entirely computer based using patient computed tomography data sets using multimodality image matching, image co-registration, or fusion.

Forward Planning

In forward planning, a treatment oncologist places beams into a radiotherapy treatment planning system including: how many radiation beams to use and which angles to deliver each of the beams from. This type of planning is used for relatively simple cases where the tumor has a simple shape and is not near any critical organs.

Inverse Planning

In inverse planning, a radiation oncologist defines a patient's critical organs and tumor and gives target doses and importance factors for each. Subsequently, an optimization program is run to find the treatment plan which best matches all of the input criteria.

Oncology Information System

Still referring to FIG. 5, the oncology information system 530 is further described. Generally, the oncology information system 530 is one or more of: (1) an oncology-specific electronic medical record, which manages clinical, financial, and administrative processes in medical, radiation, and surgical oncology departments; (2) a comprehensive information and image management system; and (3) a complete patient information management system that centralizes patient data; and (4) a treatment plan provided to the charged particle beam system 100, main controller 110, and/or the treatment delivery control system 112. Generally, the oncology information system 530 interfaces with commercial charged particle treatment systems.

Safety System/Treatment Delivery Control System

Still referring to FIG. 5, the treatment delivery control system 112 also referred to as a main subsystem controller and/or a control system is further described. Generally, the treatment delivery control system 112 receives treatment input, such as a charged particle cancer treatment plan from the treatment planning step 520 and/or from the oncology information system 530 and uses the treatment input and/or treatment plan to control one or more subsystems of the charged particle beam system 100. The treatment delivery control system 112 is an example of the main controller 110, where the treatment delivery control system receives subsystem input from a first subsystem of the charged particle beam system 100 and provides to a second subsystem of the charged particle beam system 100: (1) the received subsystem input directly, (2) a processed version of the received subsystem input, and/or (3) a command, such as used to fulfill requisites of the treatment planning step 520 or direction of the oncology information system 530. Generally, most or all of the communication between subsystems of the charged particle beam system 100 go to and from the treatment delivery control system 112 and not directly to another subsystem of the charged particle beam system 100. Use of a logically centralized treatment delivery control system has many benefits, including: (1) a single centralized code to maintain, debug, secure, update, and to perform checks on, such as quality assurance and quality control checks; (2) a controlled logical flow of information between subsystems; (3) an ability to replace a subsystem with only one interfacing code revision; (4) room security; (5) software access control; (6) a single centralized control for safety monitoring; and (7) that the centralized code results in an integrated safety system encompassing a majority or all of the subsystems 540 and/or subsystem elements of the charged particle beam system 100. Examples of subsystems of the charged particle cancer therapy system 100 include: a radio frequency quadrupole 550, a radio frequency quadrupole linear accelerator, the injection system 120, the synchrotron 130, the accelerator system 131, the extraction system 134, any controllable or monitorable element of the beam line 268, the targeting/delivery system 140, the nozzle system 146, the imaging system 170, such as one or more of the imaging systems described herein, a gantry 560 or an element of the gantry 560, the patient interface module 150, a patient positioner 152, the display system 160, the imaging system 170, the patient position verification system 179, such as an imaging system, any element described supra, and/or any subsystem element. A treatment change 570 at time of treatment is optionally computer generated with or without the aid of a technician or physician and approved while the patient is still in the treatment room, in the treatment chair, and/or in a treatment position.

Example I

In a first example, the treatment delivery control system 112 or the central control system of a cancer therapy system comprises modular sub-system code sections for a plurality of, optionally modular, sub-systems of the cancer therapy system, where a replacement of a first sub-system code section of the modular sub-system code sections accompanies a replacement of a first sub-system of the plurality of sub-systems of the cancer therapy system. In one case, only the first sub-system code section is replaced upon replacement of the first sub-system of the cancer therapy system. Optionally, a main control section controlling the modular sub-system code sections is also modified upon replacement of the first sub-system, such as without modification to modular sub-system code sections to non-replaced modular sub-systems of the cancer therapy system.

Example II

In a second example, a method and/or apparatus for controlling tumor treatment with positively charged particles, comprises the steps of: (1) a control system, such as the main controller 110 and/or the treatment delivery control system 112 controlling the charged particle beam system 100 and/or a cancer therapy system, where the control system comprises a set of modular control units 116 and the cancer therapy system comprises a set of subsystems and/or subsystem elements, such as any of the subsystems described herein; (2) altering a first subsystem of the set of subsystem elements; and (3) updating a first modular control unit, of the set of modular control units 116, corresponding to the first subsystem without a necessitated change of remaining elements and/or code elements of the set of modular control units corresponding to non-altered subsystem elements of the set of subsystem elements. Optionally and preferably: (1) the control system communicates with each of the set of subsystem elements without direct communication between the set of subsystem elements and/or (2) the control system directly controls each of the subsystem elements. Further, it is recognized that even with distinct code modules for distinct subsystems, a control code option includes code controlling each of the code modules, such as a main subsystem controller 114 and/or code for the main subsystem controller 114. Accordingly, replacing and/or altering a first subsystem and/or component thereof optionally requires a modification to a main subsystem controller code of the main subsystem controller and/or control system, the main subsystem controller code configured to control one or more of the set of subsystem controls. Optionally and preferably, when updating and/or replacing at least one element of the set of subsystems, updating or replacing the main subsystem controller and/or code thereof along with updating or replacing the corresponding control module of the set of modular control units is performed without a required update and/or replacement of non-modified subsystems of the set of subsystem elements. Stated again, replacing a first subsystem, such as an X-ray system, is accompanied with a change to an X-ray system control code with an optional change to code controlling the set of subsystems without necessitating replacing or changing code modules corresponding to non-updated subsystems of the cancer therapy system. Herein, a replacement and/or update includes a continued lease option, a new lease, a new purchase, and the like.

The inventor notes that the above described control system functions to control, with replacement or activated cade sections, multiple subsystem types, such as: (1) a synchrotron or other particle accelerator; (2) a first imager type and/or a second imager type; (3) a first patient positioning system or a second patient positioning system; (4) a first injector system type or a second inject system type; (5) a first gantry control system or a second gantry control system; (6) a first subsystem interface protocol or a second subsystem interface protocol, to allow sale of the code to multiple different companies using differing approaches of forming, accelerating, transporting, and/or targeting positively charged particles to a tumor of a patient with only inclusion and/or activation of the proper sub-modules/subsystem controls for a particular cancer therapy setup, which reduces software costs for providing custom software to particular subsystems where commonalities on the control process exist and/or commonalities in the control code exist, which allows repeated use of common code sections, simplifies updates to code related to changes in a subsystem, and/or facilitates regulatory process approval having to verify code for a limited section of the entire control system code.

Integrated Cancer Treatment-Imaging System

One or more imaging systems 170 are optionally used in a fixed position in a cancer treatment room and/or are moved with a gantry system, such as a gantry system supporting: a portion of the beam transport system 135, the targeting/delivery control system 140, and/or moving or rotating around a patient positioning system, such as in the patient interface module. Without loss of generality and to facilitate description of the invention, examples follow of an integrated cancer treatment-imaging system. In each system, the beam transport system 135 and/or the nozzle system 146 indicates a positively charged beam path, such as from the synchrotron, for tumor treatment and/or for tomography, as described supra.

Example I

Figure 6A:
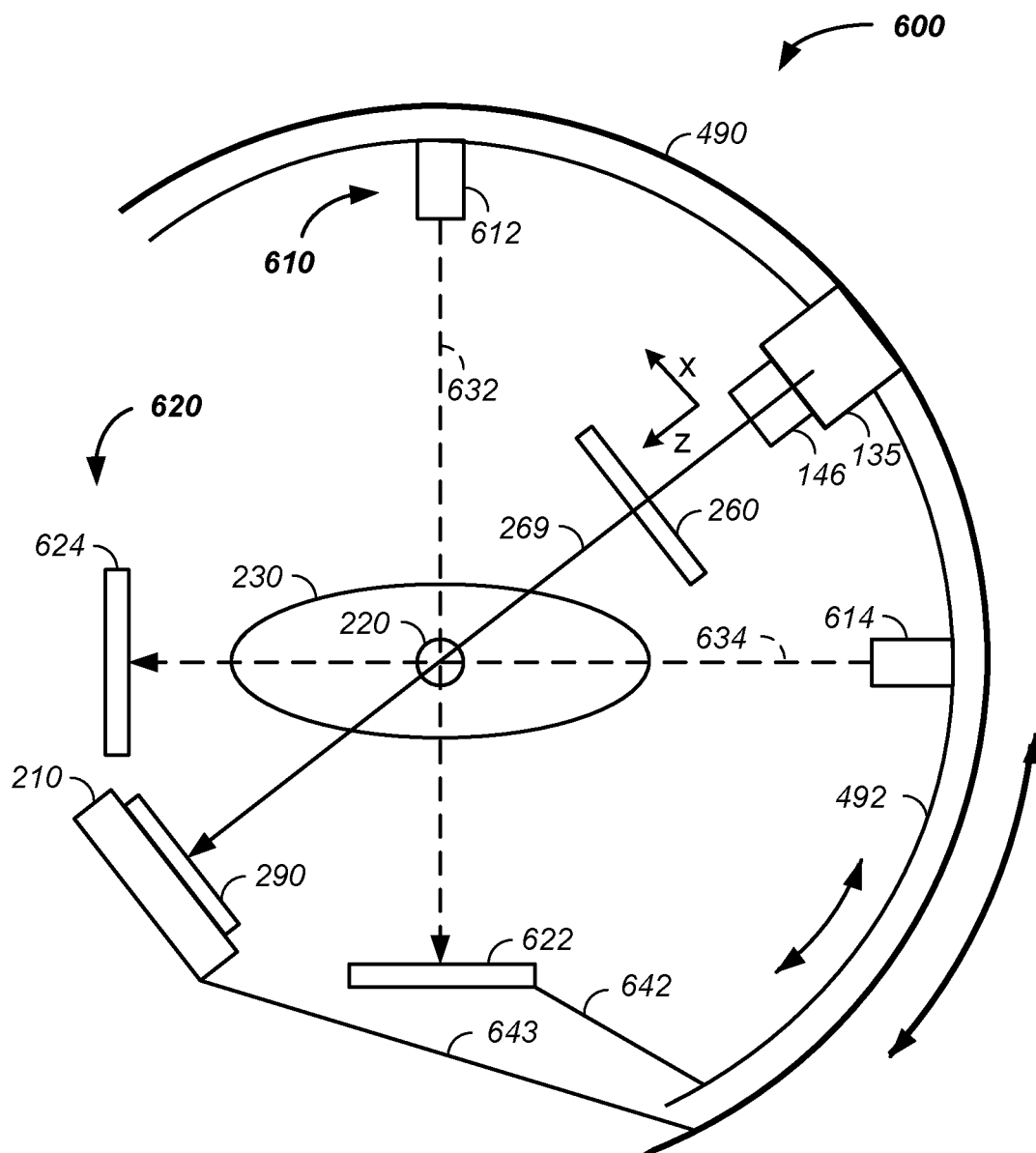
FIG. 6A illustrates a two-dimensional-two-dimensional imaging system relative to a cancer treatment beam.

Referring now to FIG. 6A, a first example of an integrated cancer treatment-imaging system 600 is illustrated. In this example, the charged particle beam system 100 is illustrated with a treatment beam 269 directed to the tumor 220 of the patient 230 along the z-axis. Also illustrated is a set of imaging sources 610, imaging system elements, and/or paths therefrom and a set of detectors 620 corresponding to a respective element of the set of imaging sources 610. Herein, the set of imaging sources 610 are referred to as sources, but are optionally any point or element of the beam train prior to the tumor or a center point about which the gantry rotates. Hence, a given imaging source is optionally a dispersion element used to form cone beam. As illustrated, a first imaging source 612 yields a first beam path 632 and a second imaging source 614 yields a second beam path 634, where each path passes at least into the tumor 220 and optionally and preferably to a first detector array 622 and a second detector array 624, respectively, of the set of detectors 620. Herein, the first beam path 632 and the second beam path 634 are illustrated as forming a ninety degree angle, which yields complementary images of the tumor 220 and/or the patient 230. However, the formed angle is optionally any angle from ten to three hundred fifty degrees. Herein, for clarity of presentation, the first beam path 632 and the second beam path 634 are illustrated as single lines, which optionally is an expanding, uniform diameter, or focusing beam. Herein, the first beam path 632 and the second beam path 634 are illustrated in transmission mode with their respective sources and detectors on opposite sides of the patient 230. However, a beam path from a source to a detector is optionally a scattered path and/or a diffuse reflectance path. Optionally, one or more detectors of the set of detectors 620 are a single detector element, a line of detector elements, or preferably a two-dimensional detector array. Use of two two-dimensional detector arrays is referred to herein as a two-dimensional-two-dimensional imaging system or a 2D-2D imaging system.

Still referring to FIG. 6A, the first imaging source 612 and the second imaging source 614 are illustrated at a first position and a second position, respectively. Each of the first imaging source 612 and the second imaging source 614 optionally: (1) maintain a fixed position; (2) provide the first beam path(s) 632 and the second beam path(s) 634, respectively, such as to an imaging system detector 620 or through the gantry 490, such as through a set of one or more holes or slits; (3) provide the first beam path 632 and the second beam path 634, respectively, off axis to a plane of movement of the nozzle system 146; (4) move with the gantry 490 as the gantry 490 rotates about at least a first axis; (5) move with a secondary imaging system independent of movement of the gantry, as described supra; and/or (6) represent a narrow cross-diameter section of an expanding cone beam path.

Figure 6B:
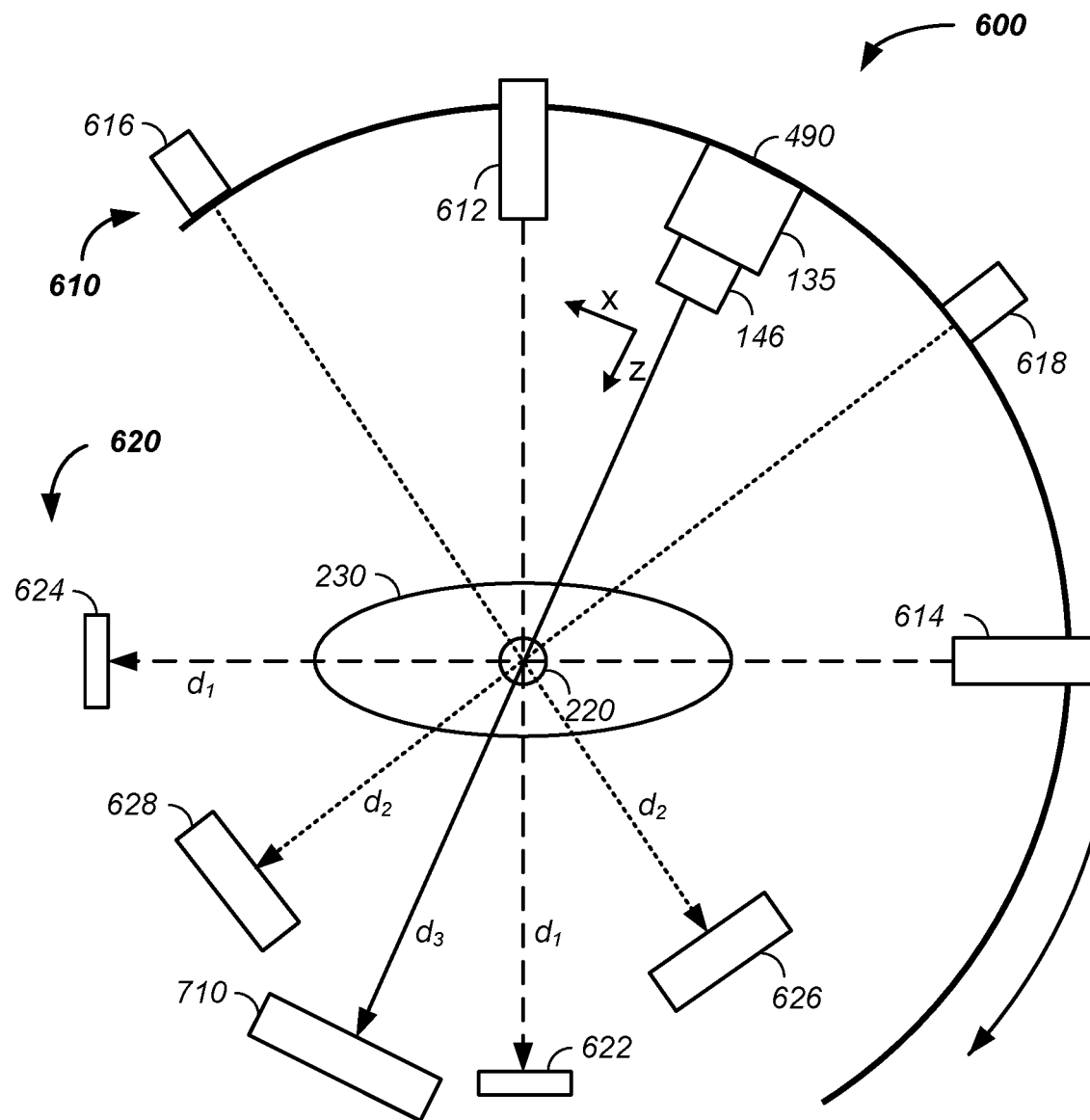
FIG. 6B illustrates multiple gantry supported imaging systems.

Still referring to FIG. 6A, the set of detectors 620 are illustrated as coupling with respective elements of the set of sources 610. Each member of the set of detectors 620 optionally and preferably co-moves/and/or co-rotates with a respective member of the set of sources 610. Thus, if the first imaging source 612 is statically positioned, then the first detector 622 is optionally and preferably statically positioned. Similarly, to facilitate imaging, if the first imaging source 612 moves along a first arc as the gantry 490 moves, then the first detector 622 optionally and preferably moves along the first arc or a second arc as the gantry 490 moves, where relative positions of the first imaging source 612 on the first arc, a point that the gantry 490 moves about, and relative positions of the first detector 622 along the second arc are constant. To facilitate the process, the detectors are optionally mechanically linked, such as with a mechanical support to the gantry 643 in a manner that when the gantry 490 moves, the gantry moves both the source and the corresponding detector. Optionally, the source moves and a series of detectors, such as along the second arc, capture a set of images. As illustrated in FIG. 6A, the first imaging source 612, the first detector array 622, the second imaging source 614, and the second detector array 624 are coupled to a rotatable imaging system support 642, which optionally rotates independently of the gantry 490 as further described infra. As illustrated in FIG. 6B, the first imaging source 612, the first detector array 622, the second imaging source 614, and the second detector array 624 are coupled to the gantry 490, which in this case is a rotatable gantry.

Still referring to FIG. 6A, optionally and preferably, elements of the set of sources 610 combined with elements of the set of detectors 620 are used to collect a series of responses, such as one source and one detector yielding a detected intensity and rotatable imaging system support 642 preferably a set of detected intensities to form an image. For instance, the first imaging source 612, such as a first X-ray source or first cone beam X-ray source, and the first detector 622, such as an X-ray film, digital X-ray detector, or two-dimensional detector, yield a first X-ray image of the patient at a first time and a second X-ray image of the patient at a second time, such as to confirm a maintained location of a tumor or after movement of the gantry and/or nozzle system 146 or rotation of the patient 230. A set of n images using the first imaging source 612 and the first detector 622 collected as a function of movement of the gantry and/or the nozzle system 146 supported by the gantry and/or as a function of movement and/or rotation of the patient 230 are optionally and preferably combined to yield a three-dimensional image of the patient 230, such as a three-dimensional X-ray image of the patient 230, where n is a positive integer, such as greater than 1, 2, 3, 4, 5, 10, 15, 25, 50, or 100. The set of n images is optionally gathered as described in combination with images gathered using the second imaging source 614, such as a second X-ray source or second cone beam X-ray source, and the second detector 624, such as a second X-ray detector, where the use of two, or multiple, source/detector combinations are combined to yield images where the patient 230 has not moved between images as the two, or the multiple, images are optionally and preferably collected at the same time, such as with a difference in time of less than 0.01, 0.1, 1, or 5 seconds. Longer time differences are optionally used. Preferably the n two-dimensional images are collected as a function of rotation of the gantry 490 about the tumor and/or the patient and/or as a function of rotation of the patient 230 and the two-dimensional images of the X-ray cone beam are mathematically combined to form a three-dimensional image of the tumor 220 and/or the patient 230. Optionally, the first X-ray source and/or the second X-ray source is the source of X-rays that are divergent forming a cone through the tumor. A set of images collected as a function of rotation of the divergent X-ray cone around the tumor with a two-dimensional detector that detects the divergent X-rays transmitted through the tumor is used to form a three-dimensional X-ray of the tumor and of a portion of the patient, such as in X-ray computed tomography.

Still referring to FIG. 6A, use of two imaging sources and two detectors set at ninety degrees to one another allows the gantry 490 or the patient 230 to rotate through half an angle required using only one imaging source and detector combination. A third imaging source/detector combination allows the three imaging source/detector combination to be set at sixty degree intervals allowing the imaging time to be cut to that of one-third that gantry 490 or patient 230 rotation required using a single imaging source-detector combination. Generally, n source-detector combinations reduces the time and/or the rotation requirements to 1/n. Further reduction is possible if the patient 230 and the gantry 490 rotate in opposite directions. Generally, the used of multiple source-detector combination of a given technology allow for a gantry that need not rotate through as large of an angle, with dramatic engineering benefits.

Still referring to FIG. 6A, the set of sources 610 and set of detectors 620 optionally use more than one imaging technology. For example, a first imaging technology uses X-rays, a second used fluoroscopy, a third detects fluorescence, a fourth uses cone beam computed tomography or cone beam CT, and a fifth uses other electromagnetic waves. Optionally, the set of sources 610 and the set of detectors 620 use two or more sources and/or two or more detectors of a given imaging technology, such as described supra with two X-ray sources to n X-ray sources.

Still referring to FIG. 6A, use of one or more of the set of sources 610 and use of one or more of the set of detectors 620 is optionally coupled with use of the positively charged particle tomography system described supra. As illustrated in FIG. 6A, the positively charged particle tomography system uses a second mechanical support 643 to co-rotate the scintillation material of the scintillator detector system 210 with the gantry 490, as well as to co-rotate an optional sheet, such as the first tracking plane 260 and/or the fourth tracking plane 290.

Example II

Referring now to FIG. 6B, a second example of the integrated cancer treatment-imaging system 600 is illustrated using greater than three imagers.

Still referring to FIG. 6B, two pairs of imaging systems are illustrated. Particularly, the first and second imaging source 612, 614 coupled to the first and second detectors 622, 624 are as described supra. For clarity of presentation and without loss of generality, the first and second imaging systems are referred to as a first X-ray imaging system and a second X-ray imaging system. The second pair of imaging systems uses a third imaging source 616 coupled to a third detector 626 and a fourth imaging source 618 coupled to a fourth detector 628 in a manner similar to the first and second imaging systems described in the previous example. Here, the second pair of imaging systems optionally and preferably uses a second imaging technology, such as fluoroscopy. Optionally, the second pair of imaging systems is a single unit, such as the third imaging source 616 coupled to the third detector 626, and not a pair of units. Optionally, one or more of the set of imaging sources 610 are statically positioned while one of more of the set of imaging sources 610 co-rotate with the gantry 490. Pairs of imaging sources/ detector optionally have common and distinct distances, such as a first distance, $d_1$, such as for a first source-detector pair and a second distance, $d_2$, such as for a second source-detector or second source-detector pair. As illustrated, the tomography detector or the scintillation material is at a third distance, $d_3$. The distinct differences allow the source-detector elements to rotate on a separate rotation system at a rate different from rotation of the gantry 490, which allows collection of a full three-dimensional image while tumor treatment is proceeding with the positively charged particles.

Example III

Figure 6C:
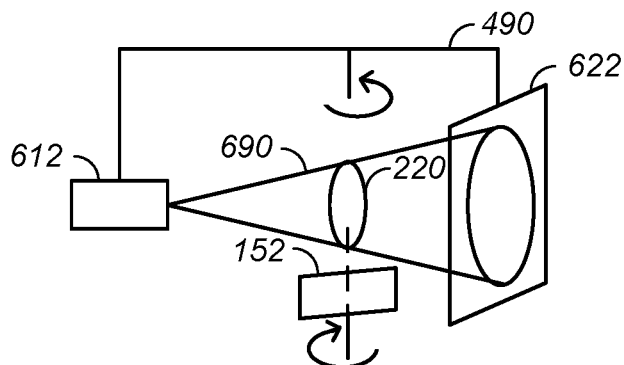
FIG. 6C illustrates a rotatable cone beam.

For clarity of presentation, referring now to FIG. 6C, any of the beams or beam paths described herein is optionally a cone beam 690 as illustrated. The patient support 152 is an mechanical and/or electromechanical device used to position, rotate, and/or constrain any portion of the tumor 220 and/or the patient 230 relative to any axis.

Tomography Detector System

A tomography system optically couples the scintillation material to a detector. As described, supra, the tomography system optionally and preferably uses one or more detection sheets, beam tracking elements, and/or tracking detectors to determine/monitor the charged particle beam position, shape, and/or direction in the beam path prior to and/or posterior to the sample, imaged element, patient, or tumor. Herein, without loss of generality, the detector is described as a detector array or two-dimensional detector array positioned next to the scintillation material; however, the detector array is optionally optically coupled to the scintillation material using one or more optics. Optionally and preferably, the detector array is a component of an imaging system that images the scintillation material, where the imaging system resolves an origin volume or origin position on a viewing plane of the secondary photon emitted resultant from passage of the residual charged particle beam 267. As described, infra, more than one detector array is optionally used to image the scintillation material from more than one direction, which aids in a three-dimensional reconstruction of the photonic point(s) of origin, positively charged particle beam path, and/or tomographic image.

Imaging

Generally, medical imaging is performed using an imaging apparatus to generate a visual and/or a symbolic representation of an interior constituent of the body for diagnosis, treatment, and/or as a record of state of the body. Typically, one or more imaging systems are used to image the tumor and/or the patient. For example, the X-ray imaging system and/or the positively charged particle imaging system, described supra, are optionally used individually, together, and/or with any additional imaging system, such as use of X-ray radiography, magnetic resonance imaging, medical ultrasonography, thermography, medical photography, positron emission tomography (PET) system, single-photon emission computed tomography (SPECT), and/or another nuclear/charged particle imaging technique.

As part of an imaging system, time-of-flight of the residual charged particle beam is optionally used to determine the residual energy/velocity of the charged particle beam after passing through the patient along with knowledge of the charged particle beam energy entering the patient to map/image internal constituents/components of the patient. For example, a first time-of-flight detection panel is used to determine when a charged particle reaches the first detection panel and a second time-of-flight detection panel is used to determine when the charged particle reaches the second detection panel, where the two detection panels are positioned on an opposite side of a patient position relative to the exit nozzle 146. The distance between detection panel elements detecting the charged particle and the elapsed time is used to determine velocity/energy of the charged particle. Optionally, a particle decelerator, such as a metal film, an electron emitting film, and/or a beryllium sheet is used to slow the charged particle between the first and second time-of-flight detection panels and/or as a current emitting element of the second time-of-flight detection panel to bring elapsed times down from the picosecond and/or nanosecond time period to a more readily measured time interval of millisecond or microseconds.

Fiducial Marker

Fiducial markers and fiducial detectors are optionally used to locate, target, track, avoid, and/or adjust for objects in a treatment room that move relative to the nozzle or nozzle system 146 of the charged particle beam system 100 and/or relative to each other. Herein, for clarity of presentation and without loss of generality, fiducial markers and fiducial detectors are illustrated in terms of a movable or statically positioned treatment nozzle and a movable or static patient position. However, generally, the fiducial markers and fiducial detectors are used to mark and identify position, or relative position, of any object in a treatment room, such as a cancer therapy treatment room 922. Herein, a fiducial indicator refers to either a fiducial marker or a fiducial detector. Herein, photons travel from a fiducial marker to a fiducial detector.

Herein, fiducial refers to a fixed basis of comparison, such as a point or a line. A fiducial marker or fiducial is an object placed in the field of view of an imaging system, which optionally appears in a generated image or digital representation of a scene, area, or volume produced for use as a point of reference or as a measure. Herein, a fiducial marker is an object placed on, but not into, a treatment room object or patient. Particularly, herein, a fiducial marker is not an implanted device in a patient. In physics, fiducials are reference points: fixed points or lines within a scene to which other objects can be related or against which objects can be measured. Fiducial markers are observed using a sighting device for determining directions or measuring angles, such as an alidade or in the modern era a digital detection system. Two examples of modern position determination systems are the Passive Polaris Spectra System and the Polaris Vicra System (NDI, Ontario, Canada).

Figure 7A:
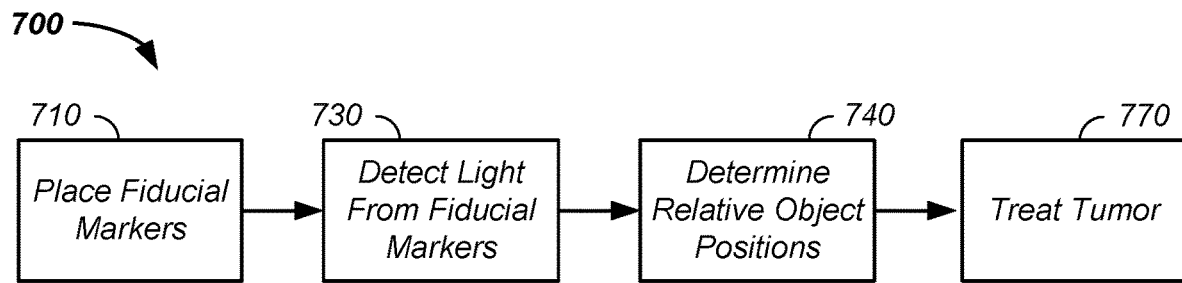
FIG. 7A illustrates a process of determining position of treatment room objects and FIG. 7B illustrates an iterative position tracking, imaging, and treatment system.

Referring now to FIG. 7A, use of a fiducial marker system 700 is described. Generally, a fiducial marker is placed 710 on an object, light from the fiducial marker is detected 730, relative object positions are determined 740, and a subsequent task is performed, such as treating a tumor 220. For clarity of presentation and without loss of generality, non-limiting examples of uses of fiducial markers in combination with X-ray and/or positively charged particle tomographic imaging and/or treatment using positively charged particles are provided, infra.

Example I

Figure 8:
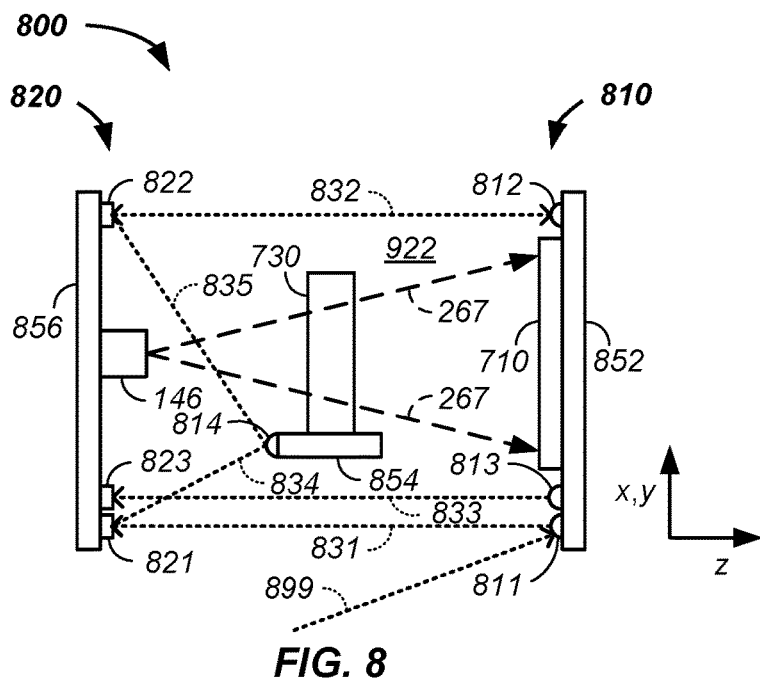
FIG. 8 illustrates a fiducial marker enhanced tomography imaging system.

Referring now to FIG. 8, a fiducial marker aided tomography system 800 is illustrated and described. Generally, a set of fiducial marker detectors 820 detects photons emitted from and/or reflected off of a set of fiducial markers 810 and resultant determined distances and calculated angles are used to determine relative positions of multiple objects or elements, such as in the treatment room 922.

Still referring to FIG. 8, initially, a set of fiducial markers 810 are placed on one or more elements. As illustrated, a first fiducial marker 811, a second fiducial marker 812, and a third fiducial marker 813 are positioned on a first, preferably rigid, support element 852. As illustrated, the first support element 852 supports a scintillation material of a scintillation detector element 205 of the scintillation detector system 210. As each of the first, second, and third fiducial markers 811, 812, 813 and the scintillation material of the scintillation detector element are affixed or statically positioned onto the first support element 852, the relative position of the scintillation material is known, based on degrees of freedom of movement of the first support element, if the positions of the first fiducial marker 811, the second fiducial marker 812, and/or the third fiducial marker 813 is known. In this case, one or more distances between the first support element 852 and a third support element 856 are determined, as further described infra.

Still referring to FIG. 8, a set of fiducial detectors 820 are used to detect light emitted from and/or reflected off one or more fiducial markers of the set of fiducial markers 810. As illustrated, ambient photons 821 and/or photons from an illumination source reflect off of the first fiducial marker 811, travel along a first fiducial path 831, and are detected by a first fiducial detector 821 of the set of fiducial detectors 820. In this case, a first signal from the first fiducial detector 821 is used to determine a first distance to the first fiducial marker 811. If the first support element 852 supporting the scintillation material only translates, relative to the nozzle system 146, along the z-axis, the first distance is sufficient information to determine a location of the scintillation material, relative to the nozzle system 146. Similarly, photons emitted, such as from a light emitting diode embedded into the second fiducial marker 812 travel along a second fiducial path 832 and generate a second signal when detected by a second fiducial detector 822, of the set of fiducial detectors 820. The second signal is optionally used to confirm position of the first support element 852, reduce error of a determined position of the first support element 852, and/or is used to determine extent of a second axis movement of the first support element 852, such as tilt of the first support element 852. Similarly, photons passing from the third fiducial marker 813 travel along a third fiducial path 833 and generate a third signal when detected by a third fiducial detector 823, of the set of fiducial detectors 820. The third signal is optionally used to confirm position of the first support element 852, reduce error of a determined position of the first support element 852, and/or is used to determine extent of a second or third axis movement of the first support element 852, such as rotation of the first support element 852.

If all of the movable elements within the treatment room 922 move together, then determination of a position of one, two, or three fiducial markers, dependent on degrees of freedom of the movable elements, is sufficient to determine a position of all of the co-movable movable elements. However, optionally two or more objects in the treatment room 922 move independently or semi-independently from one another. For instance, a first movable object optionally translates, tilts, and/or rotates relative to a second movable object. One or more additional fiducial markers of the set of fiducial markers 810 placed on each movable object allows relative positions of each of the movable objects to be determined.

Still referring to FIG. 8, a position of the patient 230 is determined relative to a position of the scintillation detector element of the scintillation detector system 210. As illustrated, a second support element 854 positioning the patient 230 optionally translates, tilts, and/or rotates relative to the first support element 852 positioning the scintillation material. In this case, a fourth fiducial marker 814, attached to the second support element 854 allows determination of a current position of the patient 230. As illustrated, a position of a single fiducial element, the fourth fiducial marker 814, is determined by the first fiducial detector 821 determining a first distance to the fourth fiducial marker 814 and the second fiducial detector 822 determining a second distance to the fourth fiducial marker 814, where a first arc of the first distance from the first fiducial detector 821 and a second arc of the second distance from the second fiducial detector 822 overlap at a point of the fourth fiducial marker 834 marking the position of the second support element 852 and the supported position of the patient 230. Combined with the above described system of determining location of the scintillation material, the relative position of the scintillation material to the patient 230, and thus the tumor 220, is determined.

Still referring to FIG. 8, one fiducial marker and/or one fiducial detector is optionally and preferably used to determine more than one distance or angle to one or more objects. In a first case, as illustrated, light from the fourth fiducial marker 814 is detected by both the first fiducial detector 821 and the second fiducial detector 822. In a second case, as illustrated, light detected by the first fiducial detector 821, passes from the first fiducial marker 811 and the fourth fiducial marker 814. Thus, (1) one fiducial marker and two fiducial detectors are used to determine a position of an object, (2) two fiducial markers on two elements and one fiducial detector is used to determine relative distances of the two elements to the single detector, and/or as illustrated and described below in relation to FIG. 10A, and/or (3) positions of two or more fiducial markers on a single object are detected using a single fiducial detector, where the distance and orientation of the single object is determined from the resultant signals. Generally, use of multiple fiducial markers and multiple fiducial detectors are used to determine or overdetermine positions of multiple objects, especially when the objects are rigid, such as a support element, or semi-rigid, such as a person, head, torso, or limb.

Still referring to FIG. 8, the fiducial marker aided tomography system 800 is further described. As illustrated, the set of fiducial detectors 820 are mounted onto the third support element 856, which has a known position and orientation relative to the nozzle system 146. Thus, position and orientation of the nozzle system 146 is known relative to the tumor 220, the patient 230, and the scintillation material through use of the set of fiducial markers 810, as described supra. Optionally, the main controller 110 uses inputs from the set of fiducial detectors 820 to: (1) dictate movement of the patient 230 or operator; (2) control, adjust, and/or dynamically adjust position of any element with a mounted fiducial marker and/or fiducial detector, and/or (3) control operation of the charged particle beam, such as for imaging and/or treating or performing a safety stop of the positively charged particle beam. Further, based on past movements, such as the operator moving across the treatment room 922 or relative movement of two objects, the main controller is optionally and preferably used to prognosticate or predict a future conflict between the treatment beam 269 and the moving object, in this case the operator, and take appropriate action or to prevent collision of the two objects.

Example II

Figure 9:
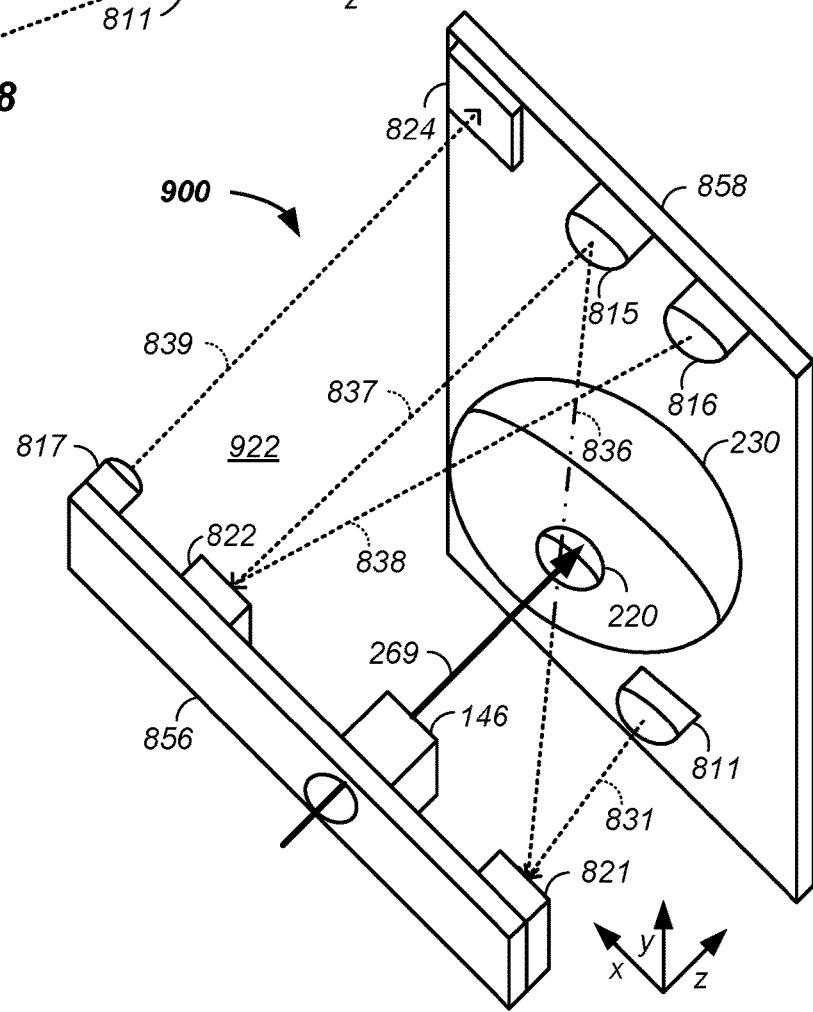
FIG. 9 illustrates a fiducial marker enhanced treatment system.

Referring now to FIG. 9, a fiducial marker aided treatment system 3400 is described. To clarify the invention and without loss of generality, this example uses positively charged particles to treat a tumor. However, the methods and apparatus described herein apply to imaging a sample, such as described supra.

Still referring to FIG. 9, four additional cases of fiducial marker-fiducial detector combinations are illustrated. In a first case, photons from the first fiducial marker 811 are detected using the first fiducial detector 821, as described in the previous example. However, photons from a fifth fiducial marker 815 are blocked and prevented from reaching the first fiducial detector 821 as a sixth fiducial path 836 is blocked, in this case by the patient 230. The inventor notes that the absence of an expected signal, disappearance of a previously observed signal with the passage of time, and/or the emergence of a new signal each add information on existence and/or movement of an object. In a second case, photons from the fifth fiducial marker 815 passing along a seventh fiducial path 837 are detected by the second fiducial detector 822, which illustrates one fiducial marker yielding a blocked and unblocked signal usable for finding an edge of a flexible element or an element with many degrees of freedom, such as a patient's hand, arm, or leg. In a third case, photons from the fifth fiducial marker 815 and a sixth fiducial marker 816, along the seventh fiducial path 837 and an eighth fiducial path 838 respectively, are detected by the second fiducial detector 822, which illustrates that one fiducial detector optionally detects signals from multiple fiducial markers. In this case, photons from the multiple fiducial sources are optionally of different wavelengths, occur at separate times, occur for different overlapping periods of time, and/or are phase modulated. In a fourth case, a seventh fiducial marker 817 is affixed to the same element as a fiducial detector, in this case the front surface plane of the third support element 856. Also, in the fourth case, a fourth fiducial detector 824, observing photons along a ninth fiducial path 839, is mounted to a fourth support element 858, where the fourth support element 858 positions the patient 230 and tumor 220 thereof and/or is attached to one or more fiducial source elements.

Still referring to FIG. 9 the fiducial marker aided treatment system 900 is further described. As described, supra, the set of fiducial markers 810 and the set of fiducial detectors 820 are used to determine relative locations of objects in the treatment room 922, which are the third support element 856, the fourth support element 858, the patient 230, and the tumor 220 as illustrated. Further, as illustrated, the third support element 856 comprises a known physical position and orientation relative to the nozzle system 146. Hence, using signals from the set of fiducial detectors 820, representative of positions of the fiducial markers 810 and room elements, the main controller 110 controls the treatment beam 269 to target the tumor 220 as a function of time, movement of the nozzle system 146, and/or movement of the patient 230.

Example III

Figure 10A:
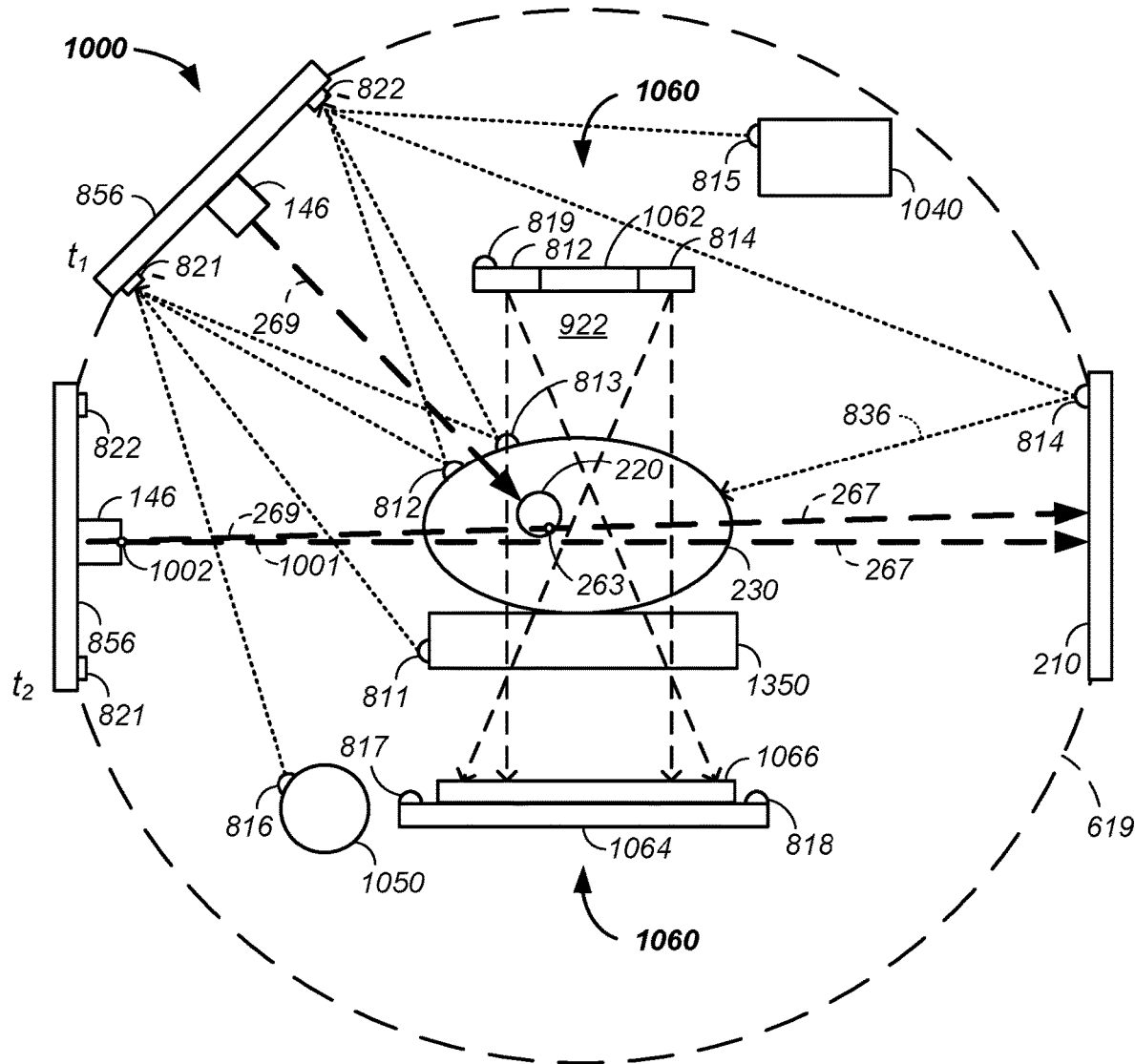
FIGS. 10(A-C) illustrate isocenterless cancer treatment systems.

Referring now to FIG. 10A, a fiducial marker aided treatment room system 1000 is described. Without loss of generality and for clarity of presentation, a zero vector 1001 is a vector or line emerging from the nozzle system 146 when the first axis controller 143, such as a vertical control, and the second axis controller 144, such as a horizontal control, of the scanning system 140 is turned off. Without loss of generality and for clarity of presentation, a zero point 1002 is a point on the zero vector 1001 at a plane of an exit face the nozzle system 146. Generally, a defined point and/or a defined line are used as a reference position and/or a reference direction and fiducial markers are defined in space relative to the point and/or line.

Six additional cases of fiducial marker-fiducial detector combinations are illustrated to further describe the fiducial marker aided treatment room system 1000. In a first case, the patient 230 position is determined. Herein, a first fiducial marker 811 marks a position of a patient positioning system 1350 and a second fiducial marker 812 marks a position of a portion of skin of the patient 230, such as a limb, joint, and/or a specific position relative to the tumor 220. In a second case, multiple fiducial markers of the set of fiducial markers 810 and multiple fiducial detectors of said set of fiducial detectors 820 are used to determine a position/relative position of a single object, where the process is optionally and preferably repeated for each object in the treatment room 922. As illustrated, the patient 230 is marked with the second fiducial marker 812 and a third fiducial marker 813, which are monitored using a first fiducial detector 821 and a second fiducial detector 822. In a third case, a fourth fiducial marker 814 marks the scintillation material and a sixth fiducial path 836 illustrates another example of a blocked fiducial path. In a fourth case, a fifth fiducial marker 815 marks an object not always present in the treatment room, such as a wheelchair 1040, walker, or cart. In a sixth case, a sixth fiducial marker 816 is used to mark an operator 1050, who is mobile and must be protected from an unwanted irradiation from the nozzle system 146.

Still referring to FIG. 10A, clear field treatment vectors and obstructed field treatment vectors are described. A clear field treatment vector comprises a path of the treatment beam 269 that does not intersect a non-standard object, where a standard object includes all elements in a path of the treatment beam 269 used to measure a property of the treatment beam 269, such as the first tracking plane 260, the second tracking plane 270, the third tracking plane 280, and the fourth tracking plane 290. Examples of non-standard objects or interfering objects include an arm of the patient couch, a back of the patient couch, and/or a supporting bar, such a robot arm. Use of fiducial indicators, such as a fiducial marker, on any potential interfering object allows the main controller 110 to only treat the tumor 220 of the patient 230 in the case of a clear field treatment vector. For example, fiducial markers are optionally placed along the edges or corners of the patient couch or patient positioning system or indeed anywhere on the patient couch. Combined with a-priori knowledge of geometry of the non-standard object, the main controller can deduce/calculate presence of the non-standard object in a current or future clear field treatment vector, forming a obstructed field treatment vector, and perform any of: increasing energy of the treatment beam 269 to compensate, moving the interfering non-standard object, and/or moving the patient 230 and/or the nozzle system 146 to a new position to yield a clear field treatment vector. Similarly, for a given determined clear filed treatment vector, a total treatable area, using scanning of the proton beam, for a given nozzle-patient couch position is optionally and preferably determined. Further, the clear field vectors are optionally and preferably predetermined and used in development of a radiation treatment plan.

Referring again to FIG. 7A, FIG. 8, FIG. 9, and FIG. 10A, generally, one or more fiducial markers and/or one or more fiducial detectors are attached to any movable and/or statically positioned object/element in the treatment room 922, which allows determination of relative positions and orientation between any set of objects in the treatment room 922.

Sound emitters and detectors, radar systems, and/or any range and/or directional finding system is optionally used in place of the source-photon-detector systems described herein.

2D-2D X-Ray Imaging

Still referring to FIG. 10A, for clarity of presentation and without loss of generality, a two-dimensional-two-dimensional (2D-2D) X-ray imaging system 1060 is illustrated, which is representative of any source-sample-detector transmission based imaging system. As illustrated, the 2D-2D imaging system 1060 includes a 2D-2D source end 1062 on a first side of the patient 230 and a 2D-2D detector end 1064 on a second side, an opposite side, of the patient 230. The 2D-2D source end 1062 holds, positions, and/or aligns source imaging elements, such as: (1) one or more imaging sources; (2) the first imaging source 612 and the second imaging source 622; and/or (3) a first cone beam X-ray source and a second cone beam X-ray source; while, the 2D-2D detector end 1064, respectively, holds, positions, and/or aligns: (1) one or more imaging detectors 1066; (2) a first imaging detector and a second imaging detector; and/or (3) a first cone beam X-ray detector and a second cone beam X-ray detector.

In practice, optionally and preferably, the 2D-2D imaging system 1060 as a unit rotates about a first axis around the patient, such as an axis of the treatment beam 269, as illustrated at the second time, $t_2$. For instance, at the second time, $t_2$, the 2D-2D source end 1062 moves up and out of the illustrated plane while the 2D-2D detector end 1064 moves down and out of the illustrated plane. Thus, the 2D-2D imaging system may operate at one or more positions through rotation about the first axis while the treatment beam 269 is in operation without interfering with a path of the treatment beam 269.

Optionally and preferably, the 2D-2D imaging system 1060 does not physically obstruct the treatment beam 269 or associated residual energy imaging beam from the nozzle system 146. Through relative movement of the nozzle system 146 and the 2D-2D imaging system 1060, a mean path of the treatment beam 269 and a mean path of X-rays from an X-ray source of the 2D-2D imaging system 1060 form an angle from 0 to 90 degrees and more preferably an angle of greater than 10, 20, 30, or 40 degrees and less than 80, 70, or 60 degrees. Still referring to FIG. 10A, as illustrated at the second time, $t_2$, the angle between the mean treatment beam and the mean X-ray beam is 45 degrees.

The 2D-2D imaging system 1060 optionally rotates about a second axis, such as an axis perpendicular to FIG. 10A and passing through the patient and/or passing through the first axis. Thus, as illustrated, as the exit port of the output nozzle system 146 moves along an arc and the treatment beam 269 enters the patient 230 from another angle, rotation of the 2D-2D imaging system 1060 about the second axis perpendicular to FIG. 10A, the first axis of the 2D-2D imaging system 1060 continues to rotate about the first axis, where the first axis is the axis of the treatment beam 269 or the residual charged particle beam 267 in the case of imaging with protons.

Optionally and preferably, one or more elements of the 2D-2D X-ray imaging system 1060 are marked with one or more fiducial elements, as described supra. As illustrated, the 2D-2D detector end 1064 is configured with a seventh fiducial marker 817 and an eighth fiducial marker 818 while the 2D-2D source end 1062 is configured with a ninth fiducial marker 819, where any number of fiducial markers are used.

In many cases, movement of one fiducial indicator necessitates movement of a second fiducial indicator as the two fiducial indicators are physically linked. Thus, the second fiducial indicator is not strictly needed, given complex code that computes the relative positions of fiducial markers that are often being rotated around the patient 230, translated past the patient 230, and/or moved relative to one or more additional fiducial markers. The code is further complicated by movement of non-mechanically linked and/or independently movable obstructions, such as a first obstruction object moving along a first concentric path and a second obstruction object moving along a second concentric path. The inventor notes that the complex position determination code is greatly simplified if the treatment beam path 269 to the patient 230 is determined to be clear of obstructions, through use of the fiducial indicators, prior to treatment of at least one of and preferably every voxel of the tumor 220. Thus, multiple fiducial markers placed on potentially obstructing objects simplifies the code and reduces treatment related errors. Typically, treatment zones or treatment cones are determined where a treatment cone from the output nozzle system 146 to the patient 230 does not pass through any obstructions based on the current position of all potentially obstructing objects, such as a support element of the patient couch. As treatment cones overlap, the path of the treatment beam 269 and/or a path of the residual charged particle beam 267 is optionally moved from treatment cone to treatment cone without use of the imaging/treatment beam continuously as moved along an arc about the patient 230. A transform of the standard tomography algorithm thus allows physical obstructions to the imaging/treatment beam to be avoided.

Isocenterless System

The inventor notes that a fiducial marker aided imaging system, the fiducial marker aided tomography system 800, and/or the fiducial marker aided treatment system 900 are applicable in a treatment room 922 not having a treatment beam isocenter, not having a tumor isocenter, and/or is not reliant upon calculations using and/or reliant upon an isocenter. Further, the inventor notes that all positively charged particle beam treatment centers in the public view are based upon mathematical systems using an isocenter for calculations of beam position and/or treatment position and that the fiducial marker aided imaging and treatment systems described herein do not need an isocenter and are not necessarily based upon mathematics using an isocenter, as is further described infra. In stark contrast, a defined point and/or a defined line are used as a reference position and/or a reference direction and fiducial markers are defined in space relative to the point and/or line.

Traditionally, the isocenter 263 of a gantry based charged particle cancer therapy system is a point in space about which an output nozzle rotates. In theory, the isocenter 263 is an infinitely small point in space. However, traditional gantry and nozzle systems are large and extremely heavy devices with mechanical errors associated with each element. In real life, the gantry and nozzle rotate around a central volume, not a point, and at any given position of the gantry-nozzle system, a mean or unaltered path of the treatment beam 269 passes through a portion of the central volume, but not necessarily the single point of the isocenter 263. Thus, to distinguish theory and real-life, the central volume is referred to herein as a mechanically defined isocenter volume, where under best engineering practice the isocenter has a geometric center, the isocenter 263. Further, in theory, as the gantry-nozzle system rotates around the patient, the mean or unaltered lines of the treatment beam 269 at a first and second time, preferably all times, intersect at a point, the point being the isocenter 263, which is an unknown position. However, in practice the lines pass through the mechanically identified isocenter volume 1012. The inventor notes that in all gantry supported movable nozzle systems, calculations of applied beam state, such as energy, intensity, and direction of the charged particle beam, are calculated using a mathematical assumption of the point of the isocenter 263. The inventor further notes, that as in practice the treatment beam 269 passes through the mechanically defined isocenter volume but misses the isocenter 263, an error exists between the actual treatment volume and the calculated treatment volume of the tumor 220 of the patient 230 at each point in time. The inventor still further notes that the error results in the treatment beam 269: (1) not striking a given volume of the tumor 220 with the prescribed energy and/or (2) striking tissue outside of the tumor. Mechanically, this error cannot be eliminated, only reduced. However, use of the fiducial markers and fiducial detectors, as described supra, removes the constraint of using an unknown position of the isocenter 263 to determine where the treatment beam 269 is striking to fulfill a doctor provided treatment prescription as the actual position of the patient positioning system, tumor 220, and/or patient 230 is determined using the fiducial markers and output of the fiducial detectors with no use of the isocenter 263, no assumption of an isocenter 263, and/or no spatial treatment calculation based on the isocenter 263. Rather, a physically defined point and/or line, such as the zero point 1002 and/or the zero vector 1001, in conjunction with the fiducials are used to: (1) determine position and/or orientation of objects relative to the point and/or line and/or (2) perform calculations, such as a radiation treatment plan.

Referring again to FIG. 7A and referring again to FIG. 10A, optionally and preferably, the task of determining the relative object positions 740 uses a fiducial element, such as an optical tracker, mounted in the treatment room 922, such as on the gantry or nozzle system, and calibrated to a "zero" vector 1001 of the treatment beam 269, which is defined as the path of the treatment beam when electromagnetic and/or electrostatic steering of one or more final magnets in the beam transport system 135 and/or an output nozzle system 146 attached to a terminus thereof is/are turned off. The zero vector 1001 is a path of the treatment beam 269 when the first axis controller 143, such as a vertical control, and the second axis controller 144, such as a horizontal control, of the scanning system 140 is turned off. A zero point 1002 is any point, such as a point on the zero vector 1001. Herein, without loss of generality and for clarity of presentation, the zero point 1002 is a point on the zero vector 1001 crossing a plane defined by a terminus of the nozzle of the nozzle system 146. Ultimately, the use of a zero vector 1001 and/or the zero point 1002 is a method of directly and optionally actively relating the coordinates of objects, such as moving objects and/or the patient 230 and tumor 220 thereof, in the treatment room 922 to one another; not passively relating them to an imaginary point in space such as a theoretical isocenter than cannot mechanically be implemented in practice as a point in space, but rather always as an a isocenter volume, such as an isocenter volume including the isocenter point in a well-engineered system. Examples further distinguish the isocenter based and fiducial marker based targeting system.

Example I

Figure 10B:
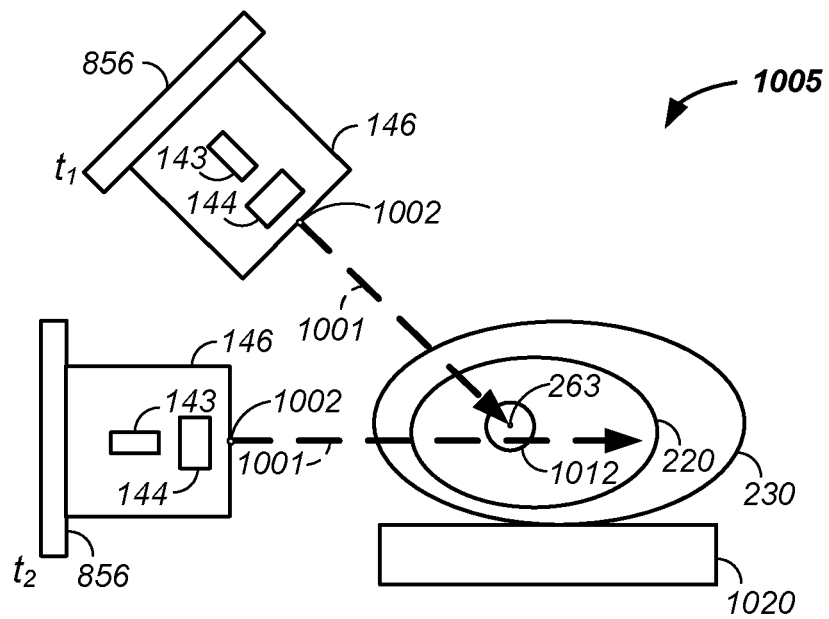

Referring now to FIG. 10B, an isocenterless system 1005 of the fiducial marker aided treatment room system 1000 of FIG. 10A is described. As illustrated, the nozzle/nozzle system 146 is positioned relative to a reference element, such as the third support element 856. The reference element is optionally a reference fiducial marker and/or a reference fiducial detector affixed to any portion of the nozzle system 146 and/or a rigid, positionally known mechanical element affixed thereto. A position of the tumor 220 of the patient 230 is also determined using fiducial markers and fiducial detectors, as described supra. As illustrated, at a first time, $t_1$, a first mean path of the treatment beam 269 passes through the isocenter 263. At a second time, $t_2$, resultant from inherent mechanical errors associated with moving the nozzle system 146, a second mean path of the treatment beam 269 does not pass through the isocenter 263. In a traditional system, this would result in a treatment volume error. However, using the fiducial marker based system, the actual position of the nozzle system 146 and the patient 230 is known at the second time, $t_2$, which allows the main controller to direct the treatment beam 269 to the targeted and prescription dictated tumor volume using the first axis controller 143, such as a vertical control, and the second axis controller 144, such as a horizontal control, of the scanning system 140. Again, since the actual position at the time of treatment is known using the fiducial marker system, mechanical errors of moving the nozzle system 146 are removed and the x/y-axes adjustments of the treatment beam 269 are made using the actual and known position of the nozzle system 146 and the tumor 220, in direct contrast to the x/y-axes adjustments made in traditional systems, which assume that the treatment beam 269 passes through the isocenter 263. In essence: (1) the x/y-axes adjustments of the traditional targeting systems are in error as the unmodified treatment beam 269 is not passing through the assumed isocenter and (2) the x/y-axes adjustments of the fiducial marker based system know the actual position of the treatment beam 269 relative to the patient 230 and the tumor 220 thereof, which allows different x/y-axes adjustments that adjust the treatment beam 269 to treat the prescribed tumor volume with the prescribed dosage.

Example II

Figure 10C:
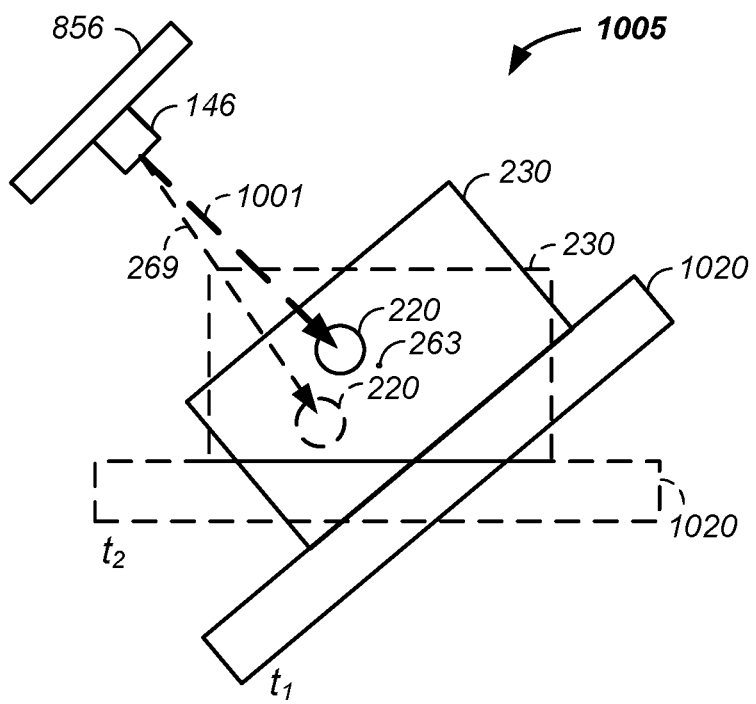

Referring now to FIG. 10C an example is provided that illustrates errors in an isocenter 263 with a fixed beamline position and a moving patient positioning system. As illustrated, at a first time, $t_1$, the mean/unaltered treatment beam path 269 passes through the tumor 220, but misses the isocenter 263. As described, supra, traditional treatment systems assume that the mean/unaltered treatment beam path 269 passes through the isocenter 263 and adjust the treatment beam to a prescribed volume of the tumor 220 for treatment, where both the assumed path through the isocenter and the adjusted path based on the isocenter are in error. In stark contrast, the fiducial marker system: (1) determines that the actual mean/unaltered treatment beam path 269 does not pass through the isocenter 263, (2) determines the actual path of the mean/unaltered treatment beam 269 relative to the tumor 220, and (3) adjusts, using a reference system such as the zero line 1001 and/or the zero point 1002, the actual mean/unaltered treatment beam 269 to strike the prescribed tissue volume using the first axis controller 143, such as a vertical control, and the second axis controller 144, such as a horizontal control, of the scanning system 140. As illustrated, at a second time, $t_2$, the mean/unaltered treatment beam path 269 again misses the isocenter 263 resulting in treatment errors in the traditional isocenter based targeting systems, but as described, the steps of: (1) determining the relative position of: (a) the mean/unaltered treatment beam 269 and (b) the patient 230 and tumor 220 thereof and (2) adjusting the determined and actual mean/unaltered treatment beam 269, relative to the tumor 220, to strike the prescribed tissue volume using the first axis controller 143, the second axis controller 144, and energy of the treatment beam 269 are repeated for the second time, $t_2$, and again through the $n^{th}$ treatment time, where n is a positive integer of at least 5, 10, 50, 100, or 500.

Referring again to FIG. 8 and FIG. 9, generally at a first time, objects, such as the patient 230, the scintillation detector system 210, an X-ray system, and the nozzle system 146 are mapped and relative positions are determined. At a second time, the position of the mapped objects is used in imaging, such as X-ray and/or proton beam imaging, and/or treatment, such as cancer treatment. Further, an isocenter is optionally used or is not used. Still further, the treatment room 922 is, due to removal of the beam isocenter knowledge constraint, optionally designed with a static or movable nozzle system 146 in conjunction with any patient positioning system along any set of axes as long as the fiducial marking system is utilized.

Figure 7B:
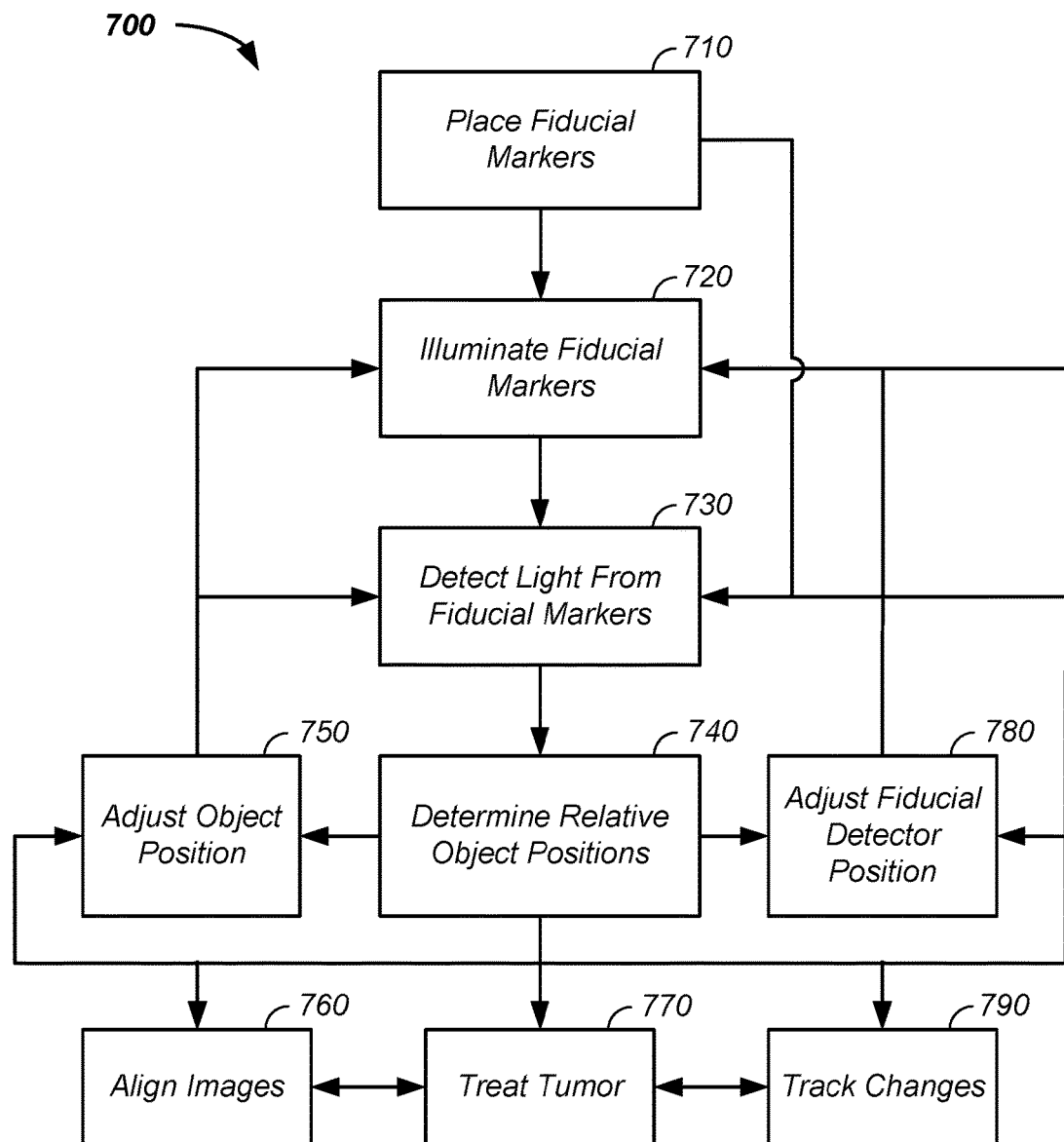

Referring now to FIG. 7B, optional uses of the fiducial marker system 700 are described. After the initial step of placing the fiducial markers 710, the fiducial markers are optionally illuminated 720, such as with the ambient light or external light as described above. Light from the fiducial markers is detected 730 and used to determine relative positions of objects 740, as described above. Thereafter, the object positions are optionally adjusted 750, such as under control of the main controller 110 and the step of illuminating the fiducial markers 720 and/or the step of detecting light from the fiducial markers 730 along with the step of determining relative object positions 740 is iteratively repeated until the objects are correctly positioned. Simultaneously or independently, fiducial detectors positions are adjusted 780 until the objects are correctly placed, such as for treatment of a particular tumor voxel. Using any of the above steps: (1) one or more images are optionally aligned 760, such as a collected X-ray image and a collected proton tomography image using the determined positions; (2) the tumor 220 is treated 770; and/or (3) changes of the tumor 220 are tracked 790 for dynamic treatment changes and/or the treatment session is recorded for subsequent analysis.

Gantry

Referring now to FIGS. 11-19, a gantry system is described.

Counterweighted Gantry System

Figure 11:
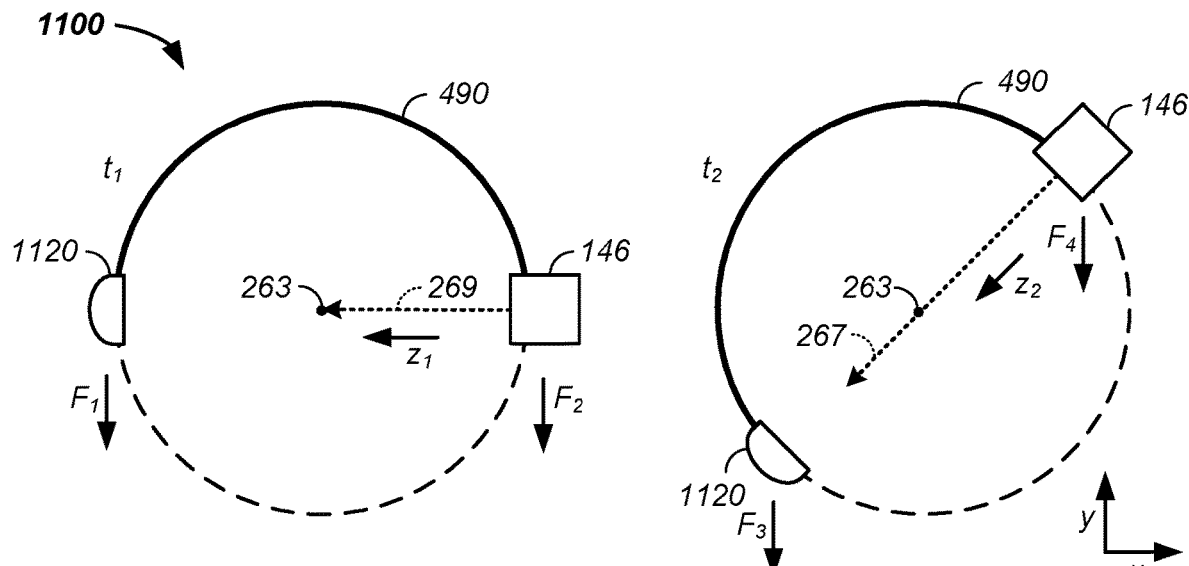
FIG. 11 illustrates a gantry counterweight system.

Referring now to FIG. 11, a counterweighted gantry system 1100 is described. In the counterweighted gantry system 1100, the gantry 490 comprises a counterweight 1120 positioned opposite a gantry rotation axis 1411 from the nozzle system 146, such as connected by an intervening rotatable gantry support 1210. Ideally, the counterweight results in no net moment of the gantry-counterweight system about the axis of rotation of the gantry. In practice, the counterweight mass and distance forces, herein all elements on one side of the axis or rotation of the gantry, is within 10, 5, 2, 1, 0.1, or 0.01 percent of the mass and distance forces of the section of the gantry on the opposite side of the axis of rotation of the gantry. Hence, as illustrated at a first time, $t_1$, a first downward force, $F_1$, resultant from all elements of the gantry 490 on a first side of the gantry rotation axis 1411 and/or isocenter 263 balances, counters, and/or equals a second downward force, $F_2$, on a second, opposite, side of the gantry rotation axis 1411 and/or isocenter 263. Stated another way, the moment of inertia, a quantity expressing a body's tendency to resist angular acceleration, of a product of masses and the square of distances of objects on a first side of the gantry rotation axis 1411 resists acceleration of a product of masses and the square of distances of objects on a second, opposite, side of the gantry rotation axis 1411. As illustrated at a second time, $t_2$, despite rotation of the gantry to a second position, a third downward force, $F_3$, and a fourth downward force, $F_4$, on opposite sides of the gantry rotation axis 1411 are still balanced. Thus, the system has no net moment of inertia. The inventor notes that the balanced system greatly reduces drive motor requirements and/or greatly enhances movement precision resultant from the smaller net forces and/or applied forces for movement of the gantry 490. Optionally, gear backlash is compensated for separately on opposite sides of a meridian position, such as where the beam path through the nozzle system 146 is aligned with gravity and/or a last movement of the rotatable beamline section 138 is against gravity, which results in a reproducible gantry position in the presence of gear slop/backlash versus gravity.

Example I

Figure 12:
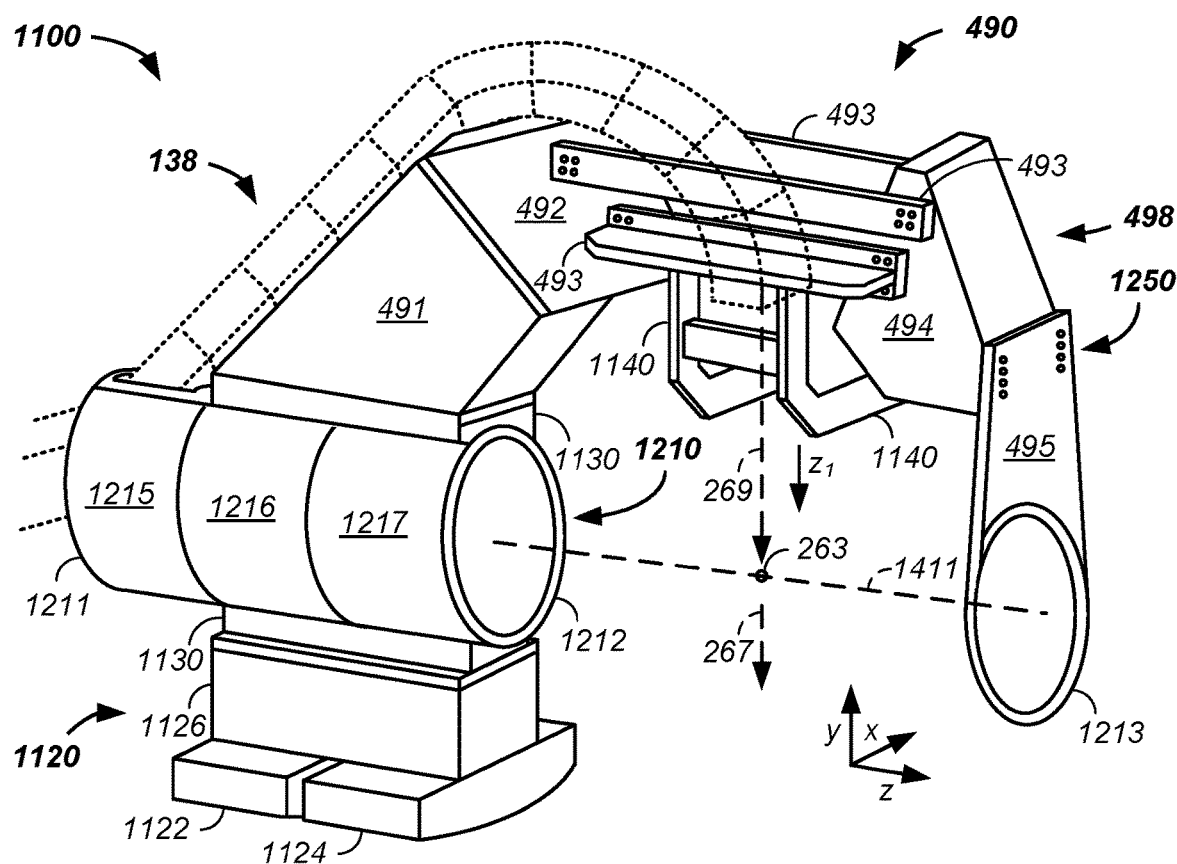
FIG. 12 illustrates a counterweighted gantry system.
Figure 13D:
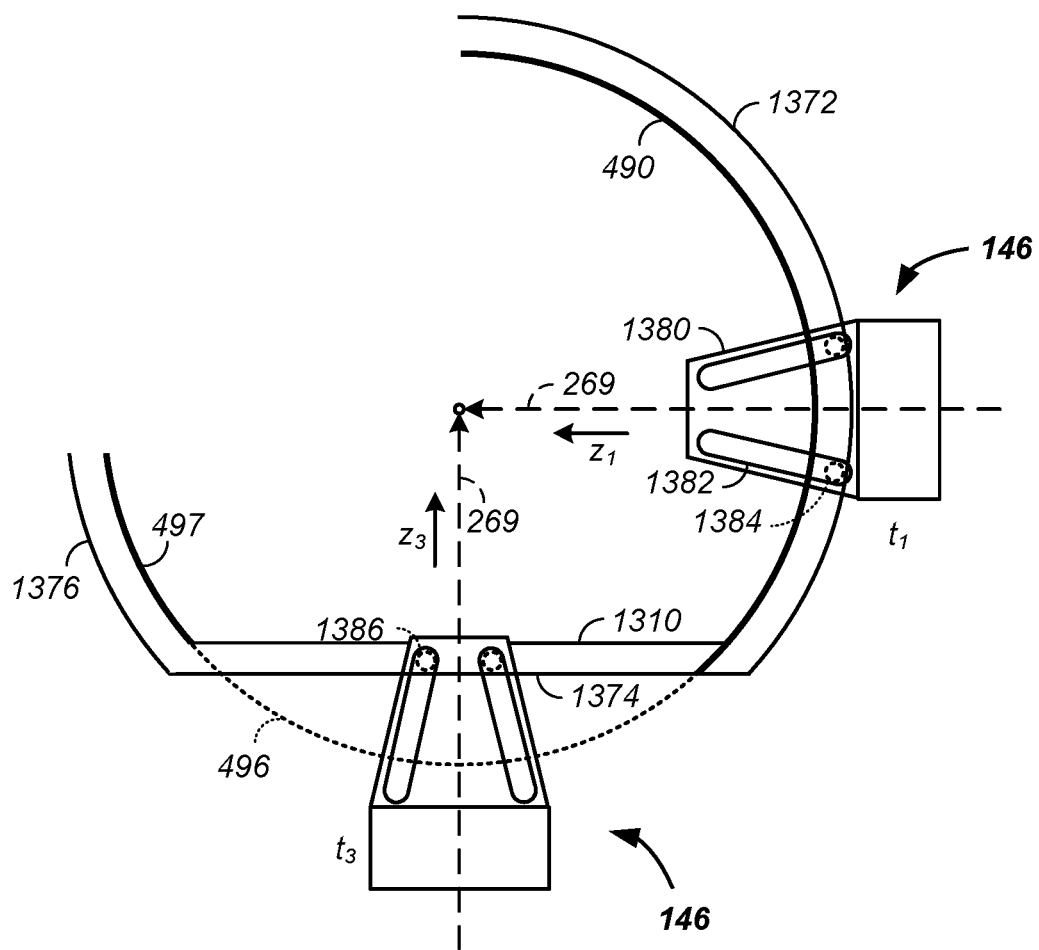
FIG. 13A illustrates a rolling floor system with a movable nozzle, FIG. 13B, a patient positioning system, FIG. 13C, and a nozzle extension track guidance system, FIG. 13D.

Referring now to FIG. 12, for clarity of presentation and without loss of generality, an example of the counterweighted gantry system 1100 is illustrated. As illustrated, first downward, inertial, rotational, and/or gravitational forces on a first side, top side as illustrated, of the gantry rotational axis 1411 counters second downward, inertial, rotational, and/or gravitational forces on a second side, bottom side as illustrated, of the gantry rotational axis 1411. To achieve the balanced forces, counterweights 1120 are added to the gantry 490, such as a first counterweight 1122, a second counterweight 1124, and/or a counterweight connector 1126 attached to a rotatable gantry support 1210. The counterweights are optionally and preferably elements of a modular installation, as further described infra.

Rotation

Still referring to FIG. 12, rotation of the gantry 490 is described. Generally, the rotatable gantry support 1210 is mounted to a support structure, not illustrated for clarity of presentation, such as with a set of bearings and/or radial ball bearings. As illustrated, a first bearing 1211, a second bearing 1212, and a third bearing 1213, guide and support movement of the gantry 490. Optionally and preferably, the set of bearings include multiple bearing elements about the rotatable gantry support 1210 on a first end of a rotatable beamline section 138 of a rotatable beamline support arm 498 of the gantry 490 and a bearing on a second end of the gantry support arm 498.

Installation

The charged particle beam system 100 is optionally built in: (1) a greenfield, which is an undeveloped or agricultural tract of land that is a potential site for industrial or urban development or (2) a brownfield, which is an urban area that has previously been built upon. Herein, a built-up brownfield refers to an existing hospital related structure comprising 2, 3, 4, 5 or more stories and a lowest level, such as a basement.

The class of particle accelerator systems for cancer therapy using protons include massive structural elements that are readily installed in a greenfield. However, installation in an existing structure, such as a basement of a building is complicated by the size of individual elements of the charged particle beam system and mass of individual elements of the charged particle beam system. For example, installation of a 300 MeV cyclotron in a four story building requires installation by crane, removal of the roof, breaking through each floor, setting by crane the 20+ ton object on the ground floor/basement and then repairing the floors and roof of the building, which is extremely disruptive, especially in a functioning hospital and/or in the presence of immune system compromised patients.

Herein, a system of installation is described, via example, where elements of the charged particle beam system 100 are installed into a built-up brownfield hospital related structure.

Example I

In the installation system, all elements of the charged particle beam system 100 are optionally and preferably:
  less than 5,000, 10,000, 15,000, 25,000, or 35,000 pounds;
  transportable on a standard eighteen wheel semi-truck or smaller truck;
  moved through the built-up brownfield hospital related structure using equipment passable through standard hallways and/or elevators; and/or
  assembled in a basement and/or ground level of the built-up brownfield hospital related structure.

For clarity of presentation and without loss of generality, transport of several subsystems of the charged particle beam system 100 are further described. A first subsystem, the accelerator and/or beam transport line, is moved as individual magnet assemblies, such as the main bending magnets 132. A second subsystem, the gantry 490, is divided for movement into a first gantry support section 491, a second gantry support section 492, a third gantry support section 493, a fourth gantry support section 494, and a fifth gantry support section 495, as further described infra. A third subsystem, the rotatable gantry support 1210, is optionally and preferably assembled from multiple sub-units, such as a first rotatable gantry support element 1215, a second rotatable gantry support element 1216, and a third rotatable gantry support element 1217. A fourth subsystem, the gantry support, is optionally and preferably a free-standing system, which, without a requirement of wall mounting, further described infra, is optionally and preferably assembled in sections, such as modular sections. Stated again, an existing brownfield wall is not a mechanical element required to resist gravitational forces related to the gantry, as further described infra, so the gantry support structures are transportable stands. Generally, movement of sub-systems as sub-assembly components reduces the mass of individual elements to a weight and mass movable through the hallways and/or elevators.

Example II

In a second example, one or more the top five largest components of the charged particle beam system 100 are transported through an elevator shaft and/or an elevator car of an elevator. Herein, an elevator comprises: (1) a standard existing brownfield passenger in the hospital related facility, such as a standard passenger elevator with capacities ranging from 1,000 to 6,000 pounds in 500 pound increments or (2) a standard freight elevator, such as a Class A general freight loading elevator designed to carry goods and not passengers, though passenger transport is not illegal. In each case, the elevators' capacity is related to the available floor space and associated elevator shaft horizontal cross-section dimension. In both cases, the load is handled on and off the car platform manually or by means of hand trucks.

Example III

Figures 16A, 16B:
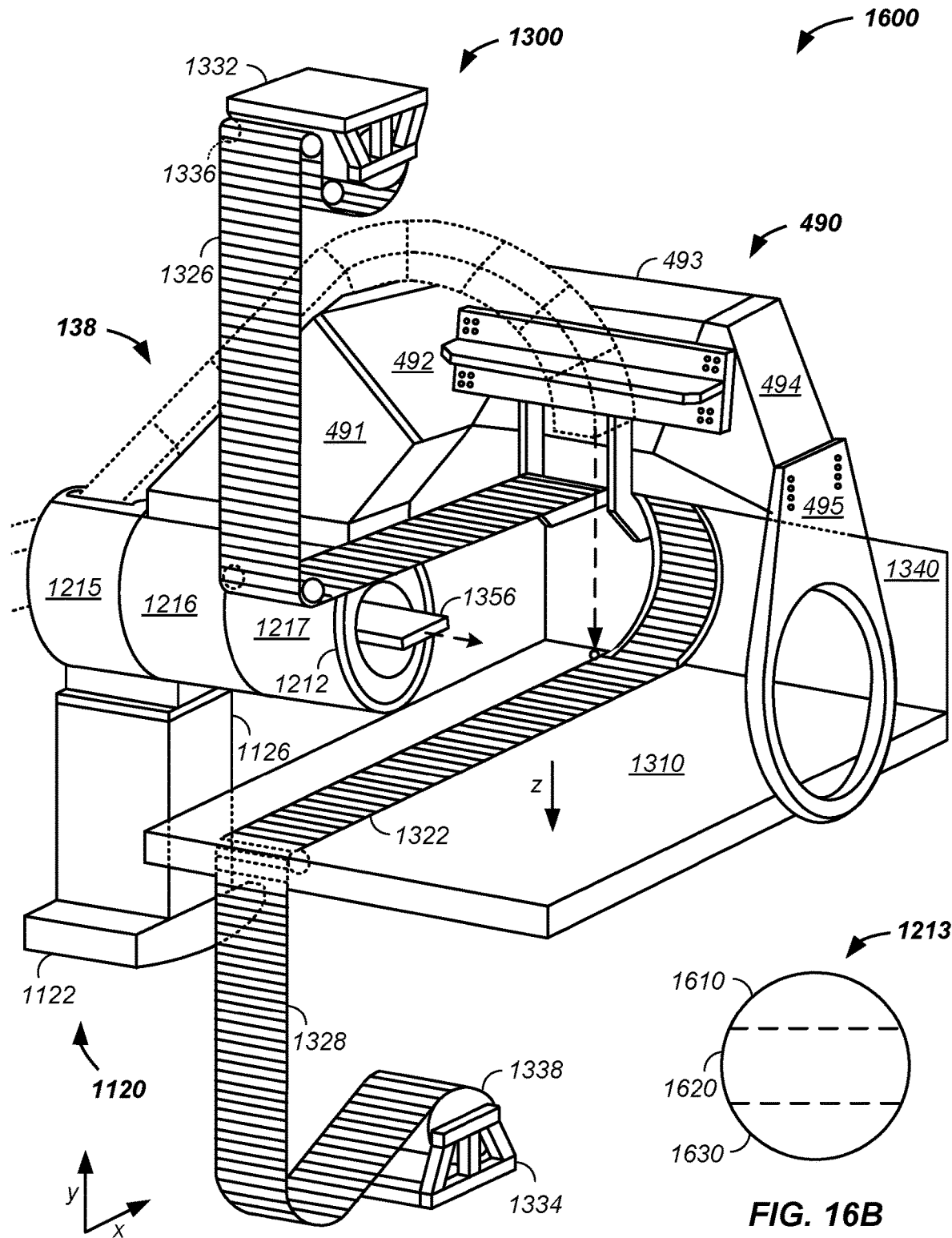
FIG. 16A illustrates a combined gantry-rolling floor system and FIG. 16B illustrates a segmented bearing.

In some designs of the charged particle beam system 100, a bearing is used to guide and support movement of the gantry 490. One or more bearings, such as the third bearing 1213, are quite large to allow walking access to the treatment room through the bearing, such as for use with a gantry rotatable 360 degrees about the gantry axis of rotation, and have a diameter exceeding a horizontal cross-section dimension of an elevator shaft. Referring now to FIG. 16B, an optional configuration of the third bearing 1213 is illustrated, where the third bearing is assembled from two or more components. As illustrated, the third bearing 1213 comprises a first bearing section 1610, a second bearing section 1620, and a third bearing section 1630, where splitting the bearing into sections allows transport of a large bearing, such as greater than 8, 9, 10, 11, or 12 foot in diameter, through a standard hospital hallway and/or standard passenger elevator shaft, such as via the elevator car or a crane transport operating the in the elevator shaft. As illustrated, the third bearing 1213 comprises a first circular segment or a first arc-to-chord section, a second circular segment or a second arc-to chord section, and a middle section connecting, such as via welding and/or bolting, the first circular segment and the second circular segment.

Optionally and preferably, one or more cranes and/or overhead transport systems are permanently installed in and/or about the charged particle beam system 100, such as in and/or about the treatment room, gantry, and/or accelerator.

Example I

In a first example, as illustrated, a section of the gantry 490 supporting the rotational beamline section 138 and the nozzle system 146 is optionally and preferably assembled from multiple sub-units, such as a first gantry support section 491, a second gantry support section 492, a third gantry support section 493, a fourth gantry support section 494, and a fifth gantry support section 495. Several of the sections are further described. The first gantry section 491 couples to the rotatable gantry support 1210 using a gantry connector section 1130. The third gantry section 493, combined with the fourth gantry section 494 and the fifth gantry section 495, provides an aperture through which the rotational beamline section 138 passes and/or contains the nozzle system 146.

Example II

In a second example, the rotatable gantry support 1210 is optionally and preferably assembled from multiple sub-units, such as a first rotatable gantry support element 1215, a second rotatable gantry support element 1216, and a third rotatable gantry support element 1217.

Example III

In a third example, the counterweighted gantry system 1100 is readily installed into an existing facility. As further described using FIGS. 17-19 below, the counterweighted gantry system 1100 is free standing, so the structure is optionally and preferably a bolt together assembly 1250, which allows installation of the unit into an existing structure.

Gantry Rotation

Referring still to FIG. 12 and referring now to FIGS. 13(A-D), rotation of the gantry 490 relative to a rolling floor system 1300, also referred to as a segmented floor, is described, where the segmented sections allow for the floor system to contour to a curved surface, change direction around a roller, and/or spool as further described infra.

Referring still to FIG. 12, as the rotatable beamline support arm 498 of the gantry 490 rotates around the gantry rotation axis 1411, the rotatable beamline section 138 of the beam transport system 135 is moved around the gantry rotation axis 1411 and the nozzle system 146, illustrated in FIG. 13 for clarity of presentation, extending from the aperture through the third gantry section 493 rotates around the tumor 220, the patient 230, the gantry rotation axis 1411, and/or the isocenter 263. Referring now to FIG. 13A, the nozzle system 146, extending from the aperture through the third gantry section 493, illustrated in FIG. 12, is illustrated in a first position, a horizontal position, through a movable floor, described infra. Referring now to FIG. 13B, for clarity of presentation, the nozzle system 146 is rotated from the first position illustrated in FIG. 13A at a first time, $t_1$, to a second position illustrated in FIG. 12 at a second time, $t_2$, using the gantry 490 Referring still to FIG. 13A and FIG. 13B, the gantry 490, optionally and preferably, rotates the nozzle system 146 from a position under the patient 230 through a floor 1310, as described infra, along a curved wall, as described infra, and through a ceiling area, as described infra.

Rolling Floor

Referring still to FIG. 13A, the rolling floor system 1300, also referred to as a rolling wall-floor system, is further described. The rolling floor system 1300 comprises a rolling floor 1320, such as a segmented floor. As illustrated, the rolling floor 1320 comprises sections moving along/past a flat floor section 1322, such as inset into the floor 1310; a wall section 1324, such as along/inset into a curved wall section 1340 of a wall; an upper spooler section 1326, such as into/around/wound around an upper spooler 1332 or upper spool; and a lower spooling section 1328, such as into/around a lower spooler 1334 or lower spool. Herein, a spooler is a device, such as a cylinder, on which an object, such as the segmented floor is wound. A floor movement system 1330 optionally includes one or more spoolers, such as the upper spooler 1332, the lower spooler 1334, one or more rollers 1336, and/or one or more spools 1338.

Referring still to FIG. 13A and now to FIG. 13C, the rolling floor system 1300 is described relative to a patient positioning system 1350. Generally, the patient positioning system 1350 comprises multiple degrees of freedom for positioning the patient 230 in an x, y, z position with yaw, tilt, and/or roll, and/or as a function of patient rotation and time. The floor section 1322 of the rolling floor system 1300, through which the nozzle system 146 penetrates, passes underneath the tumor 220 of the patient 230 when the patient 230, positioned by the patient positioning system 1350, is in a treatment position, such as in the treatment beam path 269. Similarly, the gantry 490 rotates the nozzle system 146 around the patient 230, such as along a concave or curved wall section 1340 of the wall and rotates the nozzle system 146 in an arc above the patient 230 with continued rotation of the gantry 490 and spooling of the linked/physically clocked rolling floor system 1300.

The inventor notes that existing gantries, to allow movement of the gantry under the patient, position the patient in space, such as along a plank into a middle of an open chamber ten feet or more off of the floor, which is distressful to the patient and prevents an operator from approaching the patient during treatment. In stark contrast, referring now to FIG. 13A and FIG. 13D, the rolling floor system 1300 allows presence of the floor 1310 without a gap and/or hole in the floor through which a person could fall and still allows the gantry 490 to rotate under the patient 230. More particularly, a nozzle extension 1380 integrated into the nozzle system 146 comprises a set of guides 1382 and a set of rollers 1384, where the rollers are in a track 1372 that transitions from a curved section corresponding to the curved wall to a flat section corresponding to the flat floor 1310. When the gantry 490 positions the nozzle system 146 and the corresponding co-rotating/clocked floor system 1300 along the curved wall 1340, the rollers 1384 are at a first track position and a first guide position, such as illustrated at a first time, $t_1$. As the gantry 490 rotates past a plane of the floor 1310 toward a bottom position at a third time, $t_3$, the rollers remain in the track, but slide up the guides 1382 to a floor position 1386. Thus, the patient 230 and/or the operator have a continuous floor 1310 when the nozzle system 146 penetrates through the floor with rotation of the gantry 490 under a plane of the floor as the flat section 1322 of the rolling floor continuously fills floor space vacated by the moving nozzle system 146 and opens up floor space for the rotating nozzle system 146 moving with the rotatable beamline support arm 498 of the gantry 490. Optionally, the nozzle system 146 continues rotation around the patient 220, such as back up through the floor 1310 along an upward curved path 497 with a corresponding upward curved track section 1376. Similarly, optionally the nozzle system 146 rotates 360 degrees around the patient 230 during use.

Patient Positioning/Imaging

Figure 14:
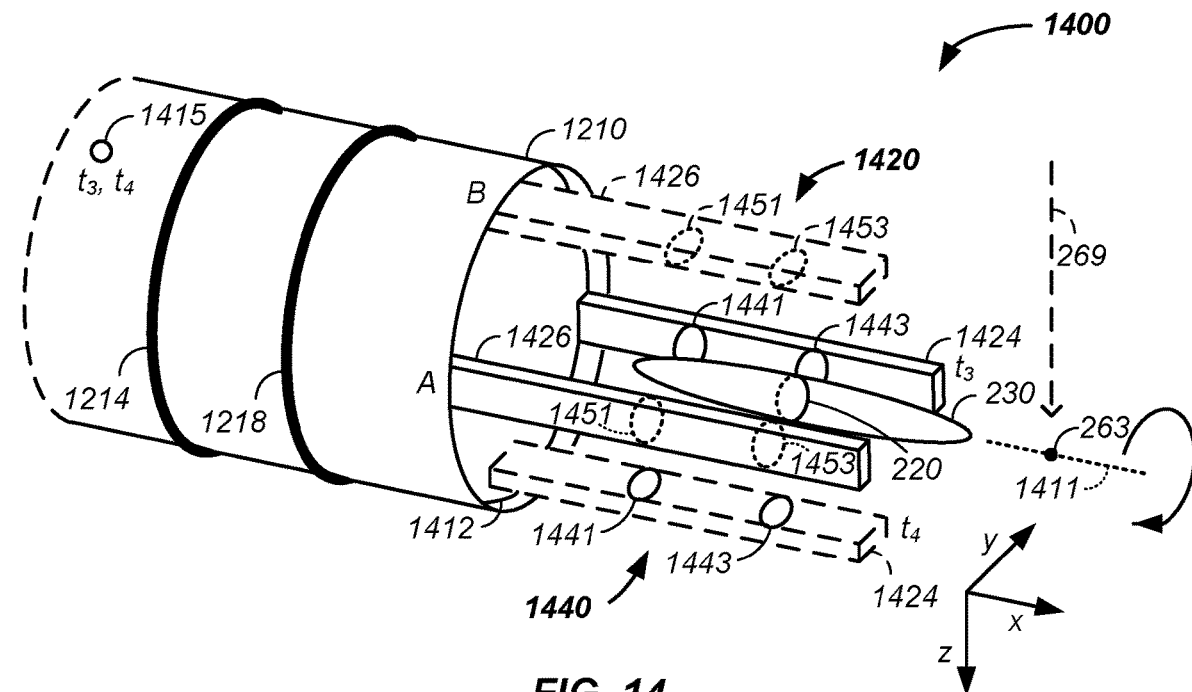
FIG. 14 illustrates a hybrid cancer-treatment imaging system.
Figure 15:
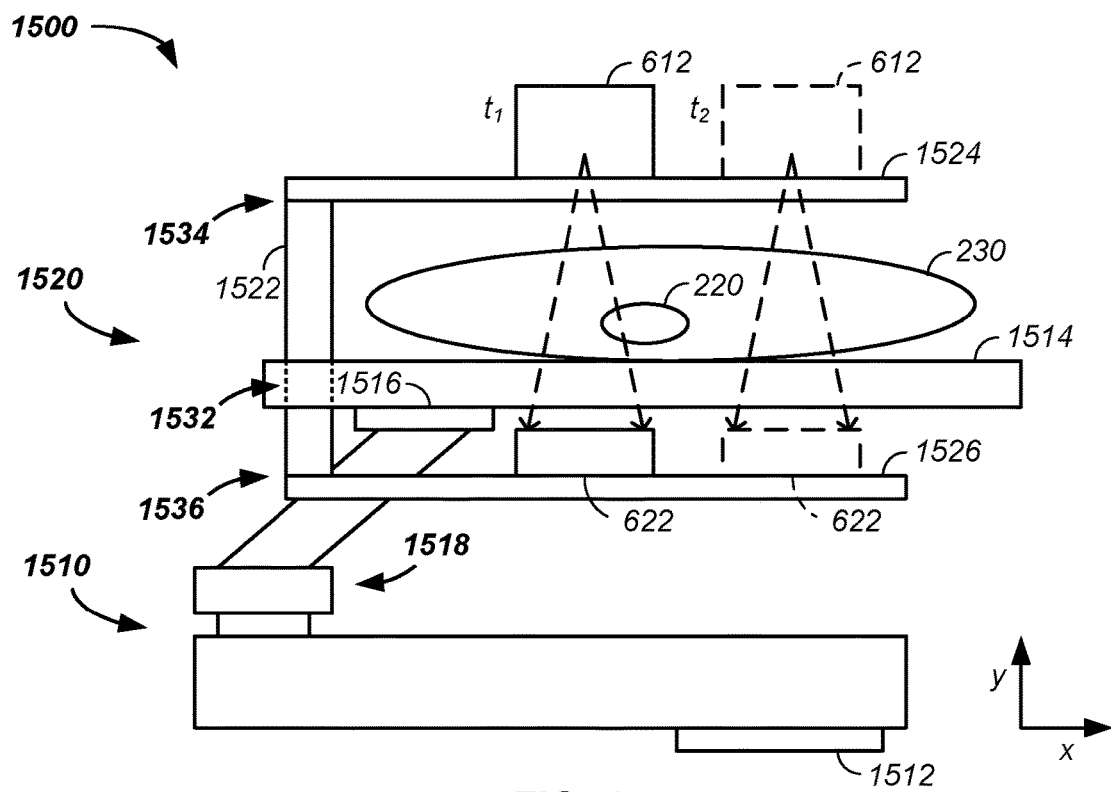
FIG. 15 illustrates a combined patient positioning system-imaging system.

Referring now to FIG. 13A, FIG. 14, and FIG. 15, patient imaging is further described.

Referring now to FIG. 13A, a hybrid cancer treatment-imaging system 1400 is illustrated, where the imaging system rotates on an optionally and preferably independently rotatable mount from the second bearing 1212 and/or the rotatable gantry support 1210. Referring now to FIG. 14, an example of the hybrid cancer treatment-imaging system 1400 is illustrated. Generally, the gantry 490, which optionally and preferably supports the nozzle system 146, rotates around the tumor 220 and/or an isocenter 263. As illustrated, the gantry 490 rotates about a gantry rotation axis 1411, such as using the rotatable gantry support 1210. In one case, the gantry 490 is supported on a first end by a first buttress, wall, or support and on a second end by a second buttress, wall, or support. However, as further described, infra, preferably the gantry 490 is supported using floor based mounts. A fourth optional rotation track 1214 or bearing and a fifth optional rotation track 1218 or bearing coupling the rotatable gantry support and the gantry 490 are illustrated, where the rotation tracks are any mechanical connection. Referring again to FIG. 12, for clarity of presentation, only a portion of the gantry 490 is illustrated to provide visualization of a supported rotational beamline section 138 of the beam transport system 135 or a section of the beamline between the synchrotron 130 and the patient 230. To further clarify, the gantry 490 is illustrated, at one moment in time, supporting the nozzle system 146 of the beam transport system 135 in an orientation resulting in a vertical and downward vector of the treatment beam 269. As the rotatable gantry support 1210 rotates, the gantry 490, the rotational beamline section 138 of the beam transport line 135, the nozzle system 146 and the treatment beam 269 rotate about the gantry rotation axis 1411, forming a set of treatment beam vectors originating at circumferential positions about tumor 220 or isocentre 263 and passing through the tumor 220. Optionally, an X-ray beam path, from an X-ray source, runs through and moves with the nozzle system 146 parallel to the treatment beam 269. Prior to, concurrently with, intermittently with, and/or after the tumor 220 is treated with the set of treatment beam vectors, one or more elements of the imaging system 170 image the tumor 220 of the patient 230.

Referring again to FIG. 14, the hybrid cancer treatment-imaging system 1400 is illustrated with an optional set of rails 1420 and an optional rotatable imaging system support 1412 that rotates the set of rails 1420, where the set of rails 1420 optionally includes n rails where n is a positive integer. Elements of the set of rails 1420 support elements of the imaging system 170, the patient 230, and/or a patient positioning system. The rotatable imaging system support 1412 is optionally concentric with the rotatable gantry support 1210. The rotatable gantry support 1210 and the rotatable imaging system support 1412 optionally: co-rotate, rotate at the same rotation rate, rotate at different rates, or rotate independently. A reference point 1415 is used to illustrate the case of the rotatable gantry support 1210 remaining in a fixed position, such as a treatment position at a third time, $t_3$, and a fourth time, $t_4$, while the rotatable imaging system support 1412 rotates the set of rails 1420.

Still referring to FIG. 14, any rail of the set of rails optionally rotates circumferentially around the x-axis, as further described infra. For instance, the first rail 1422 is optionally rotated as a function of time with the gantry 490, such as on an opposite side of the nozzle system 146 relative to the tumor 220 of the patient 230.

Still referring to FIG. 14, a first rail of the set of rails 1420 is optionally retracted at a first time, $t_1$, and extended at a second time, $t_2$, as is any of the set of rails. Further, any of the set of rails 1420 is optionally used to position a source or a detector at any given extension/retraction point. A second rail 1424 and a third rail 1426 of the set of rails 1420 are illustrated. Generally, the second rail 1424 and the third rail 1426 are positioned on opposite sides of the patient 230, such as a sinister side and a dexter side of the patient 230. Generally, the second rail 1424, also referred to as a source side rail, positions an imaging source system element and the third rail 1426, also referred to as a detector side rail, positions an imaging detector system element on opposite sides of the patient 230. Optionally and preferably, the second rail 1424 and the third rail 1426 extend and retract together, which keeps a source element mounted, directly or indirectly, on the second rail 1424 opposite the patient 230 from a detector element mounted, directly or indirectly, on the third rail 1426. Optionally, the second rail 1424 and the third rail 1426 position positron emission detectors for monitoring emissions from the tumor 220 and/or the patient 230, as further described infra.

Still referring to FIG. 14, a rotational imaging system 1440 is described. For example, the second rail 1424 is illustrated with: (1) a first source system element 1441 of a first imaging system, or first imaging system type, at a first extension position of the second rail 1424, which is optically coupled with a first detector system element 1451 of the first imaging system on the third rail 1426 and (2) a second source system element 1443 of a second imaging system, or second imaging system type, at a second extension position of the second rail 1424, which is optically coupled with a second detector system element 1453 of the second imaging system on the third rail 1426, which allows the first imaging system to image the patient 230 in a treatment position and, after translation of the first rail 1424 and the second rail 1426, the second imaging system to image the patient 230 in the patient's treatment position. Optionally the first imaging system or primary imaging system and the second imaging system or secondary imaging system are supplemented with a tertiary imaging system, which uses any imaging technology. Optionally, first signals from the first imaging system are fused with second signals from the second imaging system to: (1) form a hybrid image; (2) correct an image; and/or (3) form a first image using the first signals and modified using the second signals or vise-versa.

Still referring to FIG. 14, the second rail 1424 and third rail 1426 are optionally alternately translated inward and outward relative to the patient, such as away from the first buttress and toward the first buttress, as described infra. In a first case, the second rail 1424 and the third rail 1426 extend outward on either side of the patient, as illustrated in FIG. 14. Further, in the first case the patient 230 is optionally maintained in a treatment position, such as in a constrained laying position that is not changed between imaging and treatment with the treatment beam 269. In a second case, the patient 230 is relatively translated between the second rail 1424 and the third rail 1426. In the second case, the patient is optionally imaged out of the treatment beam path 269. Further, in the second case the patient 230 is optionally maintained in a treatment orientation, such as in a constrained laying position that is not changed until after the patient is translated back into a treatment position and treated. In a third case, the second rail 1424 and the third rail 1426 are translated away from the rotatable gantry support 1210 and/or the patient 230 is translated toward the rotatable gantry support 1210 to yield movement of the patient 230 relative to one or more elements of the first imaging system type or second imaging system type. Optionally, images using at least one imaging system type, such as the first imaging system type, are collected as a function of the described relative movement of the patient 230, such as along the x-axis and/or as a function of rotation of the first imaging system type and the second imaging system type around the x-axis, where the first imaging type and second imaging system type use differing types of sources, use differing types of detectors, are generally thought of as distinct by those skilled in the art, and/or have differing units of measure. Optionally, the source is emissions from the body, such as a radioactive emission, decay, and/or gamma ray emission, and the second rail 1424 and the third rail 1426 position and/or translate one or more emission detectors, such as a first positron emission detector on a first side of the tumor 220 and a second positron emission detector on an opposite side of the tumor 220.

Example I

Still referring to FIG. 14, an example of the hybrid cancer treatment-rotational imaging system is illustrated. In one example of the hybrid cancer treatment-rotational imaging system, the second rail 1424 and third rail 1426 are optionally circumferentially rotated around the patient 230, such as after relative translation of the second rail 1424 and third rail 1426 to opposite sides of the patient 230. As illustrated, the second rail 1424 and third rail 1426 are affixed to the rotatable imaging system support 1412, which optionally rotates independently of the rotatable gantry support 1210. As illustrated, the first source system element 1441 of the first imaging system, such as a two-dimensional X-ray imaging system, affixed to the second rail 1424 and the first detector system element 1451 collect a series of preferably digital images, preferably two-dimensional images, as a function of co-rotation of the second rail 1424 and the third rail 1426 around the tumor 220 of the patient 230, which is positioned along the gantry rotation axis 1411 and/or about the isocenter 263 of the charged particle beam line in a treatment room. As a function of rotation of the rotatable imaging system support 1412 about the gantry rotation axis 1411, two-dimensional images are generated, which are combined to form a three-dimensional image, such as in tomographic imaging. Optionally, collection of the two-dimensional images for subsequent tomographic reconstruction are collected: (1) with the patient in a constrained treatment position, (2) while the charged particle beam system 100 is treating the tumor 220 of the patient 230 with the treatment beam 269, (3) during positive charged particle beam tomographic imaging, and/or (4) along an imaging set of angles rotationally offset from a set of treatment angles during rotation of the gantry 490 and/or rotation of the patient 230, such as on a patient positioning element of a patient positioning system.

Optionally, one or more of the imaging systems described herein monitor treatment of the tumor 220 and/or are used as feedback to control the treatment of the tumor 220 by the treatment beam 269.

Referring to FIG. 15, a combined patient positioning system-imaging system 1500 is described. Generally, the combined patient positioning system-imaging system 1500 comprises a joint imaging/patient positioning system 1510 and a translation/rotation imaging system 1520. The joint imaging/patient positioning system 1510 co-moves or jointly moves the translation/rotation imaging system 1520 and the patient 230 as both a patient support 1514 and the translation/rotation imaging system 1520 are attached to an end of a robotic arm used to position the patient relative to a proton treatment beam, as further described infra.

Still referring to FIG. 15, the joint imaging/patient positioning system 1500 is further described. The joint imaging/patient positioning system 1510 allows movement of the patient 230 along one or more of: an x-axis, a y-axis, and a z-axis. Further, the patient positioning system 1510 allows yaw, tilt, and roll of the patient as well as rotation of the patient 230 relative to a point in space, such as one or more rotation axes passing through the joint imaging/patient positioning system 1510 and/or an isocenter point 263 of a treatment room. For clarity of presentation and without loss of generality, all permutations and combinations of patient movement relative to a treatment proton beam line are illustrated with a base unit 1512, such as affixed to a floor or wall of the treatment room; an attachment unit 1516, of the translation/rotation imaging system 1520; and a multi-element robotic arm section 1518 connecting the base unit 1512 and the attachment unit 1516.

Still referring to FIG. 15, the translation aspect of the translation/rotation imaging system 1520 is further described. The translation/rotation imaging system 1520 comprises a ring or a source-detector rotational positioning unit 1522, an imaging system source support 1524, a first imaging source 612, an imaging system detector support 1526, and a first detector array 622. The imaging system source support 1524 is used to move a source, such as the first imaging source 612, of the translation/rotation imaging system 1520 and the detector support 1526 is used to move a detector, such as the first detector array 622, of the translation/rotation imaging system 1520. For clarity of presentation and without loss of generality, the first imaging source 612 is used to represent any one or more of the imaging sources described herein and the first detector array 622 is used to represent one or more of the imaging detectors described herein. As illustrated, in a first case, the imaging source 612, such as an X-ray source, moves past the patient 230 on the imaging system source support 1524, such as under control of the main controller 110 directing a motor or drive to move the imaging source 612 along a guide, drive system, or rail. In the illustrated case, the source-detector rotational positioning unit 1522 is connected to an element, such as the patient support 1514, that is positioned relative to the nozzle system 146 and/or treatment beam path 269. However, the source-detector rotational positioning unit 1522 is optionally connected to the attachment element 1516 or the rotatable imaging system support 1412. Optionally, the patient support 1514 uses a first electromechanical interface 1532 that moves the translation/rotation imaging system 1520 relative to the patient support 1514 and hence the patient 230. Optionally, the first electromechanical interface 1532 is a solid/connected element and a second electromechanical interface 1534 and a third electromechanical interface 1536 are used to move the imaging system source support 1524 and the imaging system detector support 1526, respectively, relative to the patient support 1514 and hence the patient 230.

Referring again to FIG. 14 and still referring to FIG. 15, generally, any mechanical/electromechanical system is used to connect the source-detector rotational positioning unit 1522 to the attachment unit 1516 and/or an intervening connector, such as the patient support 1514 or a secondary attachment unit 1540, as further described infra. Notably, the patient support 1514 and/or patient 230 optionally pass into and/or through an aperture through the source-detector rotational positioning unit 1522. In practice, any of the first through third electromechanical connectors 1532, 1534, 1536 function to move a first element relative to a second element, such as along a track/rail and/or any mechanically guiding system, such as driven by a belt, gear, motor, and/or any motion driving source/system.

Still referring to FIG. 15, optionally, the imaging system source support 1524 extends/retracts away/toward the attachment unit, which results in translation of the X-ray source past the patient 230. Similarly, as illustrated, the first detector array 622, such as an two-dimensional X-ray detector panel, moves past the patient on the imaging system detector support 1526, such as under control of the main controller directing a motor or drive to move the first detector array 622, such as an X-ray detector panel, along a guide, drive system, or rail. Optionally, the imaging system detector support 1526 extends/retracts away/toward the source-detector rotational positioning unit 1522, which results in translation of the X-ray detector past the patient 230.

Referring again to FIG. 15, the interface of the translation/rotation imaging system 1520 and the patient support 1514 to the joint imaging/patient positioning system 1510 is described. Essentially, as the attachment unit 1516 of the joint imaging/patient positioning system 1510 is directly connected/physically static relative to both the translation/rotation imaging system 1520 and the patient support 1514, as the imaging/patient positioning system 1510 moves the patient support 1514 the entire translation/rotation imaging system 1520 moves with the patient support. Thus, no net difference in position between the translation/rotation imaging system 1520 and the patient 230 or patient support 1514 results as the joint imaging/patient positioning system 1510 positions the patient 230 relative to the positively charged particle tumor treatment beam 269 and/or nozzle system 146. However, individual elements of the translation/rotation imaging system 1520 are allowed to move relative to the patient 230, such as in the translation movements described above and the rotation movements described below.

Referring still to FIG. 15, the imaging source 612 and the first detector array 622 rotate around the patient in and out of the page. More precisely, both: (1) the first imaging source 612 and the imaging system source support 1524 and (2) the first detector array 622 and the imaging system detector support 1526, while connected to the source-detector positioning unit, rotate about patient support 1514 and the patient 230. Just as illustrated in FIG. 14, all of: (1) the first imaging source 612, (2) the imaging system source support 1524, (3) the first detector array 622, and (4) the imaging system detector support 1526, optionally and preferably rotate around the patient 230 independent of movement of the patient, relative to a current position of the positively charged particle treatment beam passing through the nozzle system 146, using the imaging/patient positioning system 1510. Generally, the first imaging source 612 and the first detector array 622 are positioned at any position from 0 to 360 degrees around the patient 230 and/or the first imaging source 612 and the first detector array 622 are positioned at any translation position relative to a longitudinal axis of the patient 230, such as from head to toe.

Integrated Gantry, Patient Positioning, Imaging, and Rolling Floor System

Referring now to FIG. 16A, a gantry superstructure 1600 is illustrated. For clarity of presentation and without loss of generality, several examples are used to further described the gantry superstructure 1600.

Example I

In a first example, the counterweighted gantry system 1100 and the rolling floor system 1300 are illustrated relative to one another. In this example, the patient positioning system 1350 is illustrated using the hybrid cancer treatment-imaging system 1400 described, supra, where a patient platform/support 1356 is mounted onto/inside the second bearing 1212, such as on a nonrotating or minimally rotating element of the rotatable imaging system support 1412, where the patient platform 1356 is extendable over the flat section 1322 of the rolling floor system 1300. Further, an optional single element counterweight extension 1126 is illustrated, such as optionally affixed to the first counterweight 1122.

Example II

In a second example, the gantry superstructure 1600 is configured as a three hundred sixty degree rotatable gantry system. More particularly, in this example the fifth gantry support section 495 is not used or present, which results in a cantilevered gantry arm supported on only a first end, such as the first gantry support section 491 connected to the rotatable gantry support 1210. In this system, the counterweight system 1120, connected to a second and preferably opposite side of the rotatable gantry support 1210, functions as a counterweight to the gantry support arm 498 and elements supported by the gantry support arm 498, such as the rotatable beamline section 138 and the nozzle system 146. The cantilevered gantry system is further rotatable about the gantry rotation axis 1411, which is optionally and preferably horizontal or within 1, 2, 3, 5, 10, or 25 degrees of horizontal.

Example III

In a third example of the gantry superstructure 1600, the cantilevered three hundred sixty degree rotatable gantry system is supported on a single side of the patient position, such as via use of the first pier 1810. The first pier 1810, further described infra, optionally supports a first floor section 1312, of the floor 1310, to the rotatable gantry support side of a beamline path swept by the treatment beam 269 during rotation of the rotatable gantry support arm 498 through an arc of 10 to 360 degrees. The support of the first floor section 1312 passes through at least a portion of the rotatable gantry support 1210 and/or the second bearing 1212 to allow full rotation of the gantry support arm 498, such as through an arc exceeding 180, 200, 300, or 359 degrees. More particularly, as the first pier 1810 and supports for the first floor section 1312 pass through the rotatable gantry support 1210, the mechanical supports do not intersect a volume swept by the rotatable gantry support arm 498 or a side of the rotatable gantry support arm 498, such as the inner side of the rotatable gantry support arm 498 relative to a central point about which the rotatable gantry support arm 498 rotates. The second floor section 1314, of the floor 1310, outside of the volume swept by the rotatable gantry support arm 498, is optionally supported by the second pier 1820, further described infra. Combined, the first floor section 1312 and the second floor section 1314, such as on opposite sides of the flat floor section 1322 of the rolling floor 1320, are supported by support structures, such as the first pier 1810 and the second pier 1820, that do not intersect the volume defined by the gantry support arm 498 at any position of a 360 degree rotation.

Example IV

In a fourth example, access to the cantilevered three hundred sixty degree rotatable gantry system with the split floor is described. The inventor notes that if a three hundred sixty degree rotatable gantry is supported on both ends of a gantry arm arc, the arc sweeps out a volume with a hole in the middle, such as sweeping out an egg white volume with an egg yolk as the enclosed, non-gantry arm contacted volume. As a result, any entranceway for an average sized adult into the treatment area, the yolk in the analogy, is either temporarily impeded by the gantry support arm 498 or is through an aperture in a bearing, such as through the second bearing 1212 or third bearing 1213. Temporary impedance of human exit, such as by a multi-ton gantry support arm 498, is a fire hazard and/or safety hazard. However, the cantilevered 360 degree rotatable gantry system described herein, without use of a bearing and support on one side/end of the gantry support arm 498, such as the third bearing 1213 or fifth gantry section 495 as illustrated, allows direct access to the entire floor 1310, such as via any access point/doorway to the second floor section 1314 with subsequent passage across the rolling floor 1320, the egg white by analogy, to the first floor section 1312, the egg yolk by analogy.

Example V

In a fifth example, the patient positioning system 1350 is mounted to the second floor section 1314 to reduce mass positioned on the first floor section 1312, supported through the rotatable gantry support 1210.

Example VI

In a sixth example, the accelerator is positioned below the gantry 490, which reduces the footprint of the combined accelerator and gantry. Optionally, the beam transport system 135 from the accelerator, such as the synchrotron 130 positioned below the gantry 490, transports the positively charged particles upwards and through a section of the rotatable gantry support 1210. Optionally, the volume swept by the rotatable gantry arm 498 passed within a volume radially circumferentially encircled by the synchrotron 130, which further reduces space and still give full access to all elements of the synchrotron 130 and the gantry 490.

Example VII

In a seventh example, the rolling floor 1320 forms a continuous loop in the cantilevered three hundred sixty degree rotatable gantry system.

Example VIII

In an eighth example, an actual position of the cantilevered rotatable gantry system is monitored, determined, and/or confirmed using the fiducial indicators 2040, described, infra, such as a fiducial source and/or a fiducial detector/marker placed on any section of the gantry 490, patient positioning system 1350, and/or patient 230.

Floor Force Directed Gantry System

Figure 17:
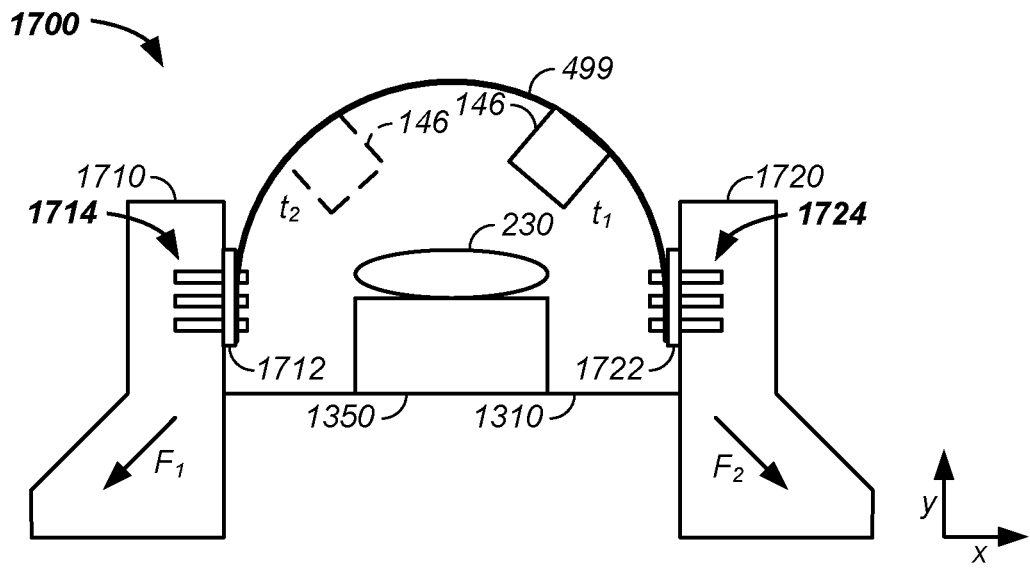
FIG. 17 illustrates a wall mounted gantry system.
Figure 18:
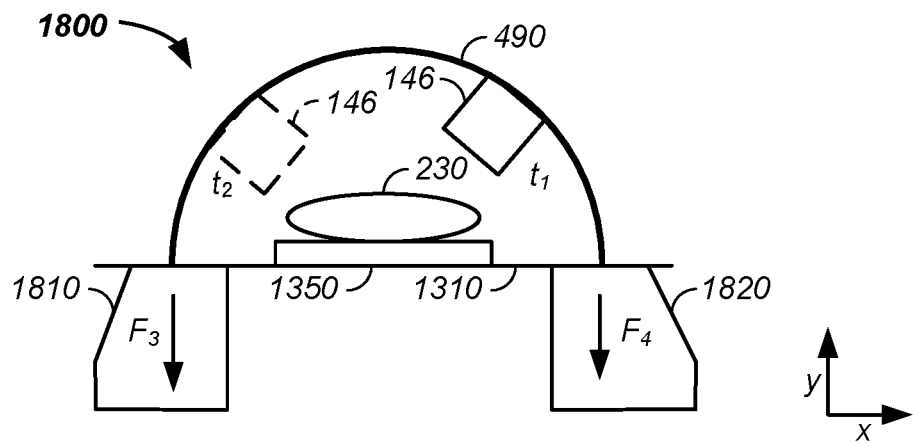
FIG. 18 illustrates a floor mounted gantry system.

Referring now to FIG. 17, a wall mounted gantry system 1700 is illustrated, where a wall mounted gantry 499 is bolted to a first wall 1710, such as a first buttress, with a first set of bolts 1714, optionally using a first mounting element 1712, and mounted to a second wall 1720, such as a second buttress 1720, such a through a second mounting element 1722, with a second set of bolts 1714. The inventor notes that in this design, forces, such as a first force, $F_1$, and a second force, $F_2$, are directed outward into the first wall 1710 and the second wall 1720, respectively, where at least twenty percent of resolved force is along the x-axis as illustrated. Thus, the wall mounted gantry system 499 must be designed to overcome tensile stress on the bolts, greatly increasing mounting costs of the wall mounted gantry system 499. Further, the wall mounted gantry 499 design thus requires that the walls of the building are specially designed to withstand the multi-ton horizontal forces resultant from the wall mounted gantry 499. Further, as the wall mounted gantry 1700 must rotate about an axis of rotation to function, the wall mounted gantry 1700 cannot be connected to front and back walls, but rather can only be mounted to side walls, such as the first wall 1710 and the second wall 1720 as illustrated. Thus, when the wall mounted gantry 499 rotates, the center of mass of the wall mounted gantry 499 necessarily moves into a position that is not between the end mounting points, such as the first mounting element 1712 and the second mounting element 1722. With movement of the center of mass of the wall mounted gantry 499 outside of the supports, the gantry must be configured with additional systems to prevent the wall mounted gantry system 499 from tipping over. In stark contrast, referring now to FIG. 18, in a floor mounted gantry system 1800 the gantry 490 is optionally and preferably designed to rest directly onto a support, such as the floor 1310, with no requirement of a wall mounted system. As illustrated, the mass of the gantry 490 results in only downward forces, such as a third force, $F_3$, into ground or a first pier 1810 and as a fourth force, $F_4$, into ground and/or a second pier 1820. Generally, in the floor mounted gantry system, the center of mass of the gantry 490 is inside a footprint of the piers, such as the first pier 1810 and the second pier 1820 and maintains a footprint inside the piers even as the gantry rotates due to use of additional piers into or out of FIG. 18 and/or due to use of the counter mass in the counterweighted gantry system 1100.

Figure 19:
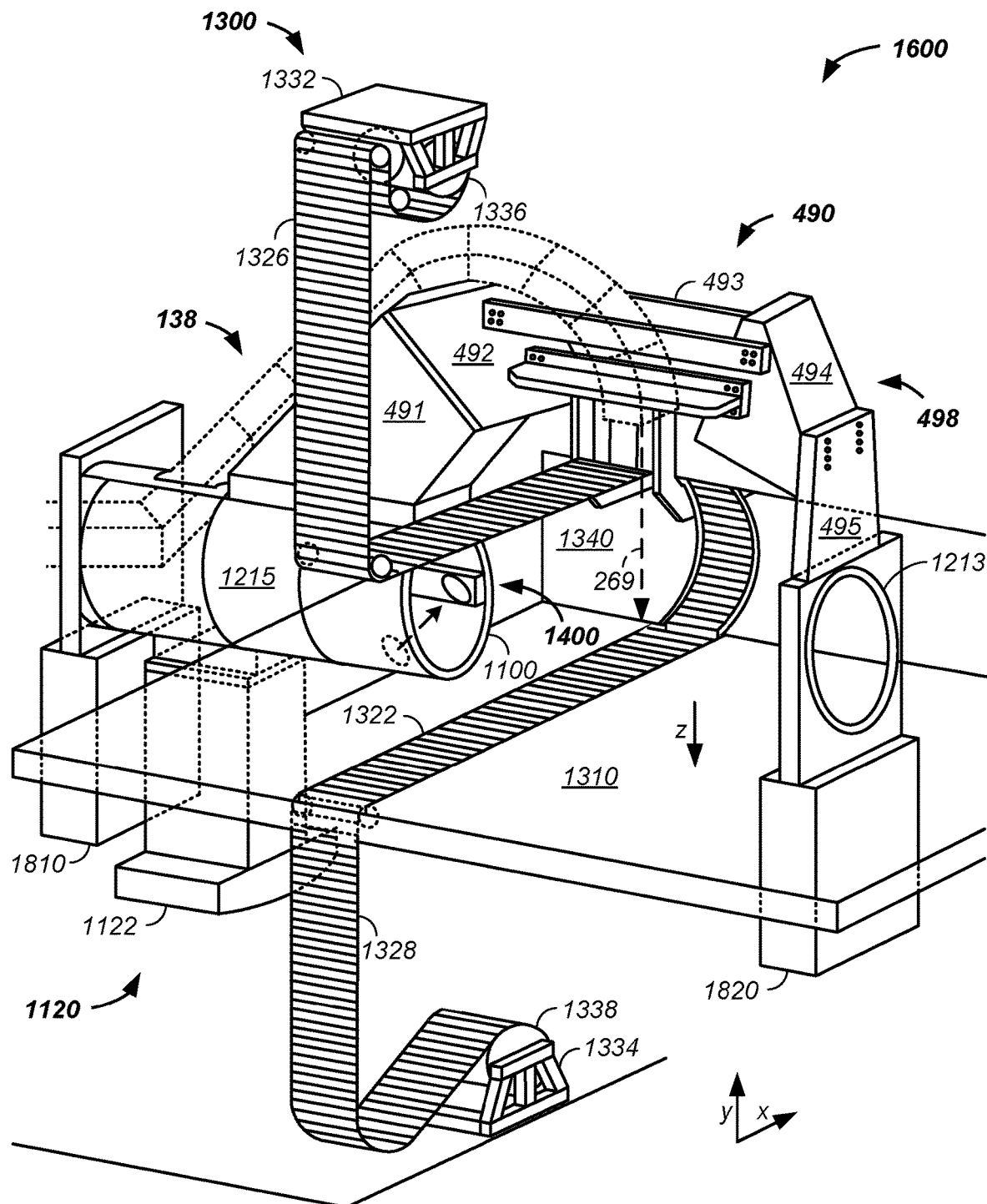
FIG. 19 illustrates a gantry superstructure system.

Referring now to FIG. 19, an example of the gantry superstructure 1600 is illustrated incorporating the gantry 490, the gantry support arm 498, the counterweight system 1120, the rotatable beamline section 138, and the rolling floor system 1300. The rotatable gantry support 1210 is illustrated with the optional hybrid cancer treatment-imaging system 1400. Further, the first pier 1810 and the second pier 1820 of the floor mounted gantry system 1800 are illustrated, which are representative of any number of underfloor gantry support elements designed to support the gantry 490, where the underfloor gantry support elements are out of a rotation path of the gantry support arm 498 and the rotatable beamline section 138.

Referenced Charged Particle Path

Figure 20:
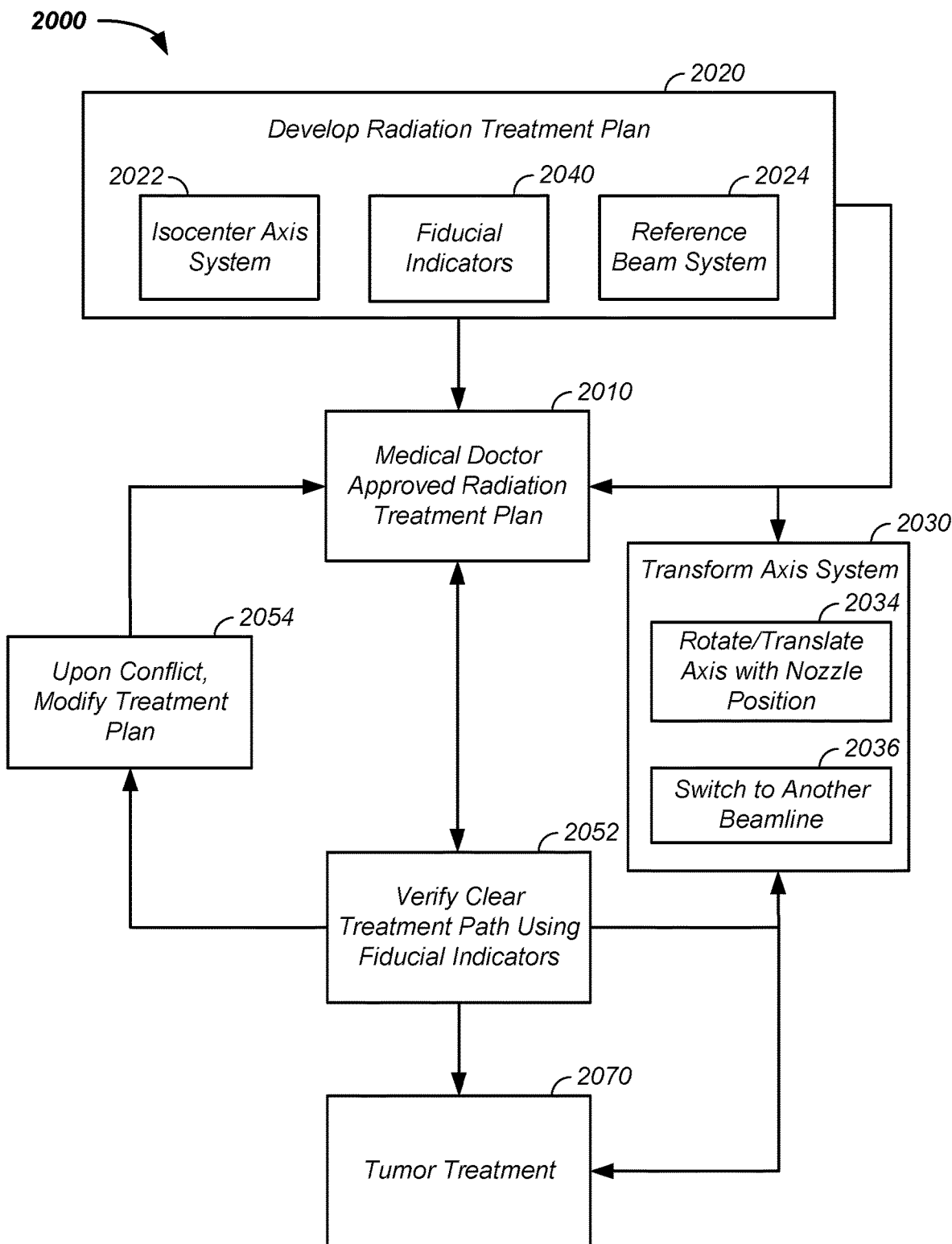
FIG. 20 illustrates a transformable axis system for tumor treatment.

Referring now to FIG. 20, a charged particle reference beam path system 2000 is described, which starkly contrasts to an isocenter reference point of a gantry system, as described supra. The charged particle reference beam path system 2000 defines voxels in the treatment room 922, the patient 230, and/or the tumor 220 relative to a reference path of the positively charged particles and/or a transform thereof. The reference path of the positively charged particles comprises one or more of: a zero vector, an unredirected beamline, an unsteered beamline, a nominal path of the beamline, and/or, such as, in the case of a rotatable gantry and/or movable nozzle, a translatable and/or a rotatable position of the zero vectors. For clarity of presentation and without loss of generality, the terminology of a reference beam path is used herein to refer to an axis system defined by the charged particle beam under a known set of controls, such as a known position of entry into the treatment room 922, a known vector into the treatment room 922, a first known field applied in the first axis controller 143, and/or a second known field applied in the second axis controller 144. Further, as described, supra, a reference zero point or zero point 1002 is a point on the reference beam path. More generally, the reference beam path and the reference zero point optionally refer to a mathematical transform of a calibrated reference beam path and a calibrated reference zero point of the beam path, such as a charged particle beam path defined axis system. The calibrated reference zero point is any point; however, preferably the reference zero point is on the calibrated reference beam path and as used herein, for clarity of presentation and without loss of generality, is a point on the calibrated reference beam path crossing a plane defined by a terminus of the nozzle of the nozzle system 146. Optionally and preferably, the reference beam path is calibrated, in a prior calibration step, against one or more system position markers as a function of one or more applied fields of the first known field and the second known field and optionally energy and/or flux/intensity of the charged particle beam, such as along the treatment beam path 269. The reference beam path is optionally and preferably implemented with a fiducial marker system and is further described infra.

Example I

In a first example, referring still to FIG. 20, the charged particle reference beam path system 2000 is further described using a radiation treatment plan developed using a traditional isocenter axis system 2022. A medical doctor approved radiation treatment plan 2010, such as a radiation treatment plan developed using the traditional isocenter axis system 2022, is converted to a radiation treatment plan using the reference beam path-reference zero point treatment plan. The conversion step, when coupled to a calibrated reference beam path, uses an ideal isocenter point; hence, subsequent treatment using the calibrated reference beam and fiducial indicators 2040 removes the isocenter volume error. For instance, prior to tumor treatment 2070, fiducial indicators 2040 are used to determine position of the patient 230 and/or to determine a clear treatment path to the patient 230. For instance, the reference beam path and/or treatment beam path 269 derived therefrom is projected in software to determine if the treatment beam path 269 is unobstructed by equipment in the treatment room using known geometries of treatment room objects and fiducial indicators 2040 indicating position and/or orientation of one or more and preferably all movable treatment room objects. The software is optionally implemented in a virtual treatment system. Preferably, the software system verifies a clear treatment path, relative to the actual physical obstacles marked with the fiducial indicators 2040, in the less than 5, 4, 3, 2, 1, and/or 0.1 seconds prior to each use of the treatment beam path 269 and/or in the less than 5, 4, 3, 2, 1, and/or 0.1 seconds following movement of the patient positioning system, patient 230, and/or operator.

Example II

In a second example, referring again to FIG. 20, the charged particle reference beam path system 2000 is further described.

Generally, a radiation treatment plan is developed 2020. In a first case, an isocenter axis system 2022 is used to develop the radiation treatment plan 2020. In a second case, a system using the reference beam path of the charged particles 2024 is used to develop the radiation treatment plan. In a third case, the radiation treatment plan developed using the reference beam path 2020 is converted to an isocenter axis system 2022, to conform with traditional formats presented to the medical doctor, prior to medical doctor approval of the radiation treatment plan 2010, where the transformation uses an actual isocenter point and not a mechanically defined isocenter volume and errors associated with the size of the volume, as detailed supra. In any case, the radiation treatment plan is tested, in software and/or in a dry run absent tumor treatment, using the fiducial indicators 2040. The dry run allows a real-life error check to ensure that no mechanical element crosses the treatment beam in the proposed or developed radiation treatment plan 2020. Optionally, a physical dummy placed in a patient treatment position is used in the dry run.

After medical doctor approval of the radiation treatment plan 2010, tumor treatment 2070 commences, optionally and preferably with an intervening step of verifying a clear treatment path 2052 using the fiducial indicators 2040. In the event that the main controller 110 determines, using the reference beam path and the fiducial indicators 1140, that the treatment beam 269 would intersect an object or operator in the treatment room 922, multiple options exist. In a first case, the main controller 110, upon determination of a blocked and/or obscured treatment path of the treatment beam 269, temporarily or permanently stops the radiation treatment protocol. In a second case, optionally after interrupting the radiation treatment protocol, a modified treatment plan is developed 2054 for subsequent medical doctor approval of the modified radiation treatment plan 2010. In a third case, optionally after interrupting the radiation treatment protocol, a physical transformation of a delivery axis system is performed 2030, such as by moving the nozzle system 146, rotating and/or translating the nozzle position 2034, and/or switching to another beamline 2036. Subsequently, tumor treatment 2070 is resumed and/or a modified treatment plan is presented to the medical doctor for approval of the radiation treatment plan.

Automated Cancer Therapy Imaging/Treatment System

Cancer treatment using positively charged particles involves multi-dimensional imaging, multi-axes tumor irradiation treatment planning, multi-axes beam particle beam control, multi-axes patient movement during treatment, and intermittently intervening objects between the patient and/or the treatment nozzle system. Automation of subsets of the overall cancer therapy treatment system using robust code simplifies working with the intermixed variables, which aids oversight by medical professionals. Herein, an automated system is optionally semi-automated, such as overseen by a medical professional.

Example I

Figure 21:
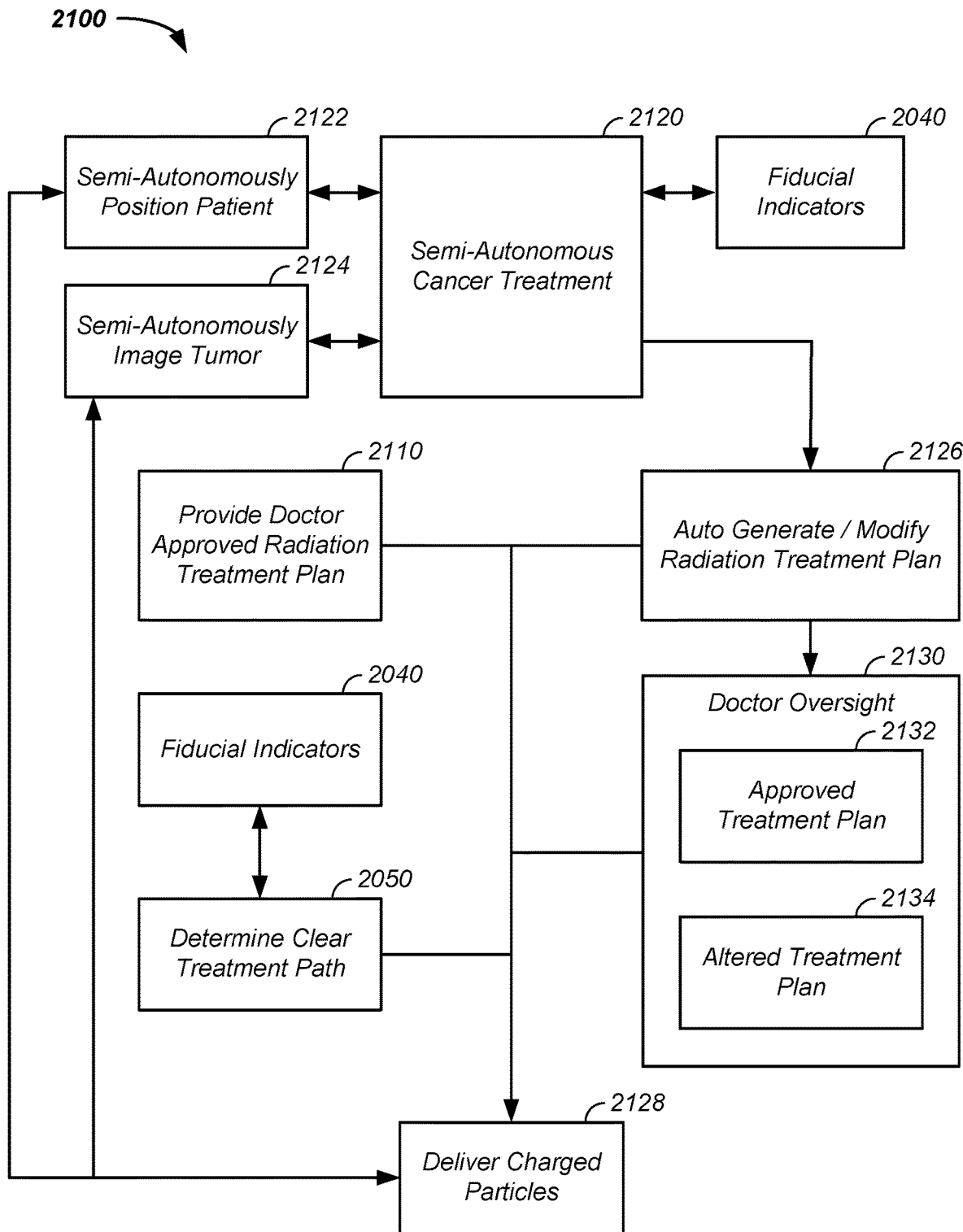
FIG. 21 illustrates a semi-automated cancer therapy imaging/treatment system.

In a first example, referring still to FIG. 20 and referring now to FIG. 21, a first example of a semi-automated cancer therapy treatment system 2100 is described and the charged particle reference beam path system 2000 is further described. The charged particle reference beam path system 2000 is optionally and preferably used to automatically or semi-automatically: (1) identify an upcoming treatment beam path; (2) determine presence of an object in the upcoming treatment beam path; and/or (3) redirect a path of the charged particle beam to yield an alternative upcoming treatment beam path. Further, the main controller 110 optionally and preferably contains a prescribed tumor irradiation plan, such as provided by a prescribing doctor. In this example, the main controller 110 is used to determine an alternative treatment plan to achieve the same objective as the prescribed treatment plan. For instance, the main controller 110, upon determination of the presence of an intervening object in an upcoming treatment beam path or imminent treatment path directs and/or controls: movement of the intervening object; movement of the patient positioning system; and/or position of the nozzle system 146 to achieve identical or substantially identical treatment of the tumor 220 in terms of radiation dosage per voxel and/or tumor collapse direction, where substantially identical is a dosage and/or direction within 90, 95, 97, 98, 99, or 99.5 percent of the prescription. Herein, an imminent treatment path is the next treatment path of the charged particle beam to the tumor in a current version of a radiation treatment plan and/or a treatment beam path/vector that is scheduled for use within the next 1, 5, 10, 30, or 60 seconds. In a first case, the revised tumor treatment protocol is sent to a doctor, such as a doctor in a neighboring control room and/or a doctor in a remote facility or outside building, for approval. In a second case, the doctor, present or remote, oversees an automated or semi-automated revision of the tumor treatment protocol, such as generated using the main controller. Optionally, the doctor halts treatment, suspends treatment pending an analysis of the revised tumor treatment protocol, slows the treatment procedure, or allows the main controller to continue along the computer suggested revised tumor treatment plan. Optionally and preferably, imaging data and/or imaging information, such as described supra, is input to the main controller 110 and/or is provided to the overseeing doctor or the doctor authorizing a revised tumor treatment irradiation plan.

Example II

Referring now to FIG. 21, a second example of the semi-automated cancer therapy treatment system 2100 is described. Initially, a medical doctor, such as an oncologist, provides an approved radiation treatment plan 2110, which is implemented in a treatment step of delivering charged particles 2128 to the tumor 220 of the patient 230. Concurrent with implementation of the treatment step, additional data is gathered, such as via an updated/new image from an imaging system and/or via the fiducial indicators 2040. Subsequently, the main controller 110 optionally, in an automated process or semi-automated process, adjusts the provided doctor approved radiation treatment plan 2110 to form a current radiation treatment plan. In a first case, cancer treatments halts until the doctor approves the proposed/adjusted treatment plan and continues using the now, doctor approved, current radiation treatment plan. In a second case, the computer generated radiation treatment plan continues in an automated fashion as the current treatment plan. In a third case, the computer generated treatment plan is sent for approval, but cancer treatment proceeds at a reduced rate to allow the doctor time to monitor the changed plan. The reduced rate is optionally less than 100, 90, 80, 70, 60, or 50 percent of the original treatment rate and/or is greater than 0, 10, 20, 30, 40, or 50 percent of the original treatment rate. At any time, the overseeing doctor, medical professional, or staff may increase or decrease the rate of treatment.

Example III

Referring still to FIG. 21, a third example of the semi-automated cancer therapy treatment system 2100 is described. In this example, a process of semi-autonomous cancer treatment 2120 is implemented. In stark contrast with the previous example where a doctor provides the original cancer treatment plan 2110, in this example the cancer therapy system 110 auto-generates a radiation treatment plan 2126. Subsequently, the auto-generated treatment plan, now the current radiation treatment plan, is implemented, such as via the treatment step of delivering charged particles 2128 to the tumor 220 of the patient 230. Optionally and preferably, the auto-generated radiation treatment plan 2126 is reviewed in an intervening and/or concurrent doctor oversight step 2130, where the auto-generated radiation treatment plan 2126 is approved as the current treatment plan 2132 or approved as an alternative treatment plan 2134; once approved referred to as the current treatment plan.

Generally, the original doctor approved treatment plan 2110, the auto generated radiation treatment plan 2126, or the altered treatment plan 2134, when being implemented is referred to as the current radiation treatment plan.

Example IV

Referring still to FIG. 21, a fourth example of the semi-automated cancer therapy treatment system 2100 is described. In this example, the current radiation treatment plan, prior to implementation of a particular set of voxels of the tumor 220 of the patient 230, is analyzed in terms of clear path analysis, as described supra. More particularly, fiducial indicators 2040 are used in determination of a clear treatment path prior to treatment along an imminent beam treatment path to one or more voxels of the tumor 220 of the patient. Upon implementation, the imminent treatment vector is the treatment vector in the deliver charged particles step 2128.

Example V

Referring still to FIG. 21, a fifth example of the semi-automated cancer therapy treatment system 2100 is described. In this example, a cancer treatment plan is generated semi-autonomously or autonomously using the main controller 110 and the process of semi-autonomous cancer treatment system. More particularly, the process of semi-autonomous cancer treatment 2120 uses input from: (1) a semi-autonomously patient positioning step 2122; (2) a semi-autonomous tumor imaging step 2124, and/or for the fiducial indicators 2040; and/or (3) a software coded set of radiation treatment directives with optional weighting parameters. For example, the treatment directives comprise a set of criteria to: (1) treat the tumor 220; (2) while reducing energy delivery of the charged particle beam outside of the tumor 220; minimizing or greatly reducing passage of the charged particle beam into a high value element, such as an eye, nerve center, or organ, the process of semi-autonomous cancer treatment 2120 optionally auto-generates the original radiation treatment plan 2126. The auto-generated original radiation treatment plan 2126 is optionally auto-implemented, such as via the deliver charged particles step 2126, and/or is optionally reviewed by a doctor, such as in the doctor oversight 2130 process, described supra.

Optionally and preferably, the semi-autonomous imaging step 2124 generates and/or uses data from: (1) one or more proton scans from an imaging system using protons to image the tumor 220; (2) one or more X-ray images using one or more X-ray imaging systems; (3) a positron emission system; (4) a computed tomography system; and/or (5) any imaging technique or system described herein.

The inventor notes that traditionally days pass between imaging the tumor and treating the tumor while a team of oncologists develop a radiation plan. In stark contrast, using the autonomous imaging and treatment steps described herein, such as implemented by the main controller 110, the patient optionally remains in the treatment room and/or in a treatment position in a patient positioning system from the time of imaging, through the time of developing a radiation plan, and through at least a first tumor treatment session.

Example VI

Referring still to FIG. 21, a sixth example of the semi-automated cancer therapy treatment system 2100 is described. In this example, the deliver charged particle step 2128, using a current radiation treatment plan, is adjusted autonomously or semi-autonomously using concurrent and/or interspersed images from the semi-autonomously imaging system 2124 as interpreted, such as via the process of semi-automated cancer treatment 2120 and input from the fiducial indicators 2040 and/or the semi-automated patient position system 2122.

Figure 22:
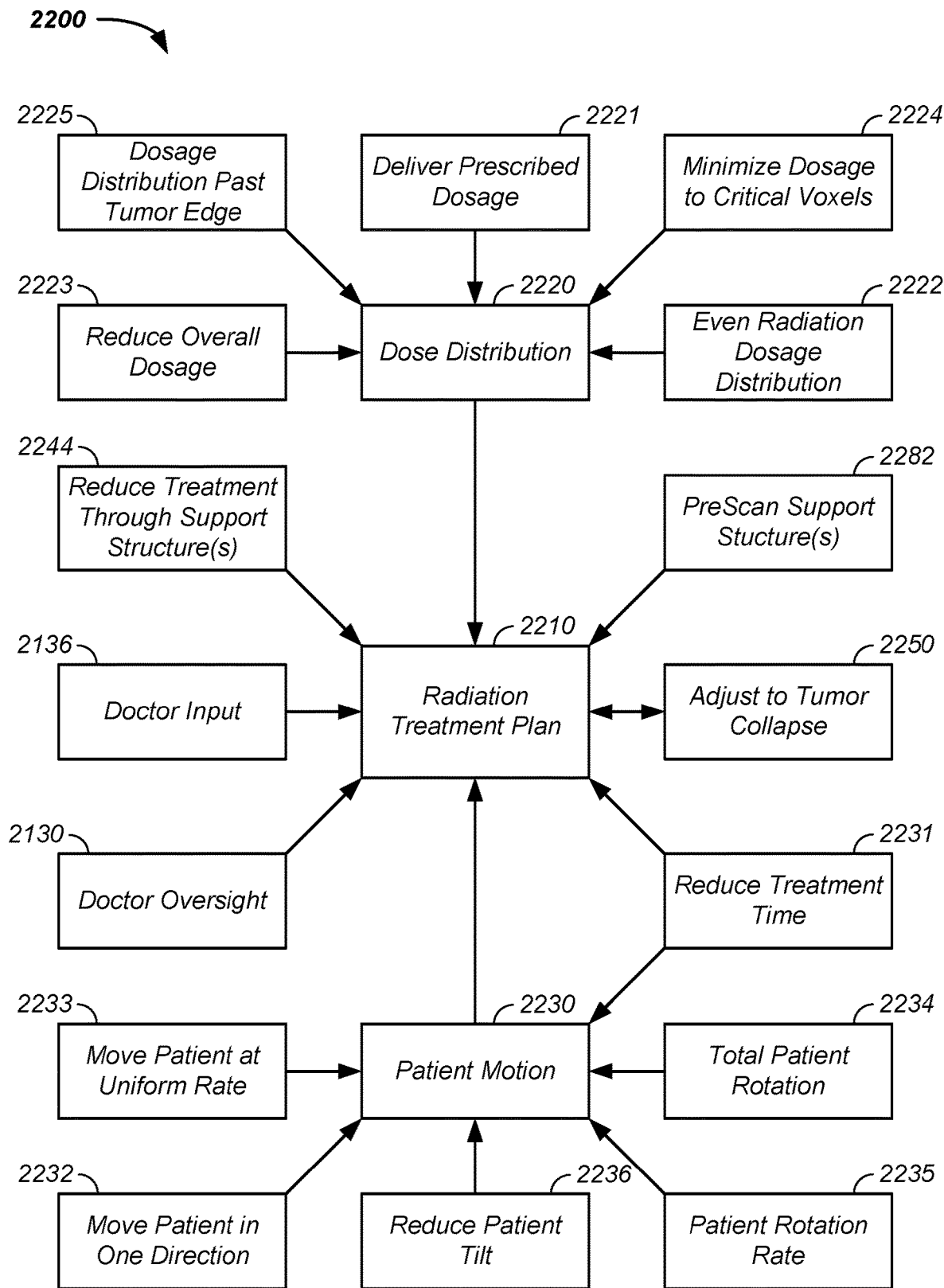
FIG. 22 illustrates a system of automated generation of a radiation treatment plan.

Referring now to FIG. 22, a system for developing a radiation treatment plan 2210 using positively charged particles is described. More particularly, a semi-automated radiation treatment plan development system 2200 is described, where the semi-automated system is optionally fully automated or contains fully automated sub-processes.

The computer implemented algorithm, such as implemented using the main controller 110, in the automated radiation treatment plan development system 2200 generates a score, sub-score, and/or output to rank a set of auto-generated potential radiation treatment plans, where the score is used in determination of a best radiation treatment plan, a proposed radiation treatment plan, and/or an auto-implemented radiation treatment plan.

Still referring to FIG. 22, the semi-automated or automated radiation treatment plan development system 2200 optionally and preferably provides a set of inputs, guidelines, and/or weights to a radiation treatment development code that processes the inputs to generate an optimal radiation treatment plan and/or a preferred radiation treatment plan based upon the inputs, guidelines, and/or weights. An input is a goal specification, but not an absolute fixed requirement. Input goals are optionally and preferably weighted and/or are associated with a hard limit. Generally, the radiation treatment development code uses an algorithm, an optimization protocol, an intelligent system, computer learning, supervised, and/or unsupervised algorithmic approach to generating a proposed and/or immediately implemented radiation treatment plan, which are compared via the score described above. Inputs to the semi-automated radiation treatment plan development system 2200 include images of the tumor 220 of the patient 230, treatment goals, treatment restrictions, associated weights to each input, and/or associated limits of each input. To facilitate description and understanding of the invention, without loss of generality, optional inputs are illustrated in FIG. 22 and further described herein by way of a set of examples.

Example I

Still referring to FIG. 22, a first input to the semi-automated radiation treatment plan development system 2200, used to generate the radiation treatment plan 2210, is a requirement of dose distribution 2220. Herein, dose distribution comprises one or more parameters, such as a prescribed dosage 2221 to be delivered; an evenness or uniformity of radiation dosage distribution 2222; a goal of reduced overall dosage 2223 delivered to the patient 230; a specification related to minimization or reduction of dosage delivered to critical voxels 2224 of the patient 230, such as to a portion of an eye, brain, nervous system, and/or heart of the patient 230; and/or an extent of, outside a perimeter of the tumor, dosage distribution 2225. The automated radiation treatment plan development system 2200 calculates and/or iterates a best radiation treatment plan using the inputs, such as via a computer implemented algorithm.

Each parameter provided to the automated radiation treatment plan development system 2200, optionally and preferably contains a weight or importance. For clarity of presentation and without loss of generality, two cases illustrate.

In a first case, a requirement/goal of reduction of dosage or even complete elimination of radiation dosage to the optic nerve of the eye, provided in the minimized dosage to critical voxels 2224 input is given a higher weight than a requirement/goal to minimize dosage to an outer area of the eye, such as the rectus muscle, or an inner volume of the eye, such as the vitreous humor of the eye. This first case is exemplary of one input providing more than one sub-input where each sub-input optionally includes different weighting functions.

In a second case, a first weight and/or first sub-weight of a first input is compared with a second weight and/or a second sub-weight of a second input. For instance, a distribution function, probability, or precision of the even radiation dosage distribution 2222 input optionally comprises a lower associated weight than a weight provided for the reduce overall dosage 2223 input to prevent the computer algorithm from increasing radiation dosage in an attempt to yield an entirely uniform dose distribution.

Each parameter and/or sub-parameter provided to the automated radiation treatment plan development system 2200, optionally and preferably contains a limit, such as a hard limit, an upper limit, a lower limit, a probability limit, and/or a distribution limit. The limit requirement is optionally used, by the computer algorithm generating the radiation treatment plan 2210, with or without the weighting parameters, described supra.

Example II

Still referring to FIG. 22, a second input to the semi-automated radiation treatment plan development system 2200, is a patient motion 2230 input. The patient motion 2230 input comprises: a move the patient in one direction 2232 input, a move the patient at a uniform speed 2233 input, a total patient rotation 2234 input, a patient rotation rate 2235 input, and/or a patient tilt 2236 input. For clarity of presentation and without loss of generality, the patient motion inputs are further described, supra, in several cases.

Still referring to FIG. 22, in a first case the automated radiation treatment plan development system 2200, provides a guidance input, such as the move the patient in one direction 2232 input, but a further associated directive is if other goals require it or if a better overall score of the radiation treatment plan 2210 is achieved, the guidance input is optionally automatically relaxed. Similarly, the move the patient at a uniform rate 2233 input is also provided with a guidance input, such as a low associated weight that is further relaxable to yield a high score, of the radiation treatment plan 2210, but is only relaxed or implemented an associated fixed or hard limit number of times.

Still referring to FIG. 22, in a second case the computer implemented algorithm, in the automated radiation treatment plan development system 2200, optionally generates a sub-score. For instance, a patient comfort score optionally comprises a score combining a metric related to two or more of: the move the patient in one direction 2232 input, the move the patient at a uniform rate 2233 input, the total patient rotation 2234 input, the patient rotation rate 2235 input, and/or the reduce patient tilt 2236 input. The sub-score, which optionally has a preset limit, allows flexibility, in the computer implemented algorithm, to yield on patient movement parameters as a whole, again to result in patient comfort.

Still referring to FIG. 22, in a third case the automated radiation treatment plan development system 2200 optionally contains an input used for more than one sub-function. For example, a reduce treatment time 2231 input is optionally used as a patient comfort parameter and also links into the dose distribution 2220 input.

Example III

Still referring to FIG. 22, a third input to the automated radiation treatment plan development system 2200 comprises output of an imaging system, such as any of the imaging systems described herein.

Example IV

Still referring to FIG. 22, a fourth optional input to the automated radiation treatment plan development system

2200 is structural and/or physical elements present in the treatment room 922. Again, for clarity of presentation and without loss of generality, two cases illustrate treatment room object information as an input to the automated development of the radiation treatment plan 2210.

Still referring to FIG. 22, in a first case the automated radiation treatment plan development system 2200 is optionally provided with a pre-scan of potentially intervening support structures 2282 input, such as a patient support device, a patient couch, and/or a patient support element, where the pre-scan is an image/density/redirection impact of the support structure on the positively charged particle treatment beam. Preferably, the pre-scan is an actual image or tomogram of the support structure using the actual facility synchrotron, a remotely generated actual image, and/or a calculated impact of the intervening structure on the positively charge particle beam. Determination of impact of the support structure on the charged particle beam is further described, infra.

Still referring to FIG. 22, in a second case the automated radiation treatment plan development system 2200 is optionally provided with a reduce treatment through a support structure 2244 input. As described supra, an associated weight, guidance, and/or limit is optionally provided with the reduce treatment through the support structure 2244 input and, also as described supra, the support structure input is optionally compromised relative to a more critical parameter, such as the deliver prescribed dosage 2221 input or the minimize dosage to critical voxels 2224 of the patient 230 input.

Example V

Still referring to FIG. 22, a fifth optional input to the automated radiation treatment plan development system 2200 is a doctor input 2136, such as provided only prior to the auto generation of the radiation treatment plan. Separately, doctor oversight 2130 is optionally provided to the automated radiation treatment plan development system 2200 as plans are being developed, such as an intervention to restrict an action, an intervention to force an action, and/or an intervention to change one of the inputs to the automated radiation treatment plan development system 2200 for a radiation plan for a particular individual.

Example VI

Still referring to FIG. 22, a sixth input to the automated radiation treatment plan development system 2200 comprises information related to collapse and/or shifting of the tumor 220 of the patient 230 during treatment. For instance, the radiation treatment plan 2210 is automatically updated, using the automated radiation treatment plan development system 2200, during treatment using an input of images of the tumor 220 of the patient 230 collected concurrently with treatment using the positively charged particles. For instance, as the tumor 220 reduces in size with treatment, the tumor 220 collapses inward and/or shifts. The auto-updated radiation treatment plan is optionally auto-implemented, such as without the patient moving from a treatment position. Optionally, the automated radiation treatment plan development system 2200 tracks dosage of untreated voxels of the tumor 220 and/or tracks partially irradiated, relative to the prescribed dosage 2221, voxels and dynamically and/or automatically adjusts the radiation treatment plan 2210 to provide the full prescribed dosage to each voxel despite movement of the tumor 220. Similarly, the automated radiation treatment plan development system 2200 tracks dosage of treated voxels of the tumor 220 and adjusts the automatically updated tumor treatment plan to reduce and/or minimize further radiation delivery to the fully treated and shifted tumor voxels while continuing treatment of the partially treated and/or untreated shifted voxels of the tumor 220.

Automated Adaptive Treatment

Figure 23:
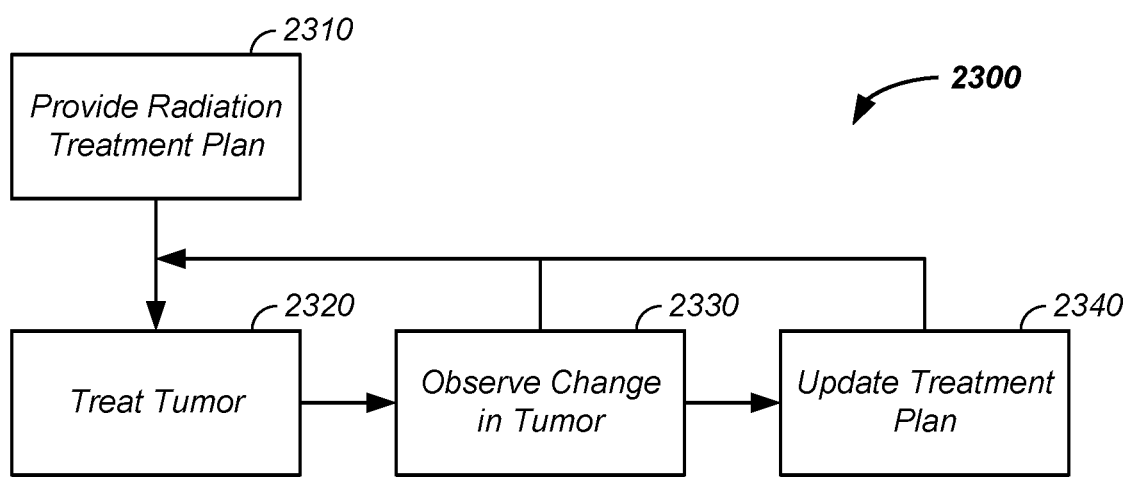
FIG. 23 illustrates a system of automatically updating a cancer radiation treatment plan during treatment.

Referring now to FIG. 23, a system for automatically updating the radiation treatment plan 2300 and preferably automatically updating and implementing the radiation treatment plan is illustrated. In a first task 2310, an initial radiation treatment plan is provided, such as the auto-generated radiation treatment plan 2126, described supra. The first task is a startup task of an iterative loop of tasks and/or recurring set of tasks, described herein as comprising tasks two to four.

In a second task 2320, the tumor 220 is treated using the positively charged particles delivered from the synchrotron 130. In a third task 2330, changes in the tumor shape and/or changes in the tumor position relative to surrounding constituents of the patient 230 are observed, such as via any of the imaging systems described herein. The imaging optionally occurs simultaneously, concurrently, periodically, and/or intermittently with the second task while the patient remains positioned by the patient positioning system. The main controller 110 uses images from the imaging system(s) and the provided and/or current radiation treatment plan to determine if the treatment plan is to be followed or modified. Upon detected relative movement of the tumor 220 relative to the other elements of the patient 230 and/or change in a shape of the tumor 230, a fourth task 2340 of updating the treatment plan is optionally and preferably automatically implemented and/or use of the radiation treatment plan development system 2200, described supra, is implemented. The process of tasks two to four is optionally and preferably repeated n times where n is a positive integer of greater than 1, 2, 5, 10, 20, 50, or 100 and/or until a treatment session of the tumor 220 ends and the patient 230 departs the treatment room 922.

Automated Treatment

Figure 24:
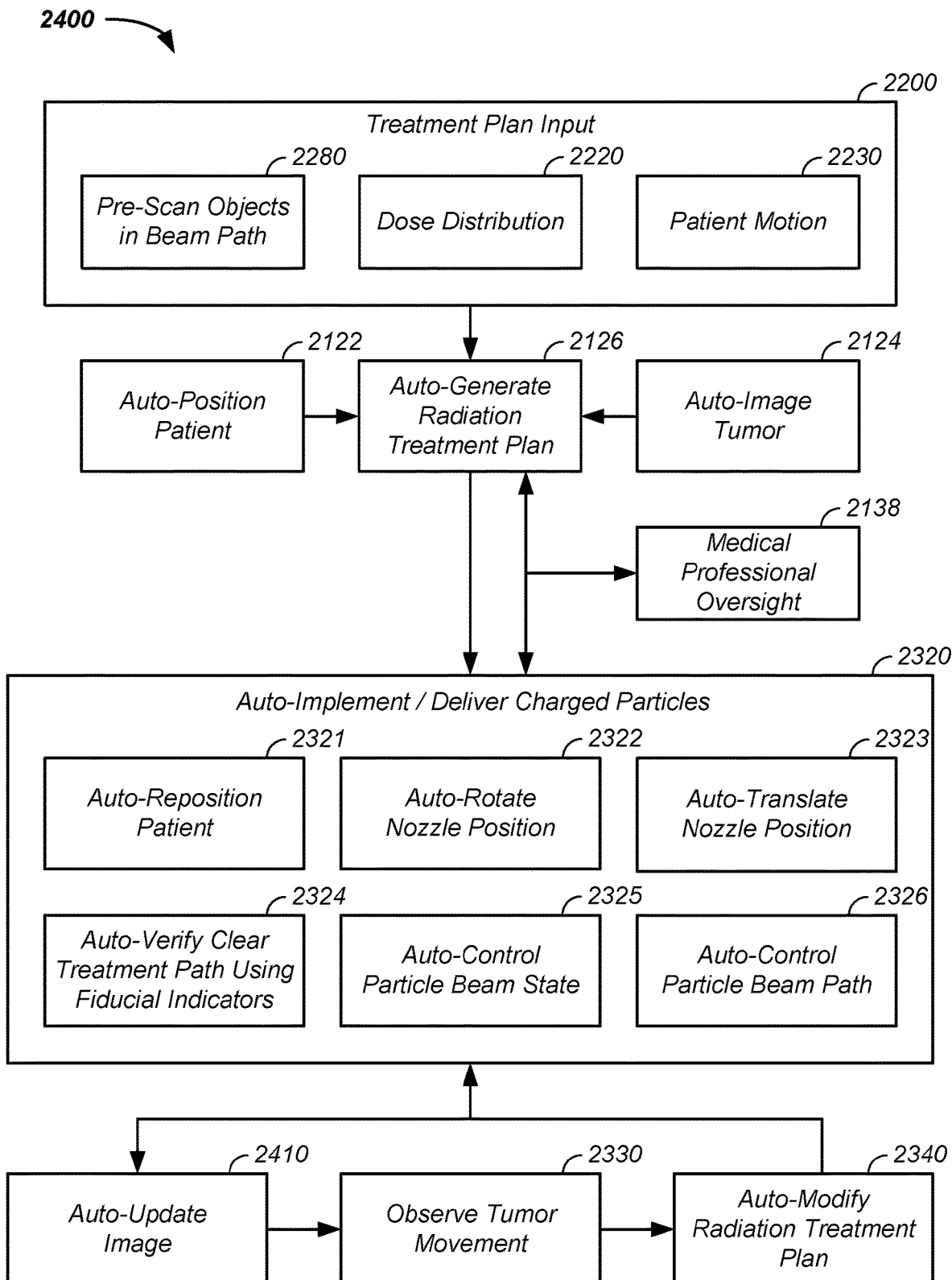
FIG. 24 illustrates an automated radiation treatment plan development and implementation system.

Referring now to FIG. 24, an automated cancer therapy treatment system 2400 is illustrated. In the automated cancer therapy treatment system 2400, a majority of tasks are implemented according to a computer based algorithm and/or an intelligent system. Optionally and preferably, a medical professional oversees the automated cancer therapy treatment system 2400 and stops or alters the treatment upon detection of an error but fundamentally observes the process of computer algorithm guided implementation of the system using electromechanical elements, such as any of the hardware and/or software described herein. Optionally and preferably, each sub-system and/or sub-task is automated. Optionally, one or more of the sub-systems and/or sub-tasks are performed by a medical professional. For instance, the patient 230 is optionally initially positioned in the patient positioning system by the medical professional and/or the nozzle system 146 inserts are loaded by the medical professional. Optional and preferably automated, such as computer algorithm implemented, sub-tasks include one or more and preferably all of:

receiving the treatment plan input 2200, such as a prescription, guidelines, patient motion guidelines 2230, dose distribution guidelines 2220, intervening object 2210 information, and/or images of the tumor 220;

using the treatment plan input 2200 to auto-generate a radiation treatment plan 2126;

auto-positioning 2122 the patient 230;
auto-imaging 2124 the tumor 220;
implementing medical profession oversight 2138 instructions;
auto-implementing the radiation treatment plan 2320/ delivering the positively charged particles to the tumor 220;
auto-reposition the patient 2321 for subsequent radiation delivery;
auto-rotate a nozzle position 2322 of the nozzle system 146 relative to the patient 230;
auto-translate a nozzle position 2323 of the nozzle system 146 relative to the patient 230;
auto-verify a clear treatment path using an imaging system, such as to observe presence of a metal object or unforeseen dense object via an X-ray image;
auto-verify a clear treatment path using fiducial indicators 2324;
auto control a state of the positively charge particle beam 2325, such as energy, intensity, position (x,y,z), duration, and/or direction;
auto-control a particle beam path 2326, such as to a selected beamline and/or to a selected nozzle;
auto implement positioning a tray insert and/or tray assembly;
auto-update a tumor image 2410;
auto-observe tumor movement 2330; and/or
generate an auto-modified radiation treatment plan 2340/ new treatment plan.

Treatment Beam Progression

Referring now to FIGS. 25-32, treatment beam progression is described. More particularly, reduction in systematic errors by control of order and/or position of treatment of tumor voxels is described.

Referring now to FIG. 25 and FIG. 26, row-by-row voxel treatment of a tumor, the tumor not illustrated for clarity of presentation, is compared with non-row treatment of a tumor, referred to herein as a controlled beam progression treatment and/or a controlled random beam position treatment system. Referring now to FIG. 25, a first voxel of the tumor is treated, then second, third, fourth, fifth, and sixth voxels are sequentially treated with the treatment beam 269. Subsequently, second, third, fourth, . . . , $n^{th}$ rows are treated until all voxels in an x/y-plane of the tumor are treated, the first nine treatment voxels are illustrated. In stark contrast, referring now to FIG. 26, the treatment beam 269 over time will treat all of the x/y-plane pixels, but in a random order as a function of x-axis position and y-axis position.

Referring now to FIGS. 25-32, for clarity of presentation and without loss of generality, the beam is illustrated as a function of time moving along a first axis, such as the x-axis, relative to a second axis, such as the y-axis. However, the beam is optionally scanned along and/or moved randomly along the x-axis, the y-axis, the z-axis, any pair of axes, and/or along all three axes as a function of time. Further, the x, y, and z-axes are optionally treated at m, n, or o positions, where m, n, and o are positive integers.

Systematic Beam Position Errors

A charged particle cancer therapy system uses a complex instrument in a complex setting. Many changes to the beam output as a function of time versus a planned treatment result, such as during scanning the beam position, delivering an intended beam energy, and/or delivering an intended beam energy. Many known factors impact precision and accuracy of the beam state, where various calibration and/or control systems minimize precision and accuracy error. However, physics dictates that absolute control of the treatment beam state in terms of precision and accuracy is not possible. Further, unknown parameters may lead to errors, such as systematic errors, in the beam state accuracy and precision. Two known and controlled errors are illustrated in the following examples.

Example I

Referring now to FIG. 27, a first beam state change as a function of time 2700 is illustrated. In this example, at a first time a first beam diameter 2710 comprises a first radius, such as during device warm up. At a second time, a second beam diameter 2720 is illustrated, where the second beam diameter is larger than the first beam diameter, which represents a beam intensity drift as a function of time. The beam intensity/diameter as a function of time may change by less than 20, 10, 5, 2, or 1 percent. However, the beam diameter directly affects an x/y-plane beam/intensity diameter of a currently treated tumor voxel.

Example II

Referring now to FIG. 28, a second beam state change as a function of time 2800 is illustrated. In this example, a reference circle 2810 is illustrated. At a first time, a first beam position 2820 is centered within the reference circle 2810. At a second time, a second beam position 2830 is offset in the x/y-plane relative to the reference circle 2810, which represents a beam position drift as a function of time. Again, the beam position as a function of time may change by less than 20, 10, 5, 2, or 1 percent. However, the beam position directly affects an x/y-plane beam position of a currently treated tumor voxel.

Some contributors to the two above described beam state changes may be identified and/or controlled, such as warm-up time, hysteresis, and magnet operating temperature. However, the contributors are convoluted, additional unknown causes may be present, and uncontrollable causes may result, such as a patient twitch. Referring now to FIG. 29, potential error of net changes in intensity 2900 of the treatment beam 269 as a function of time are illustrated, such as across five treatment voxels 2910. The inventor notes that beam progression control methods and apparatus that reduce systematic error in beam state result in reduced systematic error in delivered radiation dosage as a function of x,y,z-beam position in tumor treatment.

Beam Progression Control

Referring now to FIGS. 30-32, for clarity of presentation and without loss of generality, examples of beam progression and control patterns are provided. Generally, the main controller 110 or subsystem thereof controls progression of the beam state in terms of x-position, y-position, dispersion, focus, timing, energy, and/or intensity to treat the tumor voxels in a manner reducing known and/or unknown systematic errors in radiation dosage delivery as a function of x,y,z-position in the tumor 220 of the patient 230. Examples of beam state control mechanisms include, but are not limited to: (1) control of the current/magnetic field in the first axis controller 143 and/or the second axis controller 144; (2) control of energy of the extracted charged particle beam, such as through use of the extraction system 134; (3) control of intensity, such as using the intensity control system 225; (4) use of the continuously variable proton beam energy controller 460; (5) an energy beam adjustment system, described infra; (6) a non-uniformly thick material rotated and/or translated in the beam path to alter energy of the beam; and/or (7) movement of the patient 230, such as through use of the patient positioning system 1350.

Example I

Referring now to FIG. 30, an example of beam progression control using a dithering system 3000 is described. In dithering, the treatment beam 269 is intentionally dithered, moved, and/or focused in a position slightly offset from a target spot, line, or volume. As illustrated, five planned treatment spots 3010 are illustrated along a line. The controlled and intentionally dithered spots 2720 illustrate five treatment spots that are, respectively, above, to the right side, diagonally downward, left, and above the five planned treatment spots 3010, which reduces systematic error, such as an offset beam, especially when the same tumor volumes are treated on subsequent days, such as a second, third, and fourth day with a different dither as a function of time. Dithering of the treatment beam 269 is optionally random or intentionally different for a given tumor voxel during subsequent treatments.

Example II

Referring now to FIG. 31, an example of beam progression control using a multi-axis control system 3100 is illustrated. In this example, the progression of the treatment beam 269 from tumor voxel to tumor voxel: (1) initiates at least one treatment voxel diameter from an edge of the tumor 220; (2) scans in at least three directions, such as relative motions of down, then left, then up; (3) scans in at least four directions, such as relative motions of up, then right, then down, then left; (4) scans in opposite directions as a function of time, such as left and then right and/or in and then out; (5) scans along one axis at one time and along two axes at a second time; (6) scans along three axes at a time, such as diagonally into the tumor 220; and (7) combines scanning steps described herein.

Example III

Referring now to FIG. 32, a multi-day beam progression control 3200 is illustrated. In this example, the treatment beam 269 follows different patterns during at least two, three, or four separate treatment times or sessions, such as on different days and/or during different patient seatings on the patient positioning system 1350. As illustrated, on different treatment days the same tumor voxel is treated: (1) with movement of the treatment beam, between tumor voxels, from different directions, such as through movement along the x, y, or z-axes; (2) form treatment loops, such as illustrated in day 2; (3) treats rows or columns on one day while 'stitching' rows and or columns by repeatedly overlapping beam treatment trails, such as illustrated in day 3; (4) uses dithering on one day and not another for a given tumor voxel; and/or (5) use any combinations of beam progression approaches one different days.

Generally, the intent of beam progression control is to minimize, reduce, and/or eliminate systematic errors involved in tumor treatment to provide a uniform and therapeutic radiation dose throughout the tumor. As described supra, the beam progression control moves the treatment beam 269 through non-linear paths during a portion of the tumor treatment. More specifically, the treatment beam 269 is intentionally moved: (1) at least $1/8^{th}$, $1/6^{th}$, $1/4^{th}$, $1/2$, or 1 diameter or cross-sectional length of a treatment beam spot size of the treatment beam, such as, for a two millimeter treatment beam spot size, a movement of $1/4$, $2/3$, $1/2$, 1, or 2 millimeters; (2) at least $1/4^{th}$ of a treatment beam diameter off of a treatment vector at least, on average, once every 5, 10, 15, 20, 25, or 30 movements of the treatment beam along a given vector in the tumor 220; (3) off of a treatment vector for at least 1, 2, 3, 4, 5, or more treated tumor voxels as the treatment beam 269 progresses from a first edge of the tumor 220 to an opposite edge of the tumor 220; (4) for a set of treatment vectors for treating the tumor, intentionally deviating, on average, off of the treatment vector by at least $1/8^{th}$ of a treatment beam diameter at least once for every 3, 5, 10, or 20 movements of the treatment beam; and/or (5) any permutation and/or combination of treatment beam progressions described herein.

Multiple Beam Energies

Referring now to FIG. 33A through FIG. 38, a system is described that allows continuity in beam treatment between energy levels.

Figure 33A:
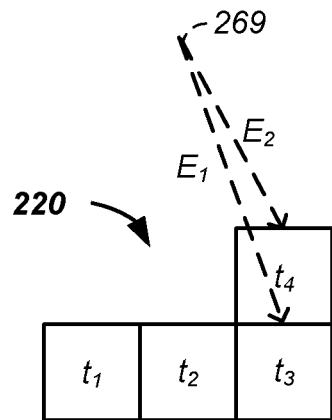
FIG. 33A and FIG. 33B illustrate decreasing and increasing beam energy as a function of time, respectively.
Figure 33B:
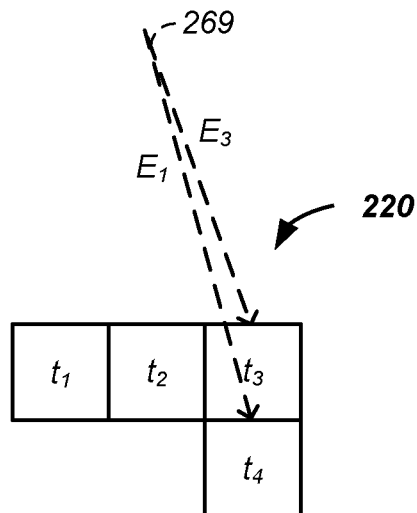

Referring now to FIG. 33A and FIG. 33B, treating the tumor 220 of the patient 230 using at least two beam energies is illustrated. Referring now to FIG. 33A, in a first illustrative example the treatment beam 269 is used at a first energy, $E_1$, to treat a first, second, and third voxel of the tumor at a first, second, and third time, $t_{1-3}$, respectively. At a fourth time, $t_4$, the treatment beam 269 is used at a lower second energy, $E_2$, to treat the tumor 220, such as at a shallower depth in the patient 230. Similarly, referring now to FIG. 33B, in a second illustrative example the treatment beam 269 is used at a first energy, $E_1$, to treat a first, second, and third voxel of the tumor at a first, second, and third time, $t_{1-3}$, respectively. At a fourth time, $t_4$, the treatment beam 269 is used at a higher third energy, $E_3$, to treat the tumor 220, such as at a greater depth of penetration into the patient 230.

Figure 34:
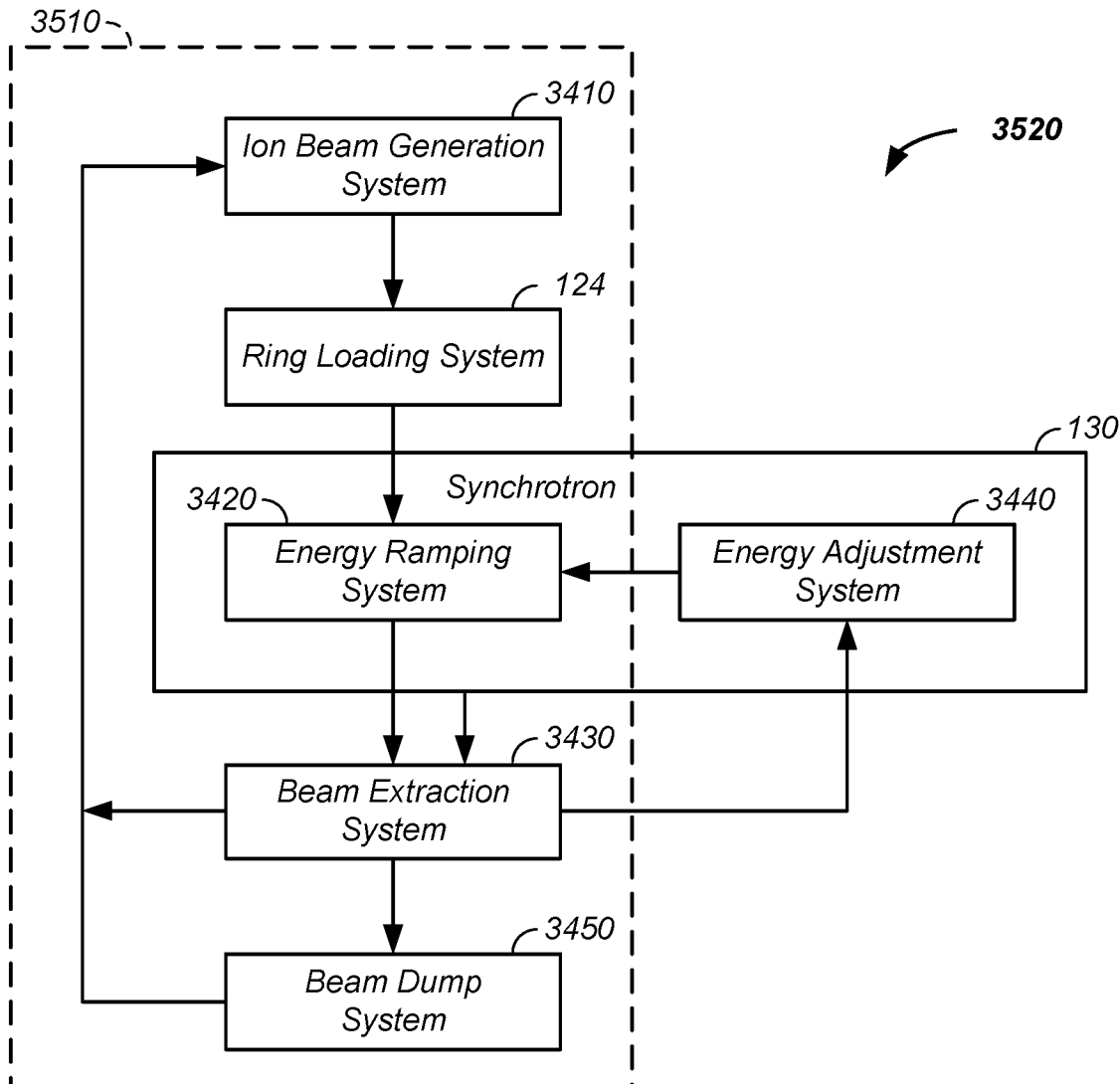
FIG. 34 illustrates a beam energy adjustment system.

Referring now to FIG. 34, two systems are described that treat the tumor 220 of the patient 230 with at least two energy levels of the treatment beam 269: (1) a beam interrupt system 3510 dumping the beam from an accelerator ring, such as the synchrotron 130, between use of the treatment beam 269 at a first energy and a second energy and (2) a beam adjustment system 3520 using an ion beam energy adjustment system 3440 designed to adjust energies of the treatment beam 269 between loadings of the ion beam. Each system if further described, infra. For clarity of presentation and without loss of generality, the synchrotron 130 is used to represent any accelerator type in the description of the two systems. The field accepted word of "ring" is used to describe a beam circulation path in a particle accelerator.

Referring still to FIG. 34, in the beam interrupt system 3510, an ion beam generation system 3410, such as the ion source 122, generates an ion, such as a cation, and a ring loading system 124, such as the injection system 120, loads the synchrotron 130 with a set of charged particles. An energy ramping system 3420 of the synchrotron 130 is used to accelerate the set of charged particles to a single treatment energy, a beam extraction system 3430 is used to extract one or more subsets of the charged particles at the single treatment energy for treatment of the tumor 720 of the patient 730. When a different energy of the treatment beam 269 is required, a beam dump system 3450 is used to dump the remaining charged particles from the synchrotron 130. The entire sequence of ion beam generation, accelerator ring loading, acceleration, extraction, and beam dump is subsequently repeated for each required treatment energy.

Referring still to FIG. 34, the beam adjustment system 3520 uses at least the ion beam generation system 3410, the ring loading system 124, the energy ramping system 3420, and the beam extraction system 3430 of the first system. However, the beam adjustment system uses an energy adjustment system 3440 between the third and fourth times, illustrated in FIG. 33A and FIG. 33B, where energy of the treatment beam 269 is decreased or increased, respectively. Thus, after extraction of the treatment beam 269 at a first energy, the energy adjustment system 3440, with or without use of the energy ramping system 3420, is used to adjust the energy of the circulating charged particle beam to a second energy. The beam extraction system 3430 subsequently extracts the treatment beam 269 at the second energy. The cycle of energy beam adjustment 3440 and use of the beam extraction system 3430 is optionally repeated to extract a third, fourth, fifth, and/or $n^{th}$ energy until the process of dumping the remaining beam and/or the process of loading the ring used in the beam interrupt system is repeated. The beam interrupt system and beam adjustment systems are further described, infra.

Figure 35:
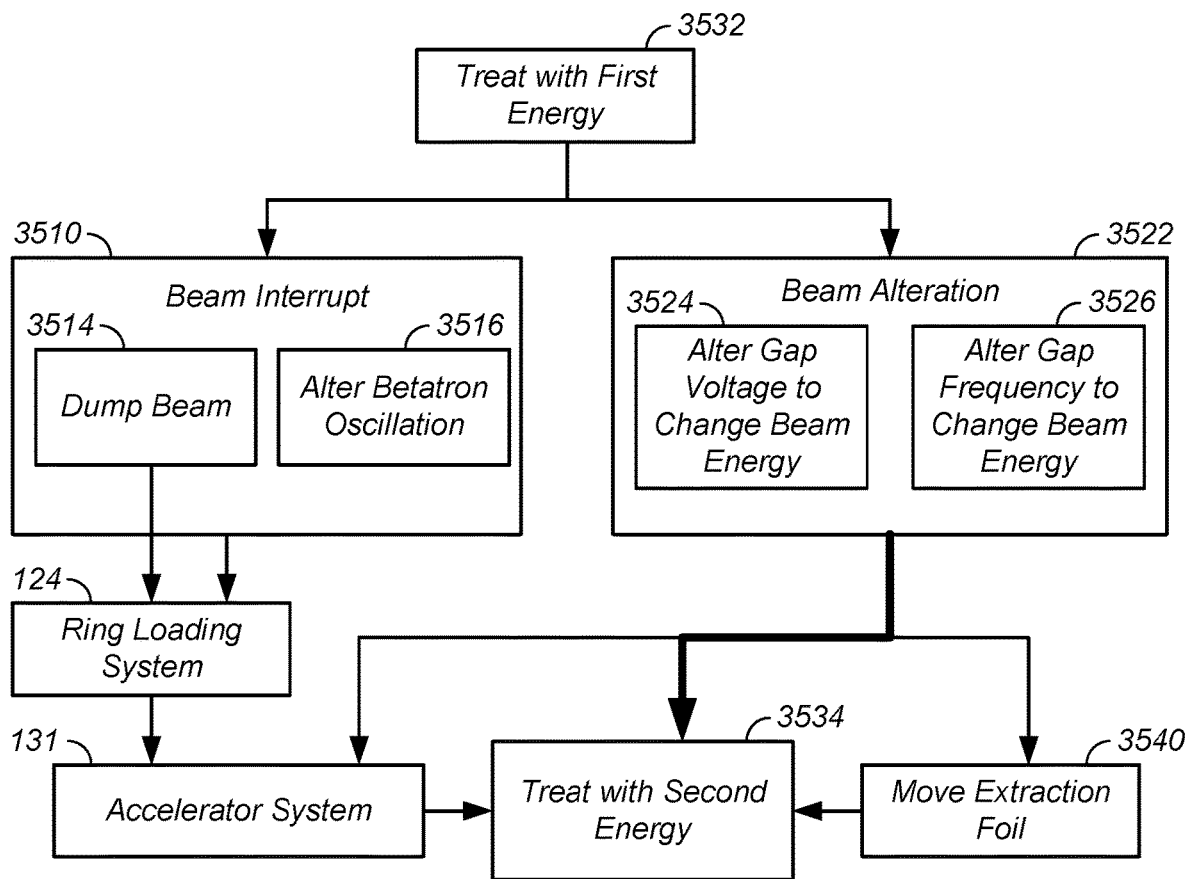
FIG. 35 illustrates a beam energy interrupt system.

Referring now to FIG. 35, the beam interrupt system 3510 is further described. After loading the ring, as described supra, the tumor 220 is treated with a first energy 3532. After treating with the first energy, the beam interrupt system 3510 uses a beam interrupt step, such as: (1) stopping extraction, such as via altering, decreasing, shifting, and/or reversing the betatron oscillation 3516, described supra, to reduce the radius of curvature of the altered circulating beam path 265 back to the original central beamline and/or (2) performing a beam dump 3514. After extraction is stopped and in the case where the beam is dumped, the ring loading system 124 reloads the ring with cations, the accelerator system 131 is used to accelerate the new beam and a subsequent treatment, such as treatment with a second energy 3534 ensues. Thus, using the beam interrupt system 3510 to perform a treatment at n energy levels: ions are generated, the ring is filled, and the ring is dumped n−1 times, where n is a positive integer, such as greater than 1, 2, 3, 4, 5, 10, 25, or 50. In the case of interrupting the beam by altering the betatron oscillation 2416, the accelerator system 131 is used to alter the beam energy to a new energy level.

Referring still to FIG. 35, the beam adjustment system 3520 is further described. In the beam adjustment system 3520, after the tumor 220 is treated using a first beam energy 3532, a beam alteration step 3522 is used to alter the energy of the circulating beam. In a first case, the beam is accelerated, such as by changing the beam energy by altering a gap voltage 3524, as further described infra. Without performing a beam dump 3514 and without the requirement of using the accelerator system 131 to change the energy of the circulating charged particle beam, energy of the circulating charge particle beam is altered using the beam alteration system 3522 and the tumor 220 is treated with a second beam energy 3534. Optionally, the accelerator system 131 is used to further alter the circulating charged particle beam energy in the synchrotron 130 and/or the extraction foil is moved 3540 to a non-beam extraction position. However, the inventor notes that the highlighted path, A, allows: (1) a change in the energy of the extracted beam, the treatment beam 269, as fast as each cycle of the charged particle through the ring, where the beam energy is optionally altered many times, such as on successive passes of the beam across the gap, between treatment, (2) treatment with a range of beam energies with a single loading of the beam, (3) using a larger percentage of the circulating charged particles for treatment of the tumor 220 of the patient, (4) a smaller number of charged particles in a beam dump, (5) use of all of the charged particles loaded into the ring, (6) small adjustments of the beam energy with a magnitude related to the gap radio-frequency and/or amplitude and/or phase shift, as further described infra, and/or (7) a real-time image feedback to the gap radio-frequency of the synchrotron 130 to dynamically control energy of the treatment beam 269 relative to position of the tumor 220, optionally as the tumor 220 is ablated by irradiation, as further described infra.

Figure 36:
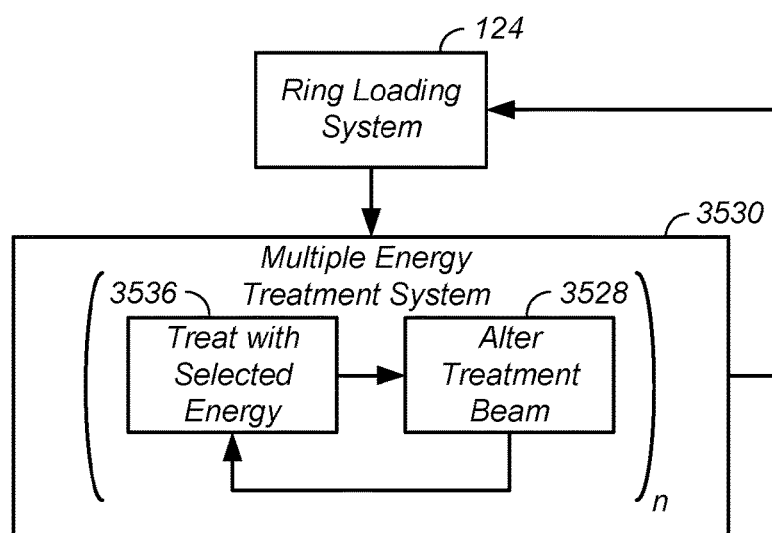
FIG. 36 illustrates a multiple energy treatment system.

Referring now to FIG. 36, the beam adjustment system 3520 is illustrated using multiple beam energies for each of one or more loadings of the ring. Particularly, the ring loading system 124 loads the ring and a multiple energy treatment system 3530 treats the tumor with a selected energy 3536, alters the treatment beam 3528, such as with the beam alteration process 3522, and repeats the process of treating with a selected energy and altering the beam energy n times before again using the ring loading system 124 to load the ring, where n is a positive integer of at least 2, 3, 4, 5, 10, 20, 50, and/or 100.

Referring now to FIG. 37A the beam alteration 3522 is further described. The circulating beam path 264 and/or the altered circulating beam path 265 crosses a path gap 3710 having a gap entrance side 3720 and a gap exit side 3730. A voltage difference, ΔV, across the path gap 3710 is applied with a driving radio field 3740. The applied voltage difference, ΔV, and/or the applied frequency of the driving radio field are used to accelerate or decelerate the charged particles circulating in the circulating beam path 264 and/or the altered circulating beam path 265, as still further described infra.

Referring now to FIG. 37B, acceleration of the circulating charge particles is described. For clarity of presentation and without loss of generality, a ninety volt difference is used in this example. However, any voltage difference is optionally used relative to any starting voltage. As illustrated, the positively charged particles enter the path gap 3710 at the gap entrance side 3720 at an applied voltage of zero volts and are accelerated toward the gap exit side 3730 at −90 volts. Optionally and preferably the voltage difference, that is optionally static, is altered at a radio-frequency matching the time period of circulation through the synchrotron.

Referring again to FIG. 37A, phase shifting the applied radio-frequency is optionally used to: (1) focus/tighten distribution of a circulating particle bunch and/or (2) increase or decrease a mean energy of the particle bunch as described in the following examples.

Example I

Referring again to FIG. 37B, in a first genus of a lower potential at the gap exit side 3730 relative to a reference potential of the gap entrance side 3720, in a first species case of the applied radio-frequency phase shifted to reach a maximum negative potential after arrival of a peak intensity of particles in a particle bunch, circulating as a group in the ring, at the gap exit side 3730, then the trailing charged particles of the particle bunch are accelerated relative to the mean position of charged particles of the particle bunch resulting in: (1) focusing/tightening distribution of the circulating particle bunch by relative acceleration of a trailing edge of particles in the particle bunch and (2) increasing the mean energy of the circulating particle bunch. More particularly, using a phase matched applied radio-frequency field, a particle bunch is accelerated. However, a delayed phase of the applied radio-frequency accelerates trailing particles of the particle bunch more than the acceleration of a mean position of the particle bunch, which results in a different mean increased velocity/energy of the particle bunch relative to an in-phase acceleration of the particle bunch. In a second species case of the applied radio-frequency phase shifted to reach a maximum negative potential before arrival of a peak intensity of particles in the particle bunch at the gap exit side 3730, then the leading charged particles of the particle bunch are accelerated less than the peak distribution of the particle bunch resulting in: (1) focusing/tightening distribution of the circulating particle bunch and/or (2) an acceleration of the circulating particle bunch differing from an in-phase acceleration of the particle bunch.

Example II

Referring again to FIG. 37C, in a second genus of a larger potential at the gap exit side 3730 relative to the gap entrance side 3720, using the same logic of distribution edges of the bunch particles accelerating faster or slower relative to the mean velocity of the bunch particles depending upon relative strength of the applied field, the particle bunch is: (1) focused/tightened/distribution reduced and (2) edge distributions of the particle bunch are accelerated or decelerated relative to deceleration of peak intensity particles of the particle bunch using appropriate phase shifting. For example, a particle bunch undergoes deceleration across the path gap 3710 when a voltage of the gap exit side 3730 is larger than a potential of the gap entrance side 3720 and in the first case of the phase shifting the radio-frequency to initiate a positive pulse before arrival of the particle bunch, the leading edge of the particle bunch is slowed less than the peak intensity of the particle bunch, which results in tightening distribution of velocities of particles in the particle bunch and reducing the mean velocity of the particle bunch to a different magnitude than that of a matched phase radio-frequency field due to the relative slowing of the leading edge of the particle bunch. As described above, relative deceleration, which is reduced deceleration versus the main peak of the particle bunch, is achieved by phase shifting the applied radio-frequency field peak intensity to lag the peak intensity of particles in the particle bunch.

Example III

Referring again to FIG. 37A and FIG. 37B, optionally more than one path gap 3710 is used in the synchrotron. Assuming an acceleration case for each of a first path gap and a second path gap: (1) a phase trailing radio-frequency at the first path gap accelerates leading particles of the particle bunch less than acceleration of the peak intensity of particles of the particle bunch and (2) a phase leading radio-frequency at the second path gap accelerates trailing particles of the particle bunch more than acceleration of the peak intensity of particles of the particle bunch. Hence, first particles at the leading edge of the particle bunch are tightened toward a mean intensity of the particle bunch and second particles at the trailing edge of the particle bunch are also tightened toward the mean intensity of the particle bunch, while the particle bunch as a whole is accelerated. The phase shifting process is similarly reversed when deceleration of the particle bunch is desired.

In addition to acceleration or deceleration of the beam using applied voltage with or without phase shifting the applied voltage, geometry of the gap entrance side 3720 and/or the gap exit side 3730 using one or more path gaps 3710 is optionally used to radially focus/tighten/distribution tighten the particle bunch. Referring now to FIG. 38, an example illustrates radial tightening of the particle bunch. In this example, a first path gap 3712 incorporates a first curved geometry, such as a convex exit side geometry 3812, relative to particles exiting the first path gap 3712. The first curved surface yields increasingly convex potential field lines 3822, relative to particles crossing the first path gap 3712, across the first path gap 3712, which radially focuses the particle bunch. Similarly, a second path gap 3714 incorporates a second curved geometry or a concave entrance side geometry 3814, relative to particles entering the second path gap 3714. The second curved surface yields decreasingly convex potential field lines 3824 as a function of distance across the second path gap 3714, which radially defocuses the particle bunch, such as back to a straight path with a second beam radius, $r_2$, less than a first beam radius, $r_1$, prior to the first path gap 3712.

Dynamic Energy Adjustment

Referring again to FIG. 3A through FIG. 38, the energy of the treatment beam 269 is controllable using the step of beam alteration 3426. As the applied voltage of the driving radio frequency field 3740 is optionally varied by less than 500, 200, 100, 50, 25, 10, 5, 2, or 1 volt and the applied phase shift is optionally in the range of plus or minus any of: 90, 45, 25, 10, 5, 2, or 1 percent of a period of the radio frequency, small changes in the energy of the treatment beam 269 are achievable in real time. For example, the achieved energy of the treatment beam in the range of 30 to 330 MeV is adjustable at a level of less than 5, 2, 1, 0.5, 0.1, 0.05, or 0.01 MeV using the beam adjustment system 3520. Thus, the treatment beam 269 is optionally scanned along the z-axis and/or along a z-axis containing vector within the tumor 220 using the step of beam alteration 3522, described supra. Further, any imaging process of the tumor and/or the current position of the treatment beam 269, such as the positron emission tracking system, is optionally used as a dynamic feedback to the main controller 110 and/or the beam adjustment system 3520 to make one or more fine or sub-MeV adjustments of an applied energy of the treatment beam 269 with or without interrupting beam output, such as with use of the accelerator system 131, dumping the beam 3514, and/or loading the ring 124.

Tumor Targeting

Targeting the tumor 220, in addition to z-axis energy control of the treatment beam 269, involves scanning the charged particle beam transport path 268 along the x/y-plane. Scanning the charged particle beam transport path is accomplished using a first square dipole magnet to deflect the charged particle beam path 268 in a first direction, such as along the x-axis, and a second square dipole magnet, in series with the first square dipole magnet, to deflect the charged particle beam path 268 in a second direction. However, because the beam is deflected by the first square dipole magnet before it arrives at the second square dipole magnet, a second pole gap of the second magnet must necessarily be larger than a minimum size of a first pole gap of the first square dipole magnet to accommodate the scanned beam. An increased size of magnetic inductance of the second square dipole magnet limits speed at which current is passed through the magnet, which limits scanning speed of the second square dipole magnet and consequently limits how quickly the beam can be scanned. Further, physically bulky magnets require more power, require more cooling, and add length to the charged particle beam transport path, which decreases accuracy targeting the treatment beam 269. A single-origin scanner, described infra, eliminates the second slower square dipole magnet, dramatically speeding up the scanning time of the system and simultaneously reducing its longitudinal size, all while maintaining symmetry in the x-scan direction and the y-scan direction.

Referring now to FIGS. 39(A-D) a single magnet of a double dipole scanning system 3900 is described, where multiple uses of the single magnet in the double dipole scanning system is subsequently described, FIGS. 39(E-H).

Figure 39A:
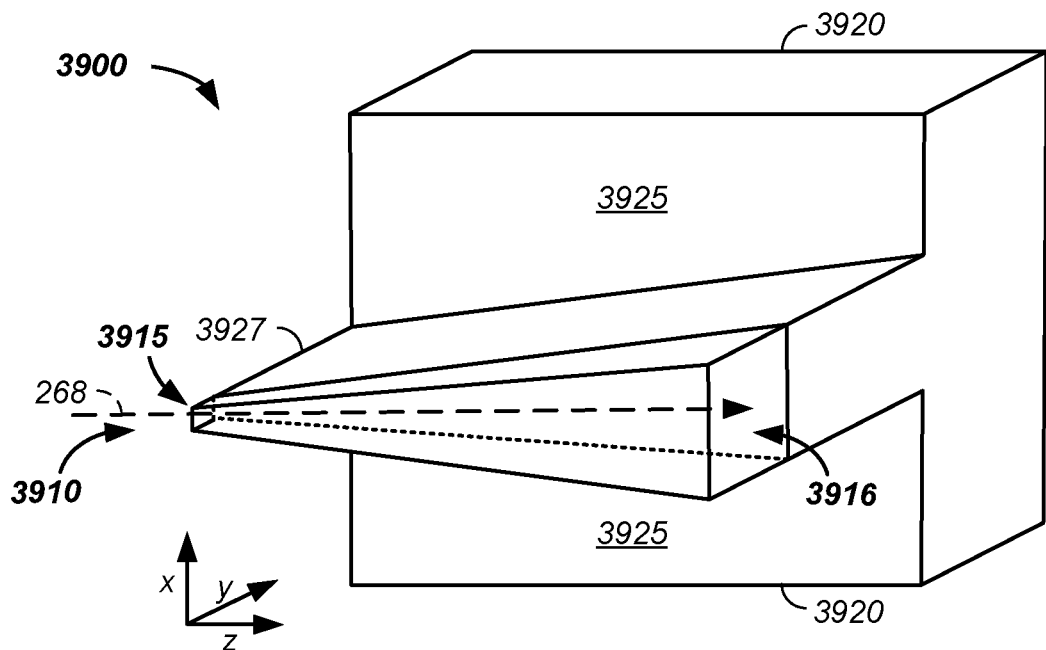
FIG. 39A illustrates an expanding beam path.

Referring now to FIG. 39A, the double dipole scanning system 3900 or the double dipole magnet scanning system circumferentially encloses a longitudinal path of an expanding cross-section 3910 of the charged particle beam transport path 268 from an entry side 3915 of the double dipole scanning system 3900 to an exit side 3916 of the double dipole scanning system 3900, as a function of travel along the z-axis.

Still referring to FIG. 39A, a magnetic flux return element 3920 is described. Generally, the magnetic flux return element 3920 comprises a yoke or base return element, such as steel, for carrying a magnetic field with a first inner surface 3925 and a magnet core 3927. As illustrated, the magnet core 3927 has a second inner surface 3929 and/or cross-section shape that: matches a side of the expanding cross-section of the expanding cross-section 3910 of the charged particle beam transport path 268 from an entry side 3915 of the double dipole scanning system 3900, along the z-axis of the charged particle beam transport path 268, to an exit side 3916 of the double dipole scanning system 3900 and/or has a trapezoid shape/a trapezoidal prism geometry. Magnet windings 3930, not illustrated in FIG. 39A for clarity of presentation and further described infra, wrap longitudinally around the magnet core 3927.

Figure 39B:
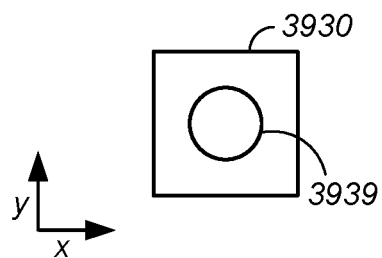
FIG. 39B illustrates a hollow core winding.

Referring now to FIG. 39B, a magnet winding 3930 or magnet coil is further described. Generally, the magnet winding 3930 comprises any cross-section shape, such as round, square, or rectangular. Optionally and preferably, the magnet winding 3930 comprises a longitudinal plenum 3939 or path and/or is a hollow core inductor, such as for internal flow of a coolant. Herein, a winding, of the magnet winding 3930, using with a longitudinal internal path is referred to as a hollow core winding.

Figure 39C:
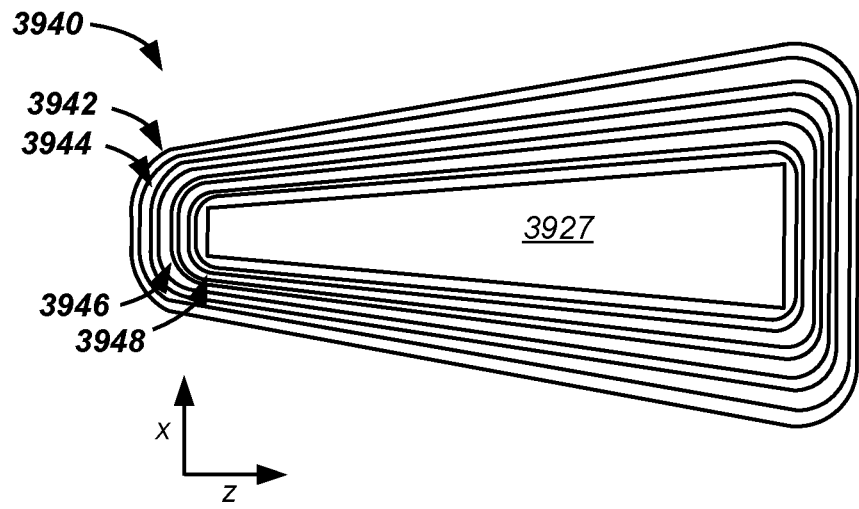
FIG. 39C and FIG. 39D illustrate multiple winding layers.

Referring now to FIG. 39C, windings of the double dipole scanning system 3900 are described. Optionally and preferably the windings comprise layers of trapezoidal windings 3940 around the magnet core 3927. A first winding layer 3942, a second winding layer 3944, a third winding layer 3946, and a fourth winding layer 3948 of the trapezoidal windings 3940 are illustrated, where the winding comprise n layers, where n is a positive integer of at least 1, 2, 3, 4, or 5.

Figure 39D:
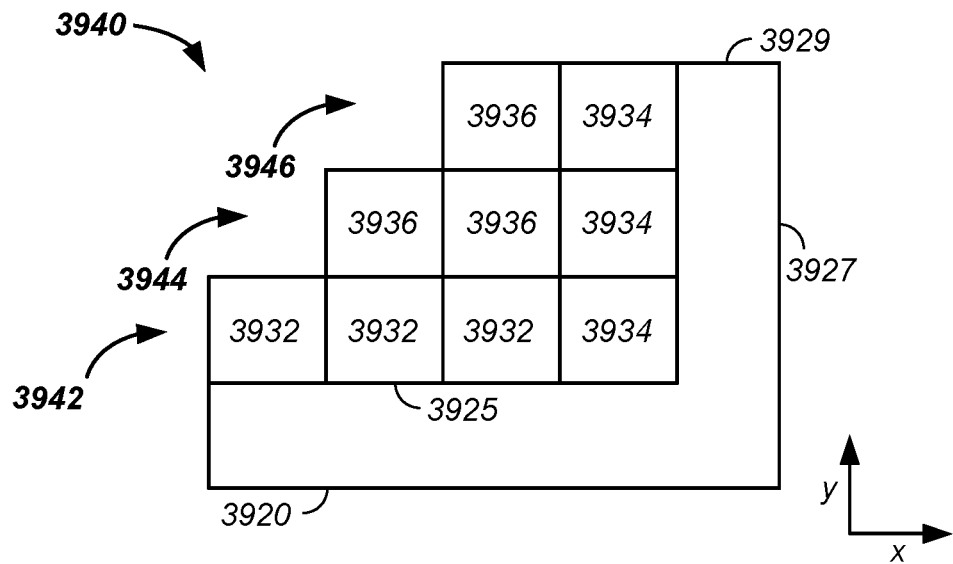

Referring now to FIG. 39D, the rounded corner trapezoidal windings 3940 are further described. Here, the magnetic flux return element 3920 is illustrated with the magnet core 3927 extending from the first inner surface 3925 of the magnet flux return element 3920 to the second inner surface 3929 of the magnet core 3927 proximate the charged particle beam transport path 268. The trapezoidal windings 3940 form layers from proximate the first inner surface 3925 to proximate the second inner surface 3929, which is adjacent to the longitudinal path of an expanding cross-section 3910 of the charged particle beam transport path 268. Optionally, the trapezoidal windings 3940 comprise multiple, optionally electrically parallel, windings to facilitate cooling. A first winding 3932 of the trapezoidal windings 3940 is illustrated having three winding turns in a single winding layer, the first winding layer 3942. A second winding 3934 of the trapezoidal windings 3940 is illustrated having winding turns in multiple winding layers, the first winding layer 3942, the second winding layer 3944, and the third winding layer 3946. A third winding 3936 of the trapezoidal windings 3940 is illustrated having multiple winding turns in a single winding layer, the second winding layer 3944, and multiple winding turns in a column of winding turns. Generally, the winding turns comprise any three-dimensional winding geometry. such as a truncated trapezoidal pyramid and/or a truncated even number sided pyramid. Optionally and preferably, individual windings of multiple windings are configured to remove heat from the magnet core 3927 and/or to have accessible input and output ends for coolant flow.

Figure 39E:
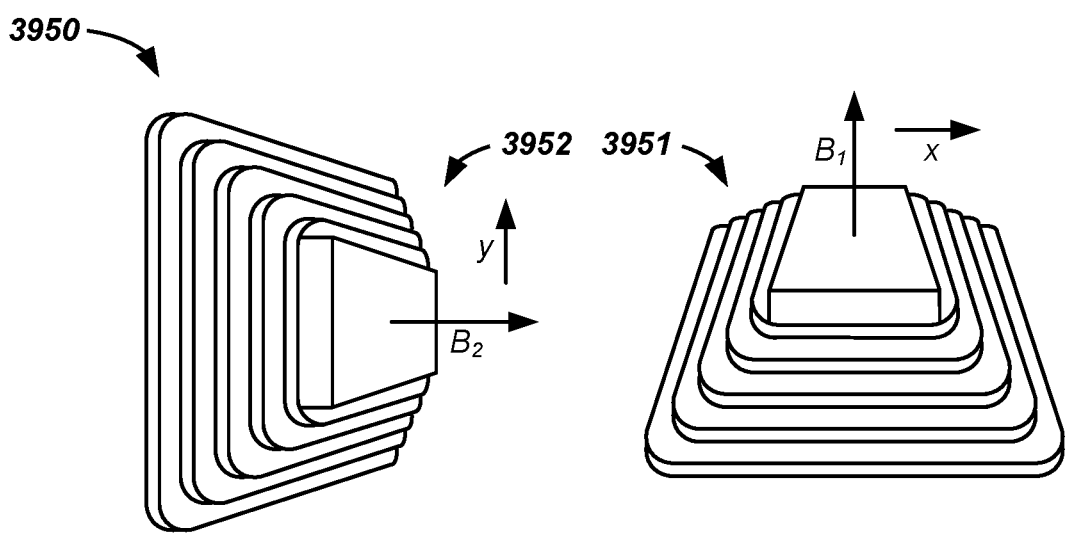
FIG. 39E illustrates multiple truncated rounded corner truncated pyramid sections.

Referring now to FIG. 39E, two truncated pyramid windings 3950 are illustrated, which are examples of the trapezoidal windings 3940 wound around first and second magnet cores 3927, respectively. Particularly, a first truncated pyramid winding section 3951 is used as one-half of a first dipole used to provide a first magnetic field, $B_1$, used to scan an x-axis of the charged particle beam transport path 268 and second truncated pyramid winding section 3952 is used as one-half of a second dipole used to provide a second magnetic field, $B_2$, used to scan a y-axis of the charged particle beam transport path 268, as further described infra.

Referring now to FIG. 39F, four truncated pyramid windings 3950 are illustrated pivoted away from the central charged particle beam transport path 268. As illustrated, the first truncated pyramid winding section 3951 and a third truncated pyramid section 3953 form opposite sides of the first dipole used to provide the first magnetic field, $B_1$, used to scan the x-axis of the charged particle beam transport path 268 and the second truncated pyramid winding section 3952 and a fourth truncated pyramid section 3954 form opposite sides of the second dipole used to provide the second magnetic field, $B_2$, used to scan the y-axis of the charged particle beam transport path 268. Herein, for clarity of presentation and without loss of generality, the first truncated pyramid winding section 3951, the second truncated pyramid winding section 3952, the third truncated pyramid winding section 3953, and the fourth truncated pyramid winding section 3954 are referred to as a bottom coil, left coil, top coil, and right coil, respectively. The first dipole, comprising the first and third truncated pyramid sections 3951, 3953, and the second dipole, comprising the second and fourth truncated pyramid sections 3952, 3954, combine to form a double dipole. When set at right angles to one another, the double dipole is referred to as an orthogonal double dipole and the system is referred to as the double dipole magnet scanning system 3900.

Optionally and preferably, the four truncated pyramid windings are of the same design for ease of manufacturing and control.

Referring now to FIG. 39G, the double dipole scanning system 3900 is illustrated with four truncated pyramid sections respectively attached to four magnet cores and base sections, which forms two dipole scanning systems operating on the same volume, line segment, and/or point of the charged particle beam transport path 268. Particularly, a first magnet dipole section 3921 and a third magnet dipole section 3923 are used in forming the first magnetic field, $B_1$, used to scan the x-axis and a second magnet dipole section 3922 and a fourth magnet dipole section 3924 are used in forming the second magnetic field, $B_2$, used to scan the y-axis where the base metallic sections of the four magnet dipole sections are jointly used to form return yokes of the first and second magnetic fields, $B_1$ and $B_2$, which are representatively illustrated. As illustrated, the charged particle beam transport path 268 travels through the entrance side 3915 of the expanding section 3910 of a beam path chamber and emerges out of the illustration through the exit side 3916 of the double dipole scanning system 3900.

Referring now to FIG. 39H, a perspective view of the beam path chamber 3910 is illustrated, which is circumferentially surrounded by the first through fourth truncated pyramid winding sections 3951-3954, not illustrated for clarity of presentation. The exit side 3916 is optionally and preferably at least 10, 20, 30, 50, 100, 200, 500, or 1000 percent larger in terms of length, width, and/or area than the entrance side 3915.

Cooling

Figure 39I:
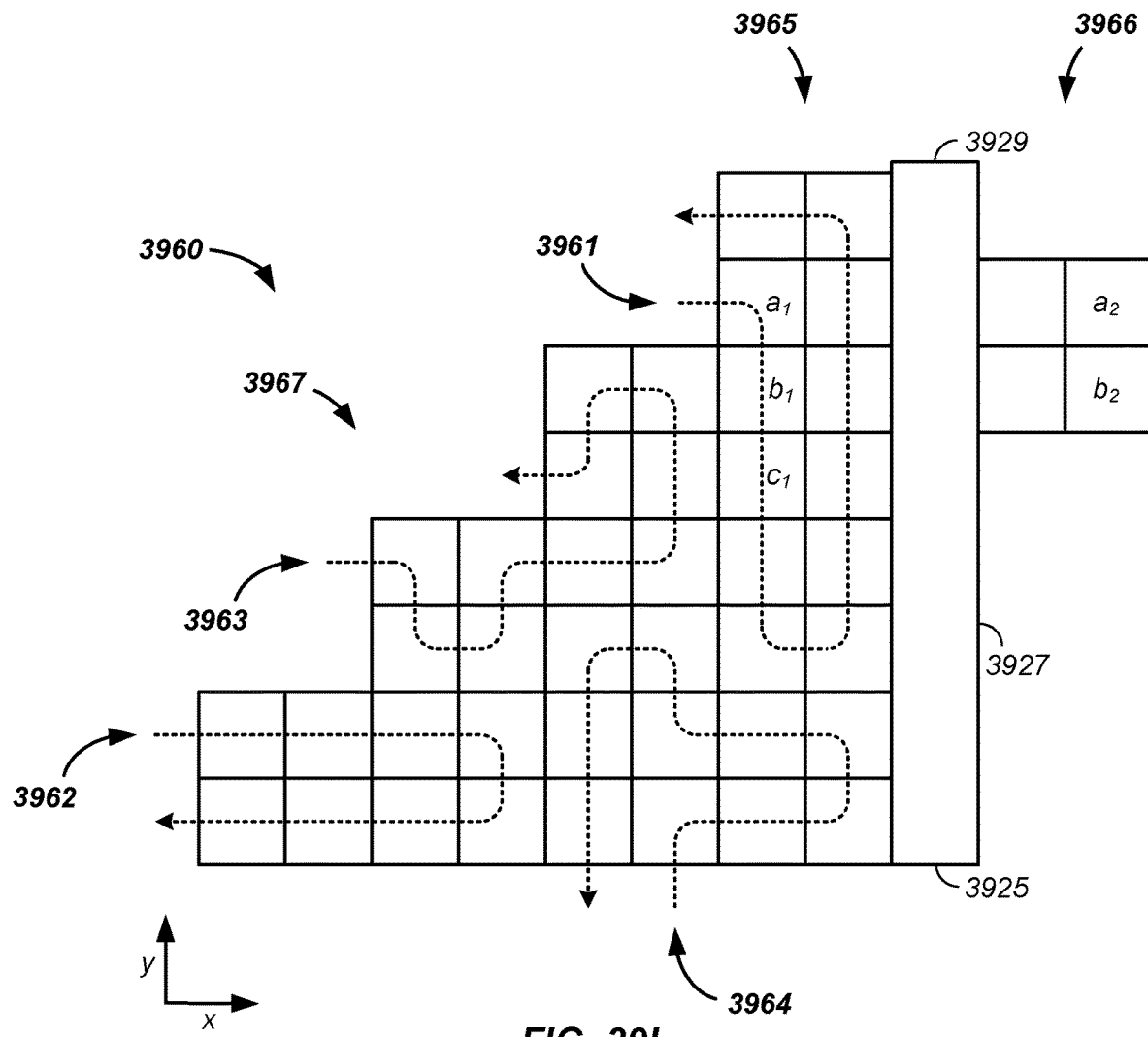
FIG. 39I illustrates a hollow core winding cooling system.

Referring now to FIG. 39I, windings of an optional double dipole cooling system 3960 are described. For clarity of presentation, the trapezoidal windings 3940 around the magnet core 3927 are illustrated, in an x/y-plane cross-section, for one side of one-half of a dipole section relative to the magnet core 3927 for the dipole section. Again for clarity of presentation, the trapezoidal windings 3940 along a first side 3965 of the magnet core 3927 are illustrated and only a subset of the trapezoidal windings 3940 are illustrated along a second side 3966 of the magnet core 3927. Thus, as illustrated, a first turn of a first winding 3961 passes along the first side 3965 of the magnet core 3927 through section $a_1$ and returns along the second side 3966 of the magnet core through section $a_2$ before returning in a second turn through section $b_1$, completing the second turn through section $b_2$, and initiating a third turn in section $c_1$. Thus, the dotted lines in FIG. 39I refer to the progression of turns in the given winding. Generally, n turns are used for a winding, where n is positive integer that is optionally different for each winding, as further described infra.

Still referring to FIG. 39I, cooling of the windings in the double dipole cooling system 3960 is described. One or more of the trapezoidal windings 3940 of the double dipole cooling system 3960 comprises a hollow core winding, such as illustrated in FIG. 39B. Referring still to FIG. 39I, the magnet coil is illustrated with a set of windings 3967: a first winding 3961, a second winding 3962, a third winding 3963, and a fourth winding 3964. Optionally and preferably, a coolant is pumped through the longitudinal plenum 3939 or hollow core of each winding. The coolant is moved from a reservoir and/or circulated through the set of windings using a pump and typically comprises a heat exchange element outside of the magnet coil. Generally, any number of hollow core windings are used in the magnet coil.

Still referring to FIG. 39I, current flow carried by the windings in the double dipole cooling system 3960 is described. Optionally and preferably, the set of windings 3967 are wound electrically in parallel. A length of a turn in a winding increases with radial distance from the magnet core 3927. Thus, to maintain a uniform length of each winding in the set of windings 3967, a differing number of turns for one or more of the individual windings in the set of windings 3967 is optionally and preferably used. The uniform length of the windings is used for control of current and voltage. Generally, a first length of a one winding is within 1, 2, 3, 5, 10, or 20 percent of a length of a another winding in the set of windings 3967 and/or all windings within the set of windings 3967 comprise individual lengths within 1, 2, 3, 5, 10, or 20 percent of a mean length of the windings in the set of windings 3927.

Still referring to FIG. 39I, winding paths of the set of windings 3967 are described. As illustrated, the first winding 3961 contains twelve turns and has a first length matching a second length of the second winding 3962 containing eight turns as a second mean radius of the turns in the second winding 3962 is greater than a first mean radius of turns in the first winding 3961. As illustrated, the third winding 3963 and the fourth winding 3964, having lengths matching the first length and second length, are illustrated with ten turns each. Each winding of the set of windings 3967 comprises a coolant entrance and a coolant exit, connected to the pump, along an outside perimeter of a volume of the windings in the trapezoidal windings 3940. Paths of individual windings in the set of windings are optionally wound: at one or more x-axis distances from the magnet core 3927 and/or along one or more y-axis layers of the set of layers. Generally, turns of a winding comprises any winding path around the magnet core 3927.

Generally, the dual dipole scanning system:
forms a single four poled dual axis scanner;
uses dipoles arranged in a scanning quadrupole configuration;
comprises four identical modular quadrants bolted together to form a steering quadrupole;
is optionally mounted in front of a smaller focusing quadrupole;
uses top and bottom quadrants steering in the x-direction and left and right quadrants providing steering in the y-direction;
allows simultaneous lateral steering in both the x-direction and the y-direction at the same point in space;
includes a pole tapered smaller at the entrance end and wider at the exit end of the scanner, which allows the pole gap to be only as wide as it needs to be, which allows a less intense magnetic field reducing the electric current to drive the coil and a smaller coil with lower inductance for faster scanning;
uses dipoles powered separately, but the power supplies are optionally identical;
optionally independently power supplies are used to provide unequal current and/or voltage profiles as a function of time for each coil allowing for magnetic field configurations more complicated than two simple dipole fields superimposed;
optionally uses rounded steel faces of the quadrants and/or poles to yield a constant pathlength through the magnetic scanner at any deflection angle;
optionally uses poles wrapped with hollow core water/liquid-cooled copper conductors that form the coils of the magnet;
has a trumpet or truncated pyramidal shape quadrupole in the direction of the beam, the z-axis, which allows the beam to be deflected over the entire angular volume while utilizing the least amount of longitudinal space;
has a tapered shape reducing the magnetic volume and field strength necessary to deflect the beam within a given volume;
simplifies the software controlling beam scanning, which previously had to compensate for a different beam origin at every spot; and/or
results in a very low inductance system, and therefore a very high scanning speed, which improves treatment times in spot-dose systems and results in substantial time savings for continuous dosing systems.

Multi-Color/Multi-Layer Scintillator

A detector system is described using multiple scintillation layers. Generally, differing detector materials, set at different depths into a detector element, generate photons at different wavelengths. Using the differing wavelengths, referred to herein as colors, and differing responsivity of the differing detector materials, in terms of number of photons per passing energy of the positively charged particle beam, and/or known depths of the scintillator materials, energy of the residual charged particle beam 267 is derived with subsequent image development/image calculation based on the determined energy of the residual charged particle beam 267. The multiple scintillation later/multi-color detector system is further described, infra.

Figure 40:
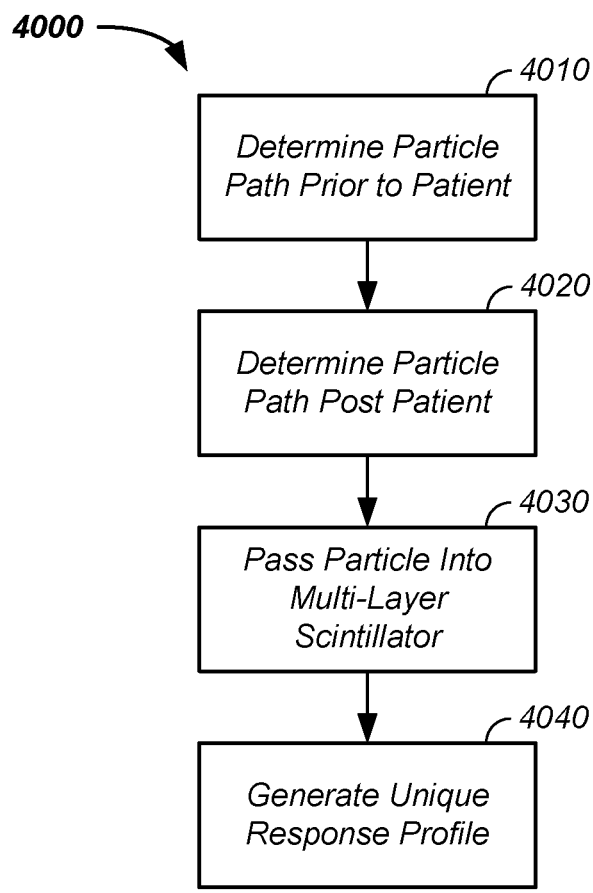
FIG. 40 illustrates a method of using a multi-color scintillator.
Figure 41:
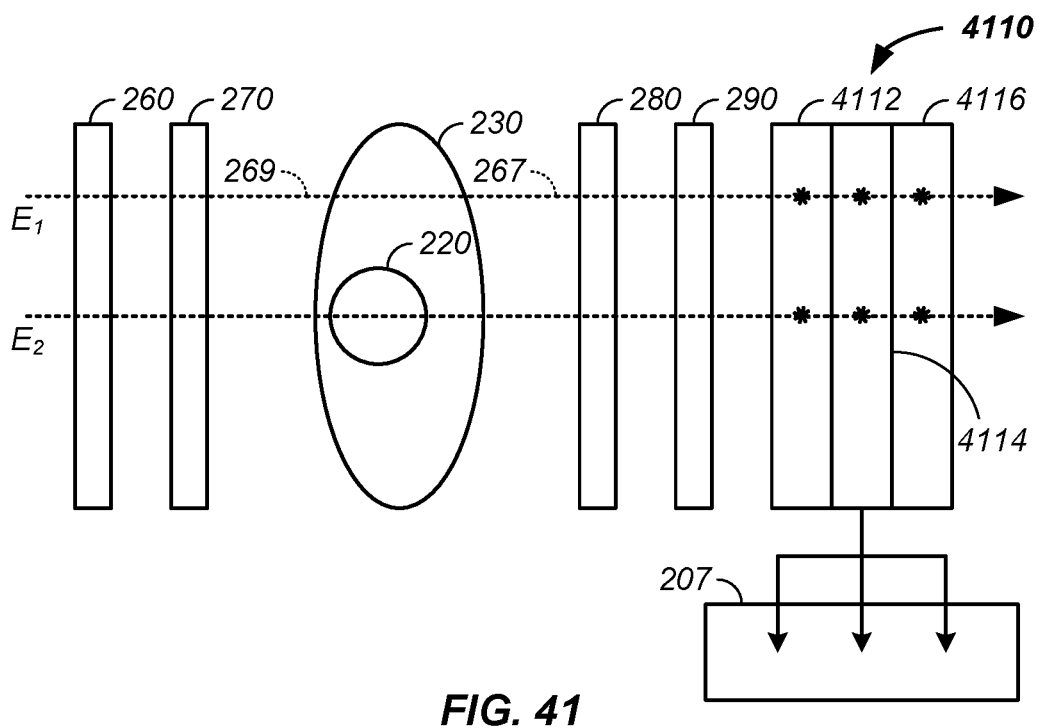
FIG. 41 illustrates a multi-color/multi-layer scintillator.

Referring now to FIG. 40 and FIG. 41, a beam state, position and/or residual energy, determination system 4000 is described. As described, supra, a prior or pre-patient position of the treatment beam 269 and a posterior or post patient position of the residual charged particle beam 267 are used to determine an actual treatment path, such as through the tumor 220 of the patient 230. As illustrated, a first process of determining a prior location 4010 of the treatment beam 269 uses the first tracking plane 260 and the second tracking plane 270. Similarly, a second process of determining a post location 4020 of the residual charged particle beam 267 uses the third tracking plane 280 and the fourth tracking plane 290. In combination with location determination of the charged particle beam, an energy of the residual charged particle beam 267 is determined as part of an imaging process. A third process of passing the charged particles into a multi-layer scintillator 4030 is illustrated where the residual charged particle beam 267 passes at least into and optionally through a multi-layer scintillator detector element 4110. As illustrated, the multi-layer scintillator comprises a first scintillation layer 4112, a second scintillation layer 4114, and a third scintillation layer 4116. However, the multi-layer scintillator detector element 4110 optionally includes n layers, where n is a positive integer of more than 1, 2, 3, 4, 5, 10, or 15 layers or, as described infra, groups of repeating layers. Using secondary photons, resultant from energy deposition and passage/proximity of the residual charged particle beam, emitted from 1, 2, 3, or more scintillation layers of the multi-layer scintillator detector element 4110 a fourth process of generating a secondary photon beam intensity response profile 4040 is performed, such as via use of a scintillation detection system 207.

Still referring to FIG. 40 and FIG. 41, the scintillation detection system 207 is any electro-optical and/or electro-mechanical system used to quantify at least a number of photons resultant from each of the two or more layers of the multi-layer scintillator detector element 4110 and is optionally and preferably used to determine location of the secondary photons. For example, a camera and/or photodetector is used to image the secondary photons, which yields quantifiable information on both x/y-plane location of emission and z-axis energy of the residual charged particle beam 267.

For clarity of presentation and without loss of generality, a series of examples are used to further describe the beam state, position and/or residual energy, determination system 4000.

Example I

Figure 42A:
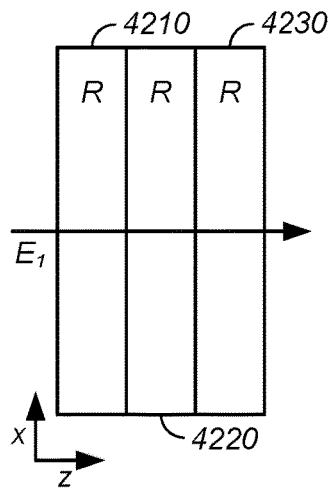
FIG. 42A and FIG. 42B illustrate a multi-layer scintillator and a response curve, respectively.
Figure 42B:
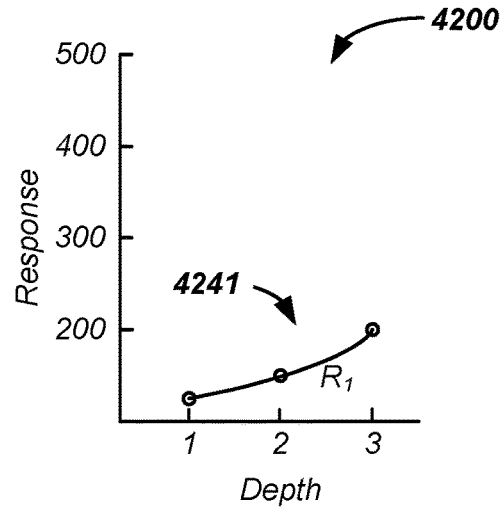

Referring now to FIG. 42A and FIG. 42B, a multi-layer single-color scintillation detector element 4200, a species of the multi-layer scintillator 4030, is described where each scintillation layer uses the same scintillation material and/or emits the photons in a same wavelength range. As illustrated, the first scintillation layer 4111 is a first red photon emission layer 4210, the second scintillation layer 4114 is a second red photon emission layer 4220, and the third scintillation layer 4116 is a third red photon emission layer 4230. Again, for clarity of presentation, red photons are illustrative of any wavelength range common to all three of the first, second, and third photon emission layers 4210, 4220, 4230. Referring now to FIG. 42B, for a first energy beam, E1, a first intensity/magnitude response shape, $R_1$, or first response curve 4241, such as a relative number of secondary photons, emitted from each of the first, second, and third red photon emission layers 4210, 4220, 4230, is illustrated. Generally, as the residual energy particle beam 267 traverses through the scintillation layers, the residual energy particle beam loses energy and slows down. Slower particles lose more energy per unit distance traversed than the faster particles resulting in still more lost energy and slowing of the particles, which results in a Bragg peak. The number of secondary photons produced is proportional to the amount of energy released by the charged particles into the scintillation material. Thus, as the charged particles progress into the multi-layer scintillator, more photons are generated per millimeter of travel and the shape of the response curve as a function of depth can be related to initial energy of the residual energy particle beam 267 via calibration. Again, energy of the residual energy particle beam 267 is used to generate an image, such as proton computed radiography (pRT) image and/or a proton computed tomography (pCT) image in conjunction with beam scanning, relative movement of the patient 230 relative to the scanning beam, and/or relative rotation of the patient 230 relative to the scanning beam.

Example II

Figure 43A:
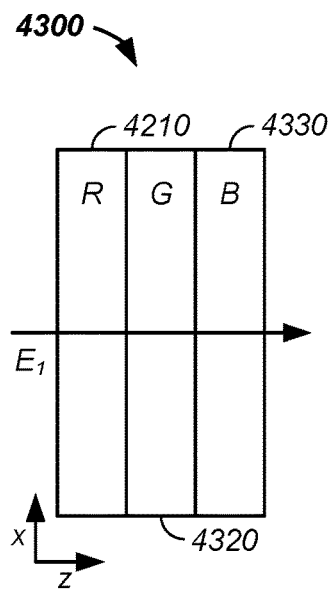
FIG. 43A illustrates a multi-layer scintillator with response curves for single color scintillators, FIG. 43B, and mixed color scintillators, FIG. 43C, respectively.
Figure 43B:
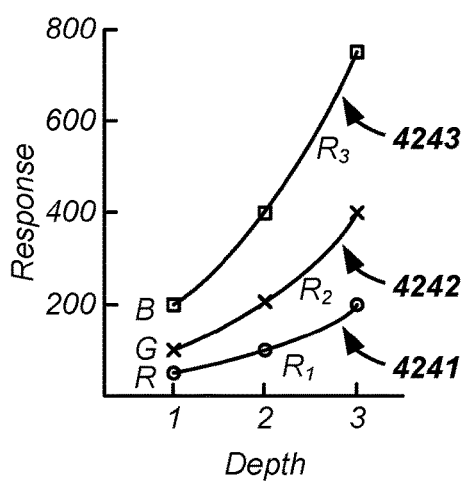

Referring now to FIG. 43A and FIG. 43B, a multi-layer multi-color scintillation detector element 4300, a species of the multi-layer scintillator 4030, is described where at least two z-axis layers differ in wavelength ranges of emitted secondary photons. As illustrated, the first scintillation layer 4111 is the first red (R) photon emission layer 4210, the second scintillation layer 4114 is a green (G) photon emission layer 4320, and the third scintillation layer 4116 is a blue (B) photon emission layer 4330. Again, for clarity of presentation, red, green, and blue photons are illustrative of a set of wavelength ranges of the respective first, second, and third photon emission layers 4210, 4220, 4230 and emission wavelengths include ultraviolet and infrared light. Use of different scintillation materials emitting light in differing wavelength regions is optionally and preferably used to enhance resolution of a depth of penetration and/or an original energy of the residual energy particle beam 267 through reduction of cross-talk between layers. To clarify, in the case of a standard camera using a Bayer matrix, elements covered by filters are used to detect red, green, or blue light, where standard detector arrays provide x/y-plane resolution and the standard Bayer matrix yields z-axis resolution of position the charged particle beam. Optionally and preferably, one or more two-dimensional detector arrays are optically coupled to a set of transmission filters with out of emission band blocking elements are keyed, respectively, to wavelengths of emissions from a set emission layers with corresponding emission elements in the multi-layer scintillator 4030.

Example III

Referring still to FIG. 43A and FIG. 43B, the multi-layer multi-color scintillation detector element 4300 is further described. For clarity of presentation and without loss of generality, a blue (B) emission scintillation layer, such as the third emission layer 4330 has a greater responsivity, photons emitted per millimeter of beam travel, than a green (G) emission scintillation layer, such as the second emission layer 4320, which has a greater responsivity than a red (R) emission scintillation layer, such as the first red (R) photon emission layer 4210 described in the second example. Thus, in a first case of a red scintillator used in each of the first, second, and third scintillation layers, the first response curve 4241, described in the first example, is generated. Similarly, in a second case of a green scintillator used in each of the first, second, and third scintillation layer, a second response curve 4242 is generated. Similarly, in a third case of a blue scintillator used in each of the first, second, and third scintillation layer, a third response curve 4243 is generated. Referring now to FIG. 43B, for a given depth, the more responsive blue emission scintillation layer yields a higher signal than the less responsive green emission scintillation layer, which yields a greater response than the still less responsive red emission scintillation layer. Further, the spread between the exemplary response curves increases with depth of penetration of the charged particles into the multi-layer scintillator 4030 as a greater lost energy, resultant in the higher response, slows the charged particles more resulting in a still greater loss of energy of the charged particle, as described supra. Thus, three unique response curves are generated; in this example, all of the response curves having a non-linear shape.

Example IV

Figure 43C:
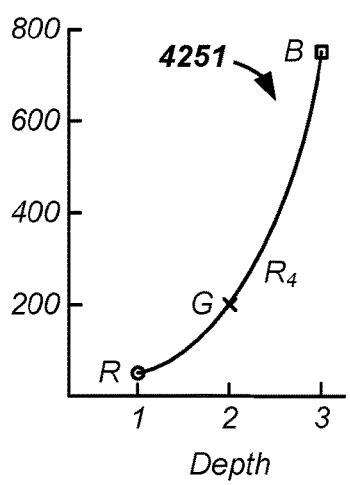

Referring still to FIG. 43A and FIG. 43B and referring now to FIG. 43C, the multi-layer multi-color scintillation detector element 4300 is further described. In FIG. 43C, the first response of the first red (R) photon emission layer 4210 at the first depth is plotted with both the second response of the green photon emission layer 4320 at the second depth and the third response of the blue photon emission layer 4330 at the third depth. By effectively using the first point of the first response curve 4241, the second point of the second response curve 4242, and the third point of the third response curve 4243, relative to the first, second, and third response curves, an amplified response curve with a greater slope and an enhanced curve shape is generated, which is referred to herein as a first multi-color response curve 4251. The first multi-color response curve is combined and compared with additional multi-color response curves, as further described infra.

Example V

Referring now to FIG. 44, a stacked detector element 4400 of the beam state, position and/or residual energy, determination system 4000 is described. The stacked detector element includes multiple sub-stacks, where each sub-stack is a unit block of two or more scintillation layers of different wavelength of emission. As illustrated, for clarity of presentation and without loss of generality, the stacked detector element 4400 comprises four repeating sub-stacks with three scintillation layers per sub-stack. As illustrated, the first sub-stack 4301 is a first set of red, green, and blue scintillation layers, such as the multi-layer multi-color scintillation detector element 4300. A second sub-stack 4302, a third sub-stack 4303, and a fourth sub-stack 4304 are repeating units of the first sub-stack 4301, where the set of sub-stacks are optionally close packed along the z-axis and/or as illustrated have a small gap between each sub-stack. More generally, the sub-stack comprises any number of scintillation layers and any number of scintillation colors where the scintillation colors are ordered in any order along the z-axis of the charged particles. Further, the stacked detector element 4400 optionally contains different types of sub-stacks, such as 2, 3, 4, or more color sub-stacks. Still further, each layer of a given sub-stack type is optionally any thickness, such as thicker or thinner than a neighboring layer along the z-axis.

Still referring to FIG. 44, a set of response curves 4250 are plotted for a first residual charged particle beam 267 at a first energy, $E_1$, that transmits through the stacked detector element 4400. As illustrated, a first member of the set of response curves is the first multi-color response curve 4251, described supra, related to the charged particles passing through the first sub-stack 4301. As the charged particles penetrate into the second sub-stack 4302, the charged particles continue to lose energy, which results in a second multi-color response curve 4252 comprising larger element-by-element responses compared to responses from the first sub-stack 4302. More particularly, the red scintillator response is larger from the second sub-stack 4302 than from the first sub-stack 4301. Larger responses from the green and blue scintillation materials also result, which combined with the material responsivity differences results in a distinct shape of the second response curve 4252 relative to a shape of the first response curve 4251. Similarly, passage of the charged particles through the third sub-stack 4303 and the fourth sub-stack 4304 results in a third multi-color response curve 4253 and a fourth multi-color response curve 4254 with a third and fourth distinct shape, respectively. Similarly, the set of response curves 4250 are also plotted for a second residual charged particle beam 267 at a second lower energy, $E_2$, that terminates, such as in a Bragg peak, within the stacked detector element 4400. More particularly, a fifth, sixth, seventh, and eighth multi-color response curve 4255, 4256, 4257, 4258 are illustrated for the lower second energy, relative to the first higher energy, $E_1$, residual charged particle beam. The lower energy beam, $E_2$ versus $E_1$, results in: (1) a larger response for a given depth and (2) in a larger curvature shape in each sub-stack, relative to the first residual charged particle beam due to a larger loss of energy, as described supra. If the set of emission layers is limited to one scintillation material, the response signals reduce to a Bragg peak with gaps along the z-axis. For example, referring still to FIG. 44, if only the first red emission scintillation layer of each sub-stack is plotted, the points fit a Bragg peak curve, with loss of the benefit of different responsivities of differing scintillation materials/colors.

As further described infra, initial energy of the residual charged particle beam 267 is determined using any 1, 2, 3, 4, 5, 6, 7, 8, 9, 10, or more points from the union of the response curves with or without a Bragg peak-like sudden stoppage of the charged particles within the stacked detector element 4400 or the multi-layer scintillator 4030.

Still referring to FIG. 44, as a given response curve, which changes for changing initial energy levels of the residual charged particle beam 267 is based on scintillator material types as a function of depth, once calibrated the initial energy of the residual charged particle beam 267 is determined using:

a response at any given depth;
a difference in response between any two depths;
2, 3, or more responses in a given sub-stack;
responses from single layers in 2, 3, or more sub-stacks;
responses from 2, 3, or more sub-stacks;
responses from a common scintillator material at two or more depths;
responses from a common scintillator material in 2, 3, or more sub-stacks;
a shape of a response curve of a given sub-stack;
a shape of a response curve comprising points from 2, 3, or more sub-stacks; and/or a shape of a response curve from two or more scintillation layers.

Still referring to FIG. 44, the inventor notes that error is reduced in determination of the initial energy of the residual charged particle beam 267 using:
- an increasing number of points in a given response curve from a given sub-stack;
- an increasing number of points from two or more sub-stacks;
- an increasing number of points from two or more layers of the multi-layer scintillator 4030;
- using two or more scintillation materials with different responsivities due to the change in response being large;
- a gap, along the z-axis, between two or more layers, which increases the change in response between the two or more layers;
- a beam slowing material, such as other scintillation layers, between two or more scintillation layers.

Reduction in error of determination of the initial energy of the residual charged particle beam 267, by way of additional data points, increases precision and/or accuracy of an image generated using the residual energies, such as a proton computed radiography (pRT) image; a proton computed tomography (pCT) image; and/or a positively charged particle radiography and/or tomography image.

Still referring to FIG. 44, shapes of the set of response curves 4250, shapes of combinations of members of the set of response curves 4250, and/or individual members of the set of response curves are optionally used, after calibration, to determine a full Bragg peak profile, including a position of the Bragg peak, even without observation of the Bragg peak for a given scintillation color. The inventor notes that the set of response curves represents multiple Bragg peak profiles, one for each scintillation color utilized in the multi-layer scintillator. The inventor further notes that multiple Bragg peaks enhances accuracy and/or resolution of the energy of the residual charged particle beam 760 as a result of the rapid drop off of a given Bragg peak relative to a thickness of a given scintillation layer and the opportunity to catch multiple points, a very sensitive and accurate measurement, of a Bragg peak falloff from different scintillation layers given multiple Bragg peaks occurring for different colors across junctions of layers in the set of layers in the multi-layer scintillator detector element 4110.

Still yet another embodiment includes any combination and/or permutation of any of the elements described herein.

The main controller, a localized communication apparatus, and/or a system for communication of information optionally comprises one or more subsystems stored on a client. The client is a computing platform configured to act as a client device or other computing device, such as a computer, personal computer, a digital media device, and/or a personal digital assistant. The client comprises a processor that is optionally coupled to one or more internal or external input device, such as a mouse, a keyboard, a display device, a voice recognition system, a motion recognition system, or the like. The processor is also communicatively coupled to an output device, such as a display screen or data link to display or send data and/or processed information, respectively. In one embodiment, the communication apparatus is the processor. In another embodiment, the communication apparatus is a set of instructions stored in memory that is carried out by the processor.

The client includes a computer-readable storage medium, such as memory. The memory includes, but is not limited to, an electronic, optical, magnetic, or another storage or transmission data storage medium capable of coupling to a processor, such as a processor in communication with a touch-sensitive input device linked to computer-readable instructions. Other examples of suitable media include, for example, a flash drive, a CD-ROM, read only memory (ROM), random access memory (RAM), an application-specific integrated circuit (ASIC), a DVD, magnetic disk, an optical disk, and/or a memory chip. The processor executes a set of computer-executable program code instructions stored in the memory. The instructions may comprise code from any computer-programming language, including, for example, C originally of Bell Laboratories, C++, C#, Visual Basic® (Microsoft, Redmond, Wash.), Matlab® (MathWorks, Natick, Mass.), Java® (Oracle Corporation, Redwood City, Calif.), and JavaScript® (Oracle Corporation, Redwood City, Calif.).

Herein, any number, such as 1, 2, 3, 4, 5, is optionally more than the number, less than the number, or within 1, 2, 5, 10, 20, or 50 percent of the number.

Herein, an element and/or object is optionally manually and/or mechanically moved, such as along a guiding element, with a motor, and/or under control of the main controller.

The particular implementations shown and described are illustrative of the invention and its best mode and are not intended to otherwise limit the scope of the present invention in any way. Indeed, for the sake of brevity, conventional manufacturing, connection, preparation, and other functional aspects of the system may not be described in detail. Furthermore, the connecting lines shown in the various figures are intended to represent exemplary functional relationships and/or physical couplings between the various elements. Many alternative or additional functional relationships or physical connections may be present in a practical system.

In the foregoing description, the invention has been described with reference to specific exemplary embodiments; however, it will be appreciated that various modifications and changes may be made without departing from the scope of the present invention as set forth herein. The description and figures are to be regarded in an illustrative manner, rather than a restrictive one and all such modifications are intended to be included within the scope of the present invention. Accordingly, the scope of the invention should be determined by the generic embodiments described herein and their legal equivalents rather than by merely the specific examples described above. For example, the steps recited in any method or process embodiment may be executed in any order and are not limited to the explicit order presented in the specific examples. Additionally, the components and/or elements recited in any apparatus embodiment may be assembled or otherwise operationally configured in a variety of permutations to produce substantially the same result as the present invention and are accordingly not limited to the specific configuration recited in the specific examples.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present invention, in addition to those not specifically recited, may be varied or otherwise particularly adapted to specific environments, manufacturing specifications, design parameters or other operating requirements without departing from the general principles of the same.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:

1. A method for determining residual energy of positively charged particles after passing through a patient, comprising the steps of:
    passing the positively charged particles into a multi-layer detector element;
    detecting first secondary photons, resultant from passage of the positively charged particles, over a first wavelength range from a first layer of said multi-layer detector, said first layer comprising a first scintillation material;
    detecting second secondary photons, resultant from passage of the positively charged particles, over a second wavelength range from a second layer of said multi-layer detector element, the first wavelength range differing from the second wavelength range; and
    determining, from a set of response signals generated from depths into said multi-layer detector element prior to a Bragg peak termination point of the first scintillation material, a depth of penetration of the positively charged particles into said multi-layer detector element.

2. A method for determining residual energy of positively charged particles after passing through a patient, comprising the steps of:
    passing the positively charged particles into a multi-layer detector element;
    detecting first secondary photons, resultant from passage of the positively charged particles, over a first wavelength range from a first layer of said multi-layer detector, said first layer comprising a first scintillation material;
    detecting second secondary photons, resultant from passage of the positively charged particles, over a second wavelength range from a second layer of said multi-layer detector element, the first wavelength range differing from the second wavelength range;
    transmitting the positively charged particles entirely through a backside of said multi-layer detection element relative to the patient; and
    determining an initial energy of the positively charged particles entering said multi-layer detection element from a response curve of said first secondary photons and said second secondary photons as a function of depth in said multi-layer detector element.

* * * * *